(12) United States Patent
Cory et al.

(10) Patent No.: US 7,865,236 B2
(45) Date of Patent: Jan. 4, 2011

(54) ACTIVE ELECTRODE, BIO-IMPEDANCE BASED, TISSUE DISCRIMINATION SYSTEM AND METHODS OF USE

(75) Inventors: Phillip C. Cory, Bozeman, MT (US); Joan M. Cory, Bozeman, MT (US); Waldean A. Schulz, Boulder, CO (US)

(73) Assignee: Nervonix, Inc., Bozeman, MT (US)

( * ) Notice: Subject to any disclaimer, the term of this patent is extended or adjusted under 35 U.S.C. 154(b) by 1032 days.

(21) Appl. No.: 11/252,568

(22) Filed: Oct. 19, 2005

(65) Prior Publication Data

US 2006/0085049 A1 Apr. 20, 2006

Related U.S. Application Data

(60) Provisional application No. 60/619,921, filed on Oct. 20, 2004.

(51) Int. Cl.
*A61B 5/053* (2006.01)
(52) U.S. Cl. .......................... 600/547; 607/48
(58) Field of Classification Search ............... 607/2, 607/48; 600/547
See application file for complete search history.

(56) References Cited

U.S. PATENT DOCUMENTS

| | | | |
|---|---|---|---|
| 4,962,766 A | 10/1990 | Herzon et al. | |
| 4,969,468 A | 11/1990 | Byers et al. | |
| 5,284,154 A | 2/1994 | Raymond et al. | |
| 5,458,117 A | 10/1995 | Chamoun et al. | |
| 5,560,372 A | 10/1996 | Cory | |
| 5,746,214 A | 5/1998 | Brown et al. | |
| 5,792,069 A | 8/1998 | Greenwald et al. | |
| 5,810,742 A * | 9/1998 | Pearlman ................ | 600/547 |
| 5,813,404 A | 9/1998 | Devlin et al. | |
| 5,830,151 A | 11/1998 | Hadzic et al. | |
| 5,853,373 A | 12/1998 | Griffith et al. | |
| 6,055,452 A | 4/2000 | Pearlman | |
| 6,157,697 A | 12/2000 | Mertelmeier et al. | |

(Continued)

FOREIGN PATENT DOCUMENTS

| WO | 00/19498 A | 4/2000 |
|---|---|---|
| WO | WO/01/87154 A | 11/2001 |
| WO | 02/100247 A | 12/2002 |

OTHER PUBLICATIONS

Gunn CC, Ditchburn FG, King MH, Renwick GL, "Acupuncture Loci: A Proposal for their Classification according to their Relationship to Known Neutral Structures", Am J Chin Med 1976; pp. 183-195, vol. 4, No. 2.

(Continued)

*Primary Examiner*—Niketa I Patel
*Assistant Examiner*—Rex Holmes
(74) *Attorney, Agent, or Firm*—The Marbury Law Group PLLC

(57) ABSTRACT

Systems and methods for discriminating and locating tissues within a body involve applying a waveform signal to tissue between two electrodes and measuring the electrical characteristics of the signal transmitted through the tissue. At least one of the electrodes is constrained in area so that localized electrical characteristics of the tissue are measured. Such localized electrical characteristics are determined over a portion of a body of the subject by using an array of electrodes or electrodes that can be moved over the body. A controller may implement the process and perform calculations on the measured data to identify tissue types and locations within the measured area, and to present results in graphical form. Results may be combined with other tissue imaging technologies and with image-guided systems.

19 Claims, 39 Drawing Sheets

U.S. PATENT DOCUMENTS

| | | | |
|---|---|---|---|
| 6,167,304 | A | 12/2000 | Loos |
| 6,236,874 | B1 | 5/2001 | Devlin et al. |
| 6,298,255 | B1 | 10/2001 | Cordero et al. |
| 6,308,097 | B1 | 10/2001 | Pearlman |
| 6,338,713 | B1 | 1/2002 | Chamoun et al. |
| 6,421,559 | B1 | 7/2002 | Pearlman |
| 6,466,817 | B1 | 10/2002 | Kaula et al. |
| 6,560,480 | B1 | 5/2003 | Nachaliel et al. |
| 6,564,079 | B1 | 5/2003 | Cory et al. |
| 6,609,018 | B2 | 8/2003 | Cory et al. |
| 6,706,016 | B2 | 3/2004 | Cory et al. |
| 6,760,616 | B2 | 7/2004 | Hoey et al. |
| 6,952,606 | B2 | 10/2005 | Anderson et al. |
| 2002/0065481 | A1 | 5/2002 | Cory et al. |
| 2003/0009111 | A1* | 1/2003 | Cory et al. .................. 600/547 |
| 2004/0158167 | A1 | 8/2004 | Smith et al. |
| 2004/0181165 | A1 | 9/2004 | Hoey et al. |

OTHER PUBLICATIONS

Morimoto T., et al., Measurement of the electrical bioimpedance of breast tumors, Eur Surg Res., 1990, pp. 86-92, vol. 22.

Cheney, Frederick W. MD et al., "Nerve Injury Associated with Anesthesia: A Closed Claims Analysis", The Journal of American Society of Anesthesiologists, Inc., 1999, pp. 1062-1069, vol. 90, No. 4.

Oaklander AL: The Density of Remaining Nerve Endings in Human Skin with and without Postherpetic Neuralgia after Shingles. Pain 2001; 92: 139-45.

McArthur JC, Stocks EA, Hauer P, Cornblath DR, Griffin JW: Epidermal Nerve Fiber Density. Arch. Neurol. 1998; 55: 1513-20.

Petersen KL, Rice FL, Suess F, Berro M, Rowbotham MC: Relief of post-herpetic neuralgia by surgical removal of painful skin. Pain 2002; 98: 119-26.

Nolano M, Simone DA, Wendelschafer-Crabb G, Johnson T, Hazen E, Kennedy WR: Topical capsaicin in humans: parallel loss of epidermal nerve fibers and pain sensation. Pain 1999; 135-45.

Finkelstien A, Mauro A: Physical Principles and Formalisms of Electrical Excitability, The Nervous System. Edited by Brookhart JM, Mountcastle VB, Kandel ER. Baltimore, MD, Waverly Press, Inc., 1977, pp. 161-213.

Cooper MS: Membrane Potential Perturbations Induced in Tissue Cells by Pulsed Electric Fields. Bioelectromagnetics 1995; 16: 255-62.

Rudy Y, Plonsey R: The eccentric spheres model as the basis for a study of the role of geometry and inhomogeneities in electrocardiography. IEEE Trans. Biomed. Eng. 1979; BME-26: 392-9.

Cole KS: Membranes, ions, and impulses. Berkeley and Los Angeles, University of California Press, 1972, pp. 1-569.

Cooper MS: Gap junctions increase the sensitivity of tissue cells to exogenous electric fields. J. Theor. Biol. 1984; 111: 123-30.

Gabriel C, Gabriel S, Corthout E: The dielectric properties of biological tissues: I. Literature survey. Phys. Med. Biol. 1996; 41: 2231-49.

Gabriel S, Lau RW, Gabriel C: The dielectric properties of biological tissues: II. Measurements in the frequency range 10Hz to 20GHz. Phys. Med. Biol. 1996; 41: 2251-69.

Gabriel S, Lau RW, Gabriel C: The dielectric properties of biological tissues: III. Parametric models for the dielectric spectrum of tissues. Phys. Med. Biol. 1996; 41: 2271-93.

Rall W: Theory of Physiological Properties of Dendrites. Ann. NY Acad. Sci. 1962; 96: 1071-92.

Holder DS: Impedance changes during the compound nerve action potential: implications for impedance imaging of neuronal depolarisation in the brain. Med. & Biol. Eng. & Comput. 1992; 30: 140-6.

Jongschaap HCN, Wytch R, Hutchison JMS, Kulkarni V: Electrical Impedance Tomography: A Review of Current Literature. Eur. J. Radiol. 1994; 18: 165-74.

Johng HM, Cho JH, Shin HS, Soh KS, Koo TH, Choi SY, Koo HS, Park MS: Frequency Dependence of Impedances at the Acupuncture Point QUZE (PC3). IEEE Eng. Med. Biol. 2002; 33-6.

Prokhovav E, Llamas F, Morales-Sanchez E, Gonzalez-Hernandez J, Prokhorav A: in Vivo Impedance Measurements on Nerves and Surrounding Skeletal Muscles in Rats and Human Body. Med. & Biol. Eng. & Comput. 2002; 40: 323-6.

Geddes LA: Historical Evolution of Circuit Models for the Electrode-Electrolyte Interface. Ann Biomed Eng 1997; 25: 1-14.

Brown, et al. in Blood Flow Imaging Using Electrical Impedance Tomography, (Clin. Phys. Physiol. Meas. 1992; 13 suppl A: 175-9).

Rall, W., Core Conductor Theory and Cable Properties of Neurons, Handbook of Physiology, section 12, the Nervous System. Edited by Brookhart JM, Mountcastle VB, Kande ER. Baltimore, MD, 1977, pp. 39-97.

Reichmanis M, Marino AA, Becker RO: Electrical Correlates of Acupuncture Points. IEEE Trans.Biomed.Eng. 1975; BME 22: 533-532.

Hodgkin AL, Huxley AF: A Quantitative Description of Membrane Current and its Application to Conduction and Excitation in Nerve. J. Physiol. 1952; 117: 500-44.

Mauro A: Anomalous Impedance, A Phenomenological Property of Time-Variant Resistance: An Analytic Review. Biophysical Journal 1961; 1: 353-72.

Gabriel S, Lau RW, Gabriel C: The dielectric properties of biological tissues: II. Measurements in the frequency range 10Hz to 20GHz. Phys. Med. Biol. 1996; 41: 2251-69.

Sabah NH, Leibovic KN: Subthreshold oscillatory responses of the Hodgkin-Huxley cable model for the squid giant axon. Biophys. J. 1969; 9: 1206-22.

Mauro A, Conti F, Dodge F, Schor R: Subthreshold behavior and phenomenological impedance of the squid giant axon. J. Gen. Physiol. 1970; 55: 497-523.

Cole KS, Baker RF: Longitudinal impedance of the squid giant axon. J. Gen. Physiol. 1941; 24: 771-88.

Cole KS: Rectification and inductance in the squid giant axon. J. Gen. Physiol. 1941; 25: 29-51.

Cole KS: Electric impedance of suspensions of spheres. J. Gen. Physiol. 1928; 12: 29-36.

Cole KS: Electric impedance of suspensions of arbacia eggs. J. Gen. Physiol. 1928; 12: 37-54.

Cole KS: Electric phase angle of cell membranes. J. Gen. Physiol. 1932; 15: 641-9.

Cole KS, Hodgkin AL: Membrane and protoplasm resistance in the squid giant axon. J. Gen. Physiol. 1939; 22: 671-87.

Cole KS, Baker RF: Transverse impedance of the squid giant axon during current flow. J. Gen. Physiol. 1941; 24: 535-49.

Lykken DT: Square-Wave Analysis of Skin Impedance. Psychophysiology 1971; 7: 262-75.

Kaslow AL, Lowenschuss O: Dragon Chasing: A New Technique for Acupuncture Point Finding and Stimulation. Am. J. Acupunct. 1975; 3: 157-60.

England JD, Happel LT, Kline DG, Gamboni F, Thouron CL, Liu ZP, Levinson SR: Sodium Channel Accumulation in Humans with Painful Neuromas, Neurology 1996; 47: 272-276.

Kwok G, Cohen M, Cosic I: Mapping Acupuncture Points Using Multi Channel Device. Australas. Phys. Eng. Sci. Med. 1998; 21: 68-72.

Edelberg R: Electrical Properties of Skin, Biophysical Properties of the Skin. Edited by Elden HR, Wiley-Interscience, 1972, pp. 513-550).

Life-Tech flyer entitled StimProbe Model SP1, ProBloc Needle Selection, Life-Tech, Inc., Stafford, Texas.

U.S. Appl. No. 11/252,556, filed Oct. 19, 2005, Cory et al. Nervonix, Inc.

* cited by examiner

Fig. 26
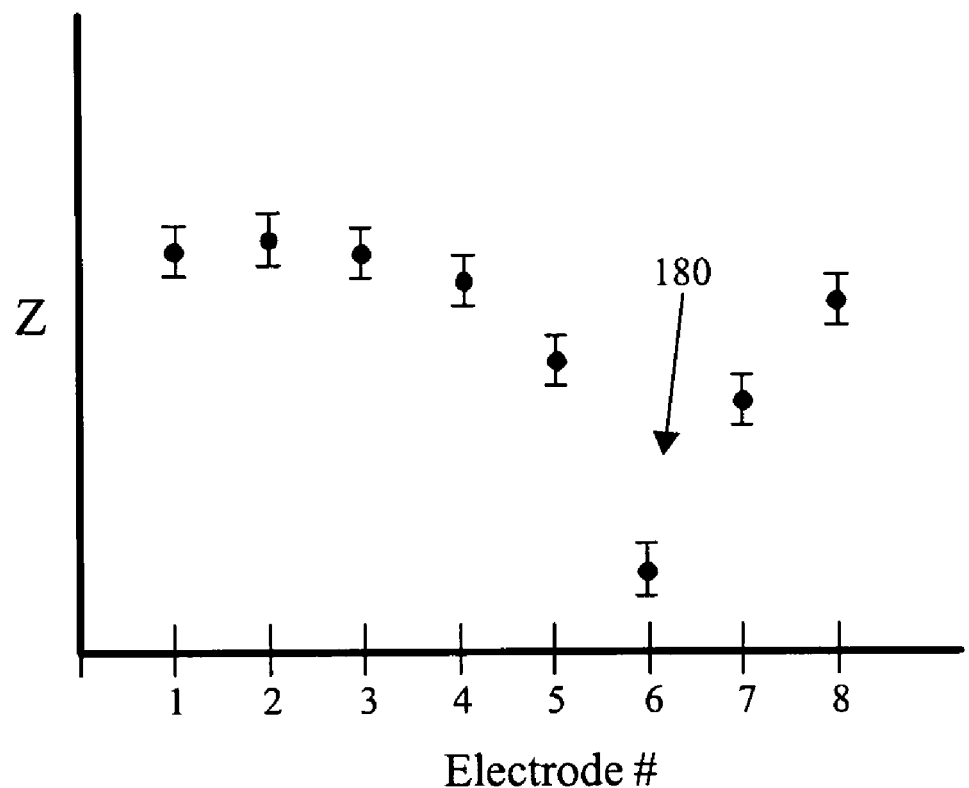
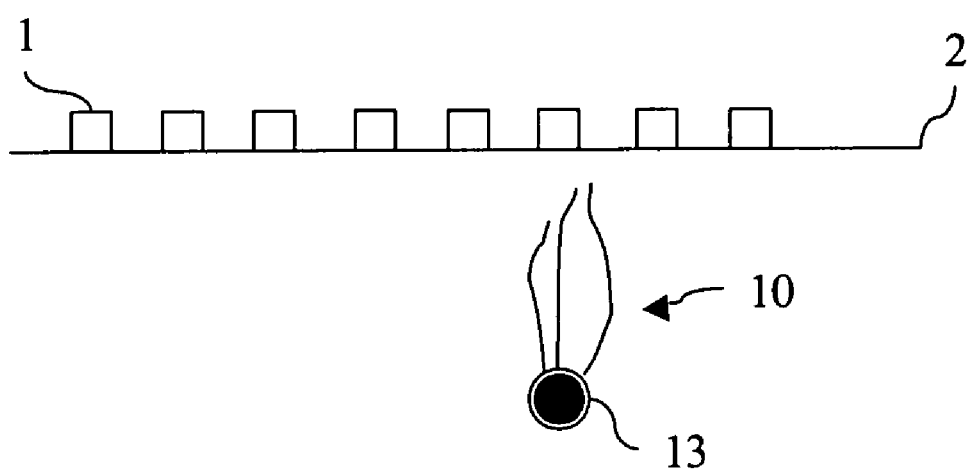

ACTIVE ELECTRODE, BIO-IMPEDANCE BASED, TISSUE DISCRIMINATION SYSTEM AND METHODS OF USE

RELATED APPLICATIONS

This specification claims the benefit of and priority to U.S. Provisional Patent Application No. 60/619,921 filed Oct. 20, 2004, the entire contents of which are hereby incorporated by reference. This application is also related to U.S. application Ser. No. 11/252,556 entitled "Algorithms for an Active Electrode, Bioimpedance-based Tissue Discrimination System" filed concurrently herewith, and now abandoned, the entire contents of which are hereby incorporated by reference. This application is also related to U.S. application Ser. No. 09/989, 206 filed Nov. 21, 2001, now U.S. Pat. No. 6,706,016; Ser. No. 10/170,194 filed on Jun. 13, 2002, now abandoned; Ser. No. 10/772,397 filed Feb. 6, 2004, now U.S. Pat. No. 7,047, 085; and Ser. No. 10/853,590 filed May 25, 2004, now U.S. Pat. No. 7,212,865; the contents of each of which are herein incorporated by reference in their entireties.

FIELD OF THE INVENTION

The present invention provides non-invasive methods and systems for discriminating and mapping types of tissue. Particularly, the present invention relates to tissue discrimination and mapping by the application of a waveform to a subject and monitoring changes in the waveform induced by the electrical characteristics of the subject. More particularly, these methods and systems may be applied to identification and evaluation of nerve tissue.

BACKGROUND

Non-invasive detection of subcutaneous tissues has concerned medical practitioners for many years. It is known by practitioners that many forms of subcutaneous tissue are responsive to electrical signals. Biologic, electrically responsive membrane systems (BERMS) are lipid bi-layers containing embedded protein molecules, some of which are ion channels. The density of embedded ion channels varies by tissue type, with nerve tissue having the highest concentrations of ion channels per gram of tissue. Nerve abnormalities, e.g., neuromas, have even higher concentrations of ion channels than normal nerve tissue. Other tissues, e.g., muscle, have lower densities than normal nerve tissue.

Prior art for noninvasive, electrically based, determination from the skin surface of tissue depth, composition, configuration, and/or state of function either detects a change in the function of the biological tissue structure in response to stimulation or assumes characteristics about electrical field paths in tissue. In one technique the location of nerve is detected by generating action potentials in nerves from certain electrodes within an array of electrodes.

U.S. Pat. No. 6,167,304 to Loos discusses the use of induced electrical fields to cause nerve "resonance." It is unclear specifically what is meant by the term resonance in the Loos disclosure. This resonance occurs at certain frequencies and is associated with physiological findings. However, it is clearly not the same as the electrical phenomenon of resonance, which is a function of inductance and capacitance connected either in series or in parallel, with a resistance resulting in marked impedance changes at a single, unique frequency. The determination of impedance plays no role in the Loos resonance, which occurs at multiple frequencies.

U.S. Pat. No. 5,560,372 to Cory (herein incorporated by reference) teaches that, under certain conditions, the applied voltage required for maintenance of controlled current flow through skin surface electrodes is reduced when measured on skin over the position of peripheral nerves as compared to skin not overlying significant nerve tissue. This capability has not been addressed with other techniques, e.g., electrical impedance tomography (EIT). The device in Cory does not require action potential generation. This device indicated the lowest impedance site within its field by activating a single light emitting diode (LED) corresponding to the electrode contacting the skin surface at that site.

In the technique of EIT, current flow between a pair of electrodes causes simultaneous voltage, amplitude, phase, or waveform variations at other, non-current carrying electrodes arrayed on the body surface or in subcutaneous tissues, as described in U.S. Pat. No. 6,055,452 to Pearlman. Varying the electrode pairs through which current is flowing, followed by combining and analyzing the data, allows construction of specific impedance images that may be related to underlying structures. A key assumption for the performance of EIT is that tissues have unique electrical characterizations, the most important being the specific impedance, tissue resistivity, and tissue dielectric constant. The electrical field itself supposedly does not affect these parameters, although changes in organ size, content, conformation, or state of function are reflected in altered conductivity patterns. The technique of EIT analyzes voltage information from the skin surface at points distinct from the current carrying pair of electrodes. The assumption is made that tissue resistivities or dielectric constants are stable in the presence of these electrical fields, allowing the calculation of current flow patterns beneath the skin surface and construction of images from those patterns. In this technique, resolution and identification of subsurface structures remains a problem.

The recognition that tissue represents a non-homogeneous conductor best modeled as a parallel resistance and capacitance with a series resistance has enabled determination of the bulk conductor electrical properties of tissue. Below are listed notable research papers in this field establishing some of the physiological and technological foundation upon which the present invention is based:

1. Oaklander A L: The Density of Remaining Nerve Endings in Human Skin with and without Postherpetic Neuralgia after Shingles. Pain 2001; 92: 139-45;
2. McArthur J C, Stocks E A, Hauer P, Comblath D R, Griffin J W: Epidermal Nerve Fiber Density. Arch. Neurol. 1998; 55: 1513-20;
3. Petersen K L, Rice F L, Suess F, Berro M, Rowbotham M C: Relief of post-herpetic neuralgia by surgical removal of painful skin. Pain 2002; 98: 119-26;
4. Nolano M, Simone D A, Wendelschafer-Crabb G, Johnson T, Hazen E, Kennedy W R: Topical capsaicin in humans: parallel loss of epidermal nerve fibers and pain sensation. Pain 1999; 135-45;
5. Hodgkin A L, Huxley A F: A Quantitative Description of Membrane Current and its Application to Conduction and Excitation in Nerve. J. Physiol. 1952; 117: 500-44;
6. Rall W: Core Conductor Theory and Cable Properties of Neurons, Handbook of Physiology, section 1, The Nervous System. Edited by Brookhart J M, Mountcastle V B, Kandel E R. Baltimore, Md., Baltimore, Md., 1977, pp. 39-97;
7. Finkelstien A, Mauro A: Physical Principles and Formalisms of Electrical Excitability, The Nervous System. Edited by Brookhart J M, Mountcastle V B, Kandel E R. Baltimore, Md., Waverly Press, Inc., 1977, pp. 161-213;

8. Mauro A: Anomalous Impedance, A Phenomenological Property of Time-Variant Resistance: An Analytic Review. Biophysical Journal 1961; 1: 353-72;
9. Cooper M S: Membrane Potential Perturbations Induced in Tissue Cells by Pulsed Electric Fields. Bioelectromagnetics 1995; 16: 255-62;
10. Sabah N H, Leibovic K N: Subthreshold oscillatory responses of the Hodgkin-Huxley cable model for the squid giant axon. Biophys. J. 1969; 9: 1206-22;
11. Mauro A, Conti F, Dodge F, Schor R: Subthreshold behavior and phenomenological impedance of the squid giant axon. J. Gen. Physiol. 1970; 55: 497-523;
12. Cole Kans., Baker R F: Longitudinal impedance of the squid giant axon. J. Gen. Physiol. 1941; 24: 771-88;
13. Cole K S: Rectification and inductance in the squid giant axon. J. Gen. Physiol. 1941; 25: 29-51;
14. Rudy Y, Plonsey R: The eccentric spheres model as the basis for a study of the role of geometry and inhomogeneities in electrocardiography. IEEE Trans. Biomed. Eng. 1979; BME-26: 392-9;
15. Cole K S: Electric impedance of suspensions of spheres. J. Gen. Physiol. 1928; 12: 29-36;
16. Cole K S: Electric impedance of suspensions of arbacia eggs. J. Gen. Physiol. 1928; 12: 37-54;
17. Cole K S: Electric phase angle of cell membranes. J. Gen. Physiol. 1932; 15: 641-9;
18. Cole K S, Hodgkin Ala.: Membrane and protoplasm resistance in the squid giant axon. J. Gen. Physiol. 1939; 22: 671-87;
19. Cole K S, Baker R F: Transverse impedance of the squid giant axon during current flow. J. Gen. Physiol. 1941; 24: 535-49;
20. Cole K S: Membranes, ions, and impulses. Berkeley and Los Angeles, University of California Press, 1972, pp. 1-569;
21. Cooper M S: Gap junctions increase the sensitivity of tissue cells to exogenous electric fields. J. Theor. Biol. 1984; 111: 123-30;
22. Gabriel C, Gabriel S, Corthout E: The dielectric properties of biological tissues: I. Literature survey. Phys.Med. .Biol. 1996; 41: 2231-49;
23. Gabriel S, Lau R W, Gabriel C: The dielectric properties of biological tissues: II. Measurements in the frequency range 10 Hz to 20 GHz. Phys. Med. Biol. 1996; 41: 2251-69;
24. Gabriel S, Lau R W, Gabriel C: The dielectric properties of biological tissues: III. Parametric models for the dielectric spectrum of tissues. Phys. Med. Biol. 1996; 41: 2271-93;
25. Rall W: Theory of Physiological Properties of Dendrites. Ann. NY Acad. Sci. 1962; 96: 1071-92;
26. Holder D S: Impedance changes during the compound nerve action potential: implications for impedance imaging of neuronal depolarisation in the brain. Med. & Biol. Eng. & Comput. 1992; 30: 140-6;
27. Jongschaap H C N, Wytch R, Hutchison J M S, Kulkarni V: Electrical Impedance Tomography: A Review of Current Literature. Eur. J. Radiol. 1994; 18: 165-74;
28. Kwok G, Cohen M, Cosic I: Mapping Acupuncture Points Using Multi Channel Device. Australas. Phys. Eng. Sci. Med. 1998; 21: 68-72;
29. Lykken D T: Square-Wave Analysis of Skin Impedance. Psychophysiology 1971; 7: 262-75;
30. Kaslow A L, Lowenschuss O: Dragon Chasing: A New Technique for Acupuncture Point Finding and Stimulation. Am. J. Acupunct. 1975; 3: 157-60;
31. Reichmanis M, Marino A A, Becker R O: Electrical Correlates of Acupuncture Points. IEEE Trans. .Biomed.Eng. 1975; BME 22: 533-532;
32. Johng H M, Cho J H, Shin H S, Soh K S, Koo T H, Choi S Y, Koo H S, Park M S: Frequency Dependence of Impedances at the Acupuncture Point QUZE (PC3). IEEE Eng. Med. Biol. 2002; 33-6;
33. Prokhovav E, Llamas F, Morales-Sanchez E, Gonzalez-Hemandez J, Prokhorav A: In Vivo Impedance Measurements on Nerves and Surrounding Skeletal Muscles in Rats and Human Body. Med. & Biol. Eng. & Comput. 2002; 40: 323-6; and
34. England J D, Happel L T, Kline D G, Gamboni F, Thouron C L, Liu Z P, Levinson S R: Sodium Channel Accumulation in Humans with Painful Neuromas, Neurology 1996; 47: 272-276.

Accordingly, there exists a need to non-invasively detect tissue substructures in a sample which can accurately locate, identify, and discriminate the tissue substructures.

SUMMARY OF THE INVENTION

The present invention provides improved systems, apparatus and methods for accurately locating and discriminating tissue substructures using bioimpedance which avoid the problems described above. The technology monitors changes induced by localized electrical characteristics of the subject in an applied electrical field, recognizing that the applied electrical field may induce changes in the subject electrical parameters. The current invention may be used, for example, to detect changes in an applied electrical waveform due to the presence of peripheral nerves and thereby generate a nerve tissue density distribution.

An apparatus of the present invention may comprise: a controller (such as a processor, microcomputer, microcontroller or microprocessor); a waveform generator operable to generate a plurality of different waveforms in response to instructions received from the controller, the waveform generator being connected to at least one waveform electrode; at least one waveform electrode and at least one return electrode operable to measure the waveform across the tissue of the subject between the at least one waveform electrode and the at least one return electrode, the return electrode being connected to the controller, thereby completing an electrical circuit which includes the tissue of the subject as a component, wherein the controller determines information indicative of the voltage, current, and phase characteristics of the applied waveform and calculates other electrical characteristics of the tissue of the test subject.

An embodiment of the nerve locating and imaging system includes the following hardware components: an electrode array assembly comprising multiple rows of multiple electrodes (e.g., 6 rows of 10 electrodes); electrolyte-filled wells electrically connecting the electrodes to a subject's skin; a return (or ground or common) electrode located a distance (e.g., about 20 cm) away from the electrode array assembly; electronics circuitry (and potentially embedded firmware) to generate a specified waveform to one or more selected waveform electrodes, simultaneously measuring the voltage and the current flow between each waveform electrode and return electrode, receiving commands to generate the waveform, and transmitting the measurement data; a conductor for each electrode leading from it to the circuitry; a host computer which contains control and processing software, originating the specified commands to the circuitry, receiving the measurement data, processing the data to determine the location of nerve tissue by computing relative electrical characteristics at each electrode, processing the measurement data for graphical display of electrical characteristics between electrodes, displaying the processed data numerically or graphically to indicate the detected location of nerve tissue, correlating the data with the physical location on the array by overlaying the data with an outline of the array; a two-way communications link between the circuitry and the host computer to communicate the commands from the computer to the circuitry and communicate the measured data from the circuitry to the computer, where the link may be an electrical cable, e.g., an RS-232 serial cable or USB, or a wireless datalink transceivers providing a wireless datalink, e.g., one that uses IEEE 802.11 g WiFi (wireless fidelity) or Bluetooth radio frequency (RF) datalinks, or an infrared (IR) datalink, or other wireless technology, standard, or protocol as will be developed. In the apparatus of the present invention, the characteristic which is calculated may be the impedance, the reactance, and/or the frequency response or other electrical characteristic of the tissue.

In the apparatus of the present invention, the controller may be operable to: instruct the waveform generator to generate a plurality of different waveforms to be applied to the tissue, to selectively calculate the impedance of the tissue for each generated waveform of the plurality of different waveforms, and to determine a ratio of a change in impedance to a change in applied current, voltage, or frequency; a change in applied current to a change in applied frequency; a change in applied voltage to a change in applied frequency; a change in phase to current, voltage, or frequency; a change in resistance to current, voltage or frequency; a change in capacitance to current, voltage, or frequency; and/or the first, second, or partial derivatives of the foregoing.

In the apparatus of the present invention the at least one waveform electrode may comprise a plurality of waveform electrodes and the apparatus may further comprise a switching device operable to receive instructions from the controller to provide a waveform to any waveform electrode of the plurality of waveform electrodes.

In the apparatus of the present invention, the switching device may be operable to simultaneously provide a single waveform to more than one waveform electrode.

In the apparatus of the present invention, the switching device may be operable to simultaneously provide a plurality of waveforms to more than one waveform electrode in a manner which provides the same waveform to each of the waveform electrodes.

In the apparatus of the present invention, the at least one return electrode may comprise a plurality of return electrodes and wherein the apparatus further comprises a return switching device operable to receive instructions from the microprocessor to select any return electrode of the plurality of return electrodes to thereby complete an electrical circuit between the at least one waveform electrode and the selected return electrode.

In the apparatus of the present invention, the at least one waveform electrode may comprise a plurality of waveform electrodes and the apparatus may further include a switching device operable to receive instructions from the controller to provide a waveform to any waveform electrode of the plurality of waveform electrodes, and the at least one return electrode may comprise a plurality of return electrodes and the apparatus may further include a return switching device operable to receive instructions from the controller to select any return electrode of the plurality of return electrodes to thereby complete an electrical circuit between the at least one waveform electrode and the selected return electrode.

The apparatus of the present invention may further comprise a display, and the controller may generate a nerve tissue density distribution or probability map depicting x and y locators and a height related to the probability of nerve tissue under specific x, y coordinates and the display may be operable to display such an image. Data related to tissue depth and/or time may additionally be incorporated into said images.

The method of detecting tissue structures of the present invention may comprise the steps of: generating a waveform; providing the waveform to tissue of a subject between at least one waveform electrode and at least one return electrode, thereby completing an electrical circuit which includes the tissue of the subject as a component, determining information indicative of the voltage, current, and phase of the applied waveform; and calculating an electrical characteristic of the tissue of the test subject associated with the applied waveform.

In the method of the present invention, the characteristic which is calculated may be the impedance of the tissue, the reactance, and/or the frequency response of the tissue. Additionally, the first, second, or partial derivatives of these parameters may be calculated.

The method of the present invention may further comprise the steps of: generating a new waveform, which may be periodic, aperiodic, complex or include multiple frequencies, and which is different from a previous waveform; providing the new waveform across the tissue of a subject between the waveform electrode and the return electrode as another applied waveform, thereby completing an electrical circuit which includes the tissue of the subject as a component; receiving information indicative of the voltage, current, and phase of the another applied waveform; and calculating an electrical characteristic of the tissue of the test subject associated with the another applied waveform.

The method of the present invention, may further comprise the step of performing calculations using characteristics of the applied waveform and characteristics of the another applied waveform.

In the method of the present invention, the calculation that is performed may be a determination of a ratio of a change in impedance to a change in applied current, voltage, or other electrical parameter.

The at least one waveform electrode may comprise a plurality of waveform electrodes. The method may further comprise the step of simultaneously providing a single waveform to more than one waveform electrode.

The method of the present invention may further comprise the steps of: calculating the impedance of the tissue for the new waveform, and determining a ratio of a change in impedance and a change in applied current determined for the tissue of the test subject for the applied waveform and the another applied waveform. In addition to or in place of impedance, other electrical parameters may be calculated.

In the method of the present invention the at least one waveform electrode may comprise a plurality of waveform electrodes, and the method may further comprise the step of: simultaneously providing a plurality of waveforms to more than one waveform electrode in a manner which provides the same current waveform to each of the waveform electrodes of the more than one waveform electrode.

The method of the present invention may further comprise the steps of: generating a nerve tissue density distribution; and displaying the nerve tissue density distribution.

A computer readable medium embodying the present invention may carry instructions to cause a computer to institute the performance of a method, the method comprising the steps of: generating a waveform; providing the waveform across the tissue of a subject between at least one waveform electrode and at least one return electrode, thereby completing an electrical circuit which includes the tissue of the subject as a component, determining information indicative of the voltage and current of the applied waveform; and calculating an electrical characteristic of the tissue of the test subject associated with the applied waveform.

BRIEF DESCRIPTION OF THE DRAWINGS

The accompanying drawings, which are incorporated in and form a part of the specification, illustrate the various embodiments of the invention and, together with the description, serve to explain the principles of the invention.

FIG. 26 illustrates impedance values sensed in a linear series of electrodes overlying nerve using an embodiment of the present invention.

DETAILED DESCRIPTION OF THE INVENTION

Reference will now be made in detail to the present embodiments of the invention, examples of which are illustrated in the accompanying drawings.

Figure 1:
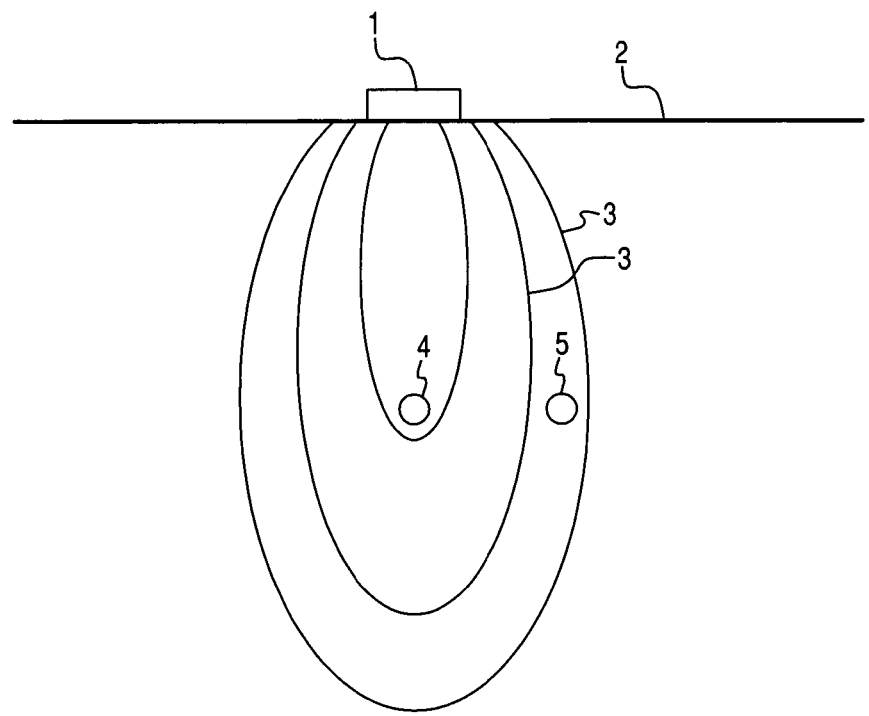
FIG. 1 illustrates the effect of an applied electrical field conventionally assumed to exist in an ideal homogeneous medium.
Figure 2:
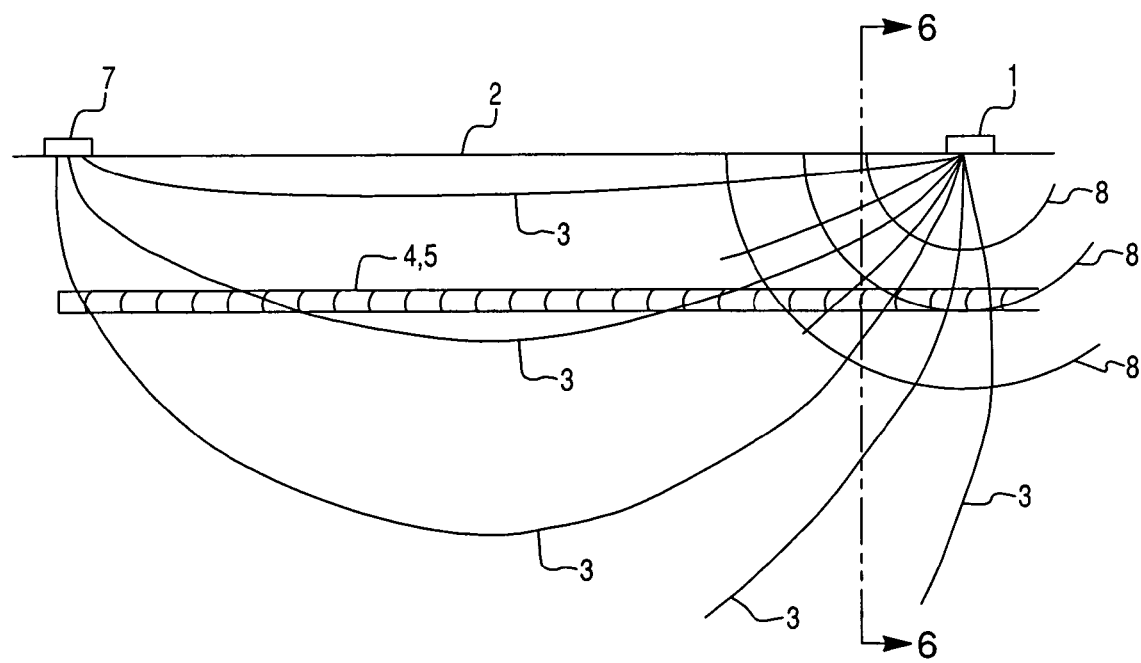
FIG. 2 illustrates the effect of an applied electrical field conventionally assumed to exist in an ideal homogeneous medium in a plane orthogonal to the plane of FIG. 1.

The inventors of the present invention have determined that complex impedance changes occur in living tissue which affect electrical measurements performed over the tissues and which are related at least in part to the cell membranes. It has been further determined that tissue impedance exhibits inverse relationships to variable, increasing currents when studied at frequencies of less than or equal to about 10 kilohertz (kHz). FIGS. 1-2 are directed to considerations of a conductive medium to illustrate the principle of operation of the invention. However, as those of skill in the art will appreciate, most living tissue is non-homogeneous and anisotropic; thus, the present invention is directed toward detection of tissues in non-homogeneous, anisotropic as well as homogeneous, isotropic tissue.

In FIGS. 1 and 2, waveform electrode sits on skin surface 2 overlying ideal, homogeneous subcutaneous tissue in which reside biological, electrically responsive membrane systems (BERMS) such as nerves 4 and 5. For the sake of this illustration, two ideal, identical nerves 4, 5 are located the same distance beneath the skin surface, but one nerve 4 is at a normal angle to the position of waveform electrode 1 and the other nerve 5 is at an angle other than a 90° angle to waveform electrode 1. For an electrical field at 90° to the plane connecting the nerves 4 and 5 and the waveform electrode 1 on skin surface 2, nerve 4 will experience a greater current density than nerve 5. It is recognized that the shape of the current density distribution will be altered by the nerve in the real situation as is discussed with respect to FIGS. 4 and 5, but for discussion purposes, this effect will be ignored for FIGS. 1 and 2. This difference in applied current densities will be true for all applied current levels and means that the $\Delta Z/\Delta I$ will be greater for nerve 4 than for nerve 5.

BERMS appear to demonstrate impedance discontinuities in an externally applied electrical field. This membrane effect occurs in addition to the widely appreciated membrane resistance and membrane capacitance. Sub-threshold, alternating, electrical fields do not generate action potentials, but cause anomalous impedance (appearing as an inductance), which has been noted and modeled in single axon systems. Mauro, Anomalous Impedance, A Phenomenological Property Of Time-Variant Resistance, An Analytic Review, (The Rockefeller Institute (1961)), proposes a mechanism to explain this anomalous impedance, which is based on the effect of normal membrane currents flowing across the nerve cell membrane in the opposite direction to the applied field. These currents are associated with time variant, ion-specific conductance and behave electrically as inductance. In addition, Sabah and Leibovic, Subthreshold Oscillatory Responses Of The Hodgkin-Huxley Cable Model For The Squid Giant Axon, (Department of Biophysical Sciences, Center for Theoretical Biology, State University of New York at Buffalo, Amherst, N.Y. (1969)), disclose circuit models of membrane electrical inductance, connected in parallel with membrane capacitance and membrane resistance and predict an electrical resonance effect.

With regard to resistivity, as illustrated in FIGS. 1 and 2, the scalar quantity current (or electrical field strength) traditionally has been assumed to follow a spindle-shaped distribution between two skin surface electrodes 1 and 7 in homogeneous, conductive material. FIGS. 1 and 2 illustrate the current distribution in a homogeneous, conductive medium. The current density at a point farther away from the center of the current distribution spindle will be lower than the current density closer to the center of the current distribution spindle. In a homogeneous medium, as illustrated in FIG. 1, isocurrent lines 3 are formed in planes intersecting the line of the current-carrying electrodes at 90°. Thus, nerve 4 is located on an isocurrent line 3 having a greater value than that for nerve 5. The actual current density at nerve 5 will be lower than at nerve 4 under these assumptions. As illustrated in FIG. 2, the equipotential lines 8 are at right angles to the isocurrent lines 3.

Figure 3:
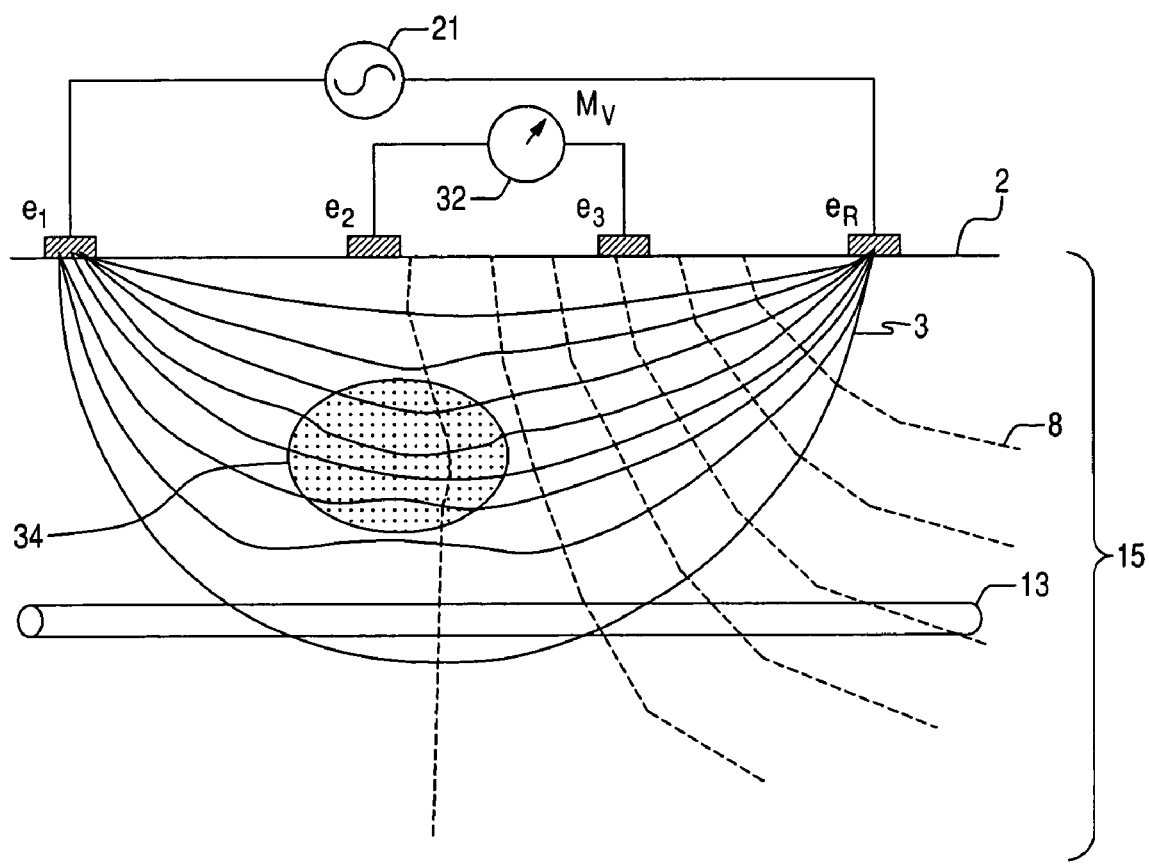
FIG. 3 illustrates the relationship between current and voltage in an applied electrical field conventionally assumed to exist in a non-homogeneous medium, with the axis of the field aligned with the page.

Referring to FIG. 3, in a non-homogeneous medium, portions of a reduced resistivity subsurface structure 34 arrayed along an individual equipotential line 8 will experience different actual current densities depending on their distance from the center of the current distribution spindle. In addition, in a non-homogeneous medium, where tissue resistivity or susceptivity may be current, voltage, or frequency dependent, the resistivity or susceptivity of identical tissues will vary depending on the distance a measurement point lies from the center of the current distribution spindle. Alterations in applied current I or voltage V occurring at the skin surface 2 will cause the impedance Z at any point in the electrical field to change as a consequence of the resistivity or susceptivity variations induced by current density shifts at that particular measurement point.

EIT is based upon such a model of electrical field distribution through bulk tissue derived from theoretical current flow calculations for bulk conductors. The calculations utilized to process data gathered by EIT systems start with the application of Maxwell's equations in homogeneous, bulk conductors and then modify the equations to account for non-homogeneous subsurface structures 34 within the bulk conductors, which represent tissues of varying resistivities. Similar approaches have been used for over a century in resistivity prospecting whereby underground ore bodies are identified through surface resistance mapping. Although complex back projection algorithms have been developed for use in EIT to create images of constituent tissues lying in an electrical field, the resolution of these images continues to be inadequate for routine clinical use.

The inventors have determined that EIT back projection algorithms fail to account for the fact that tissue is not only non-homogeneous, it is also anisotropic. The inventors have further determined that the most remarkable electrical anisotropicity of living tissue is that the neuroanatomy represents preferential conductance pathways through tissue, altering current flow from a prolate ellipsoid shape to a more constrained and angular path following the major nerves. To provide a more valid model for EIT and for functional electrical stimulation, the nerve density and depth information beneath an electrode array assembly must be taken into account. After mapping the anatomic distribution of the major conductive pathways (nerves), a model for electrical field distribution could then be constructed and the predictive distributions of skin surface potential determined for comparison with the actual distributions. A relevant example comprises the observations upon which some EIT breast cancer detection systems are based. Breast cancer lesions are reported to exhibit significantly higher resistance values and lower capacitance values than normal tissue or benign tumors. These observations are consistent with a paucity of nerve tissue in non-neural malignancies. Useful information could therefore be obtained using the present invention to determine not only where nerves exist, but also where nerves are expected and not present at normal levels.

Figure 4:
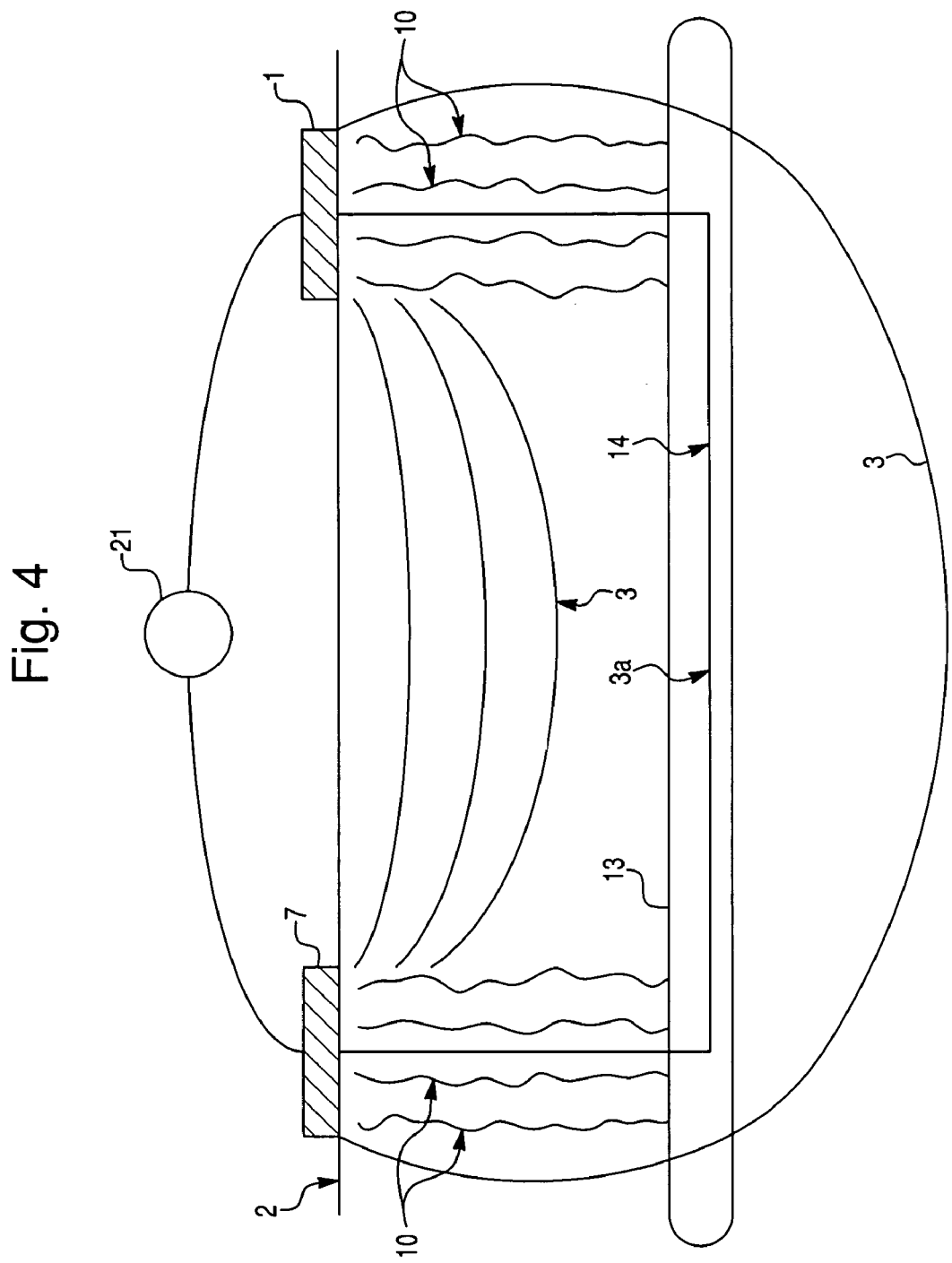
FIG. 4 illustrates a model for the electrical path through tissue including a nerve.

Equivalent circuit models of nerve cell membranes may be represented as parallel RC circuits, where the resistance represents voltage-gated ion channels and the capacitance represents membrane capacitance [Mauro A, 1961; Rall W, 1977; Sabah N, 1969]. According to this model, the resistance represents the real component and the capacitance represents the reactive component of the complex impedance determined across the tissue. The inventors believe that an important factor in tissue discrimination is the concentration of voltage-gated channels in the cell membranes of biological tissues. The sodium and potassium channels act as voltage-gated ion switches, so that in the presence of a transmembrane voltage gradient of sufficient magnitude and duration, the channels open to allow sodium or potassium ions to cross the cellular membrane. Nerve tissue, with the highest density of voltage-gated channels in the body [England, 1996] and its elongated structure, presents preferential conduction paths through tissue as illustrated in FIG. 4. The concentration of voltage-gated channels is lower in muscle, and even lower for other known cell types (e.g., endothelial cells in vessel walls). Further, nerves resemble parallel conductors bundled together, wherein the resistance across the membrane (the transmembrane resistance) is greater than the resistance down the interior of the nerve (the longitudinal resistance). This structure facilitates conduction of electric fields down the long, uninterrupted tubes represented by the axons within the nerve. The lipid bilayer structure of all cell membranes has a capacitance that has been consistently measured at around 1 microfarad per $cm^2$ [Rall W, 1977]. Axons with their long stretches of cylindrical cell membrane and, for many nerves, their multiple wrappings of Schwann cell membranes (the myelin sheath), comprise large capacitive structures. Since the axons of a nerve represent the parallel conductor described above, the total capacitance is the sum of the individual axonal capacitances. Consequently, resistance within nerves is expected to be minimal compared to other tissues, while the capacitance of nerves is expected to be maximal compared to other tissues. It is believed that the relatively low internal resistance and large capacitance of the axons comprising nerves, compared to other tissues, contribute to the ability to detect nerves according to the present invention.

The inventors have observed that the impedance determined over nerve tissue falls as applied currents increase. This is not likely a direct effect of current level, but is more probably associated with the increased voltage levels required to drive progressively higher currents. These externally applied, increased voltages directly result in increased transmembrane potential differences. The latter cause voltage-gated channels in nerve cell membranes (such as sodium and potassium channels) to cycle into the open position, a situation in which channel conductance rises and resistance falls. Therefore, channel resistance changes are most likely to affect the impedance values as externally applied, voltages increase. Additionally, the large capacitive structure of nerves causes an inverse frequency dependence of the impedance. There is also a displacement current associated with the structure of the protein channel molecule, but it is believed capacitance associated with this displacement current is small compared to the membrane capacitance. Since nerves exhibit electrical characteristics consistent with linear capacitors, nerves can be distinguished from other tissues based upon measurements of applied voltage, applied current, phase, and other electrical properties measured on the skin.

The present invention discriminates tissues, in particular nerve tissues, based upon their differential concentration, distribution, and state (closed, inactive, or open) of voltage-gated channels and upon factors related to the geometry and electrotonic properties of tissues, including the unique geometry (i.e., linear runs and branches) as revealed by the impedance properties of nerves.

Figure 5:
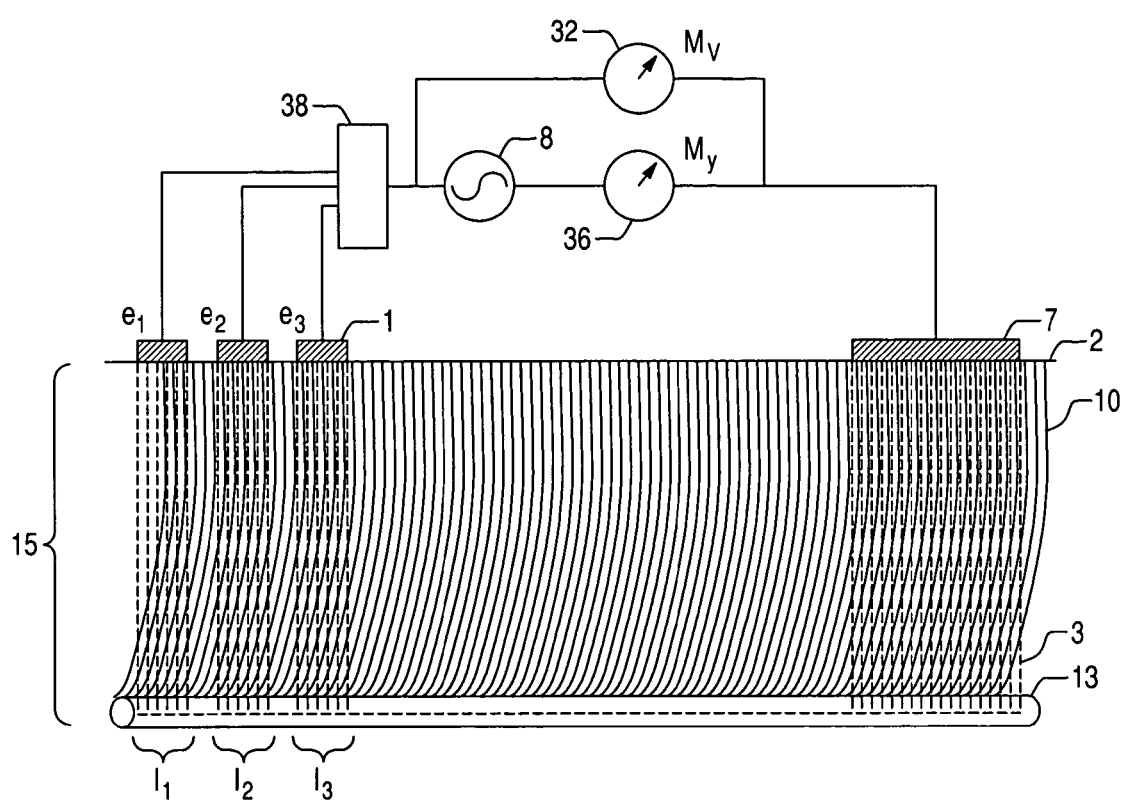
FIG. 5 illustrates a more detailed model of a nerve electrically interacting with a tissue discrimination apparatus according to an embodiment of the present invention.

The classic depiction of current flow through tissue has the current following a curved, prolate ellipsoid (FIGS. 1, 3). The inventors have determined that this model is not correct in the presence of intact, living nerves, i.e., in living tissue. Structures, such as nerve 13, identified at the skin surface 2 by determination of impedance are found at a normal angle to the plane of the skin surface 2 (FIGS. 4, 5). The presence of such structures has been verified through needle electrode studies from depths of 0.5 cm to 8 cm, surgical dissection, transcutaneous stimulation, and needle stimulation. Brush-like, subcutaneous, dermal and epidermal axons 10 that extend from nerve 13 toward the skin surface 2, terminating short of the outer skin surface, may act as conductive pathways and be responsible for this effect as illustrated in FIG. 4. This model and its effect upon electrical potential distribution within tissue are illustrated in FIGS. 4, 5. Referring to FIG. 4, the preferred conductive path presented by axons 10 and nerve tissue 13 results in current 14 preferentially following nerves 13 between electrodes 1 and 7 positioned on skin 2. The classic model suggests that a nerve 13 located in the center of a current spindle should exert more effect on the measured impedance than an equivalent nerve located in the 10% region of the spindle. Further, referring to FIG. 2, this line of reasoning predicts that a nerve located midway on the x-axis between a waveform electrode 1 and a return electrode 7 and lying in the 50% region of the current spindle would cause a greater impedance effect than an equivalent nerve directly beneath the waveform electrode but in the 10% region of the current spindle. However, this concept is not consistent with experimental data. Measurements indicate that preferential conductance pathways 10 from the skin surface 2 are associated with the underlying neuroanatomy and are directed at an approximately normal angle to the skin surface 2, as illustrated in FIGS. 4 and 5.

The inventors have determined that electrical current flows through tissues of a body along preferential paths, in particular along nerves; i.e., living tissue is not only non-homogeneous, it is anisotropic. The preferential pathways presented by nerve tissue comprise a high density collector system in the dermal tissues leading into a long, uninterrupted, conduction pathway that is highly parallel and exhibits a large capacitance relative to non-nerve structures. Associated with this collector and conduction system is a right angle relationship from the skin surface to underlying nerve structures that is most likely a result of the anatomic relationships of nerves to the surrounding tissue. As illustrated in FIGS. 4 and 5, when a voltage is applied across the stratum corneum of the skin surface 2 and the intervening subcutaneous tissue 15 between a waveform electrode 1 and a return electrode 7, current emitted by the waveform electrode 1 may flow down the brush-like structures of the dermal and epidermal axons 10 and then into the nerves 13. Current flows along nerves 13, and then passes back along axons 10 toward the skin surface 2 beneath the return electrode 7, flowing through the stratum corneum to the return electrode 7 in electrical contact with the skin surface. Individual axons are best modeled as leaky, one dimensional cables which maintain the majority of the applied field intra-axonally, but allow some portion of the applied field to transit the surrounding tissue between axons or within a nerve bundle. Though the axoplasm demonstrates a bulk resistivity that is similar in magnitude to that of the extracellular fluid, the interior of axons lacks conduction barriers such as those presented by cell membranes in the surrounding tissue. An applied electrical field may travel in the extracellular fluid medium, but it will encounter these tissue barriers [represented as resistances and capacitances (RC) in series and in parallel] whereas the interior of the axon presents an ohmic resistance without the RC barriers. Furthermore, there is a large capacitance associated with axon structure as a consequence of the long, cylindrical form of the nerve cell. Since the lipid bilayer structure of the cell membrane has a capacitance of approximately 1 $\mu F/cm^2$, the long cylindrical structure of the single axon has a much greater associated capacitance than any other, geometrically discrete, cell type. Additionally, axons travel in bundles as nerves. The result is a highly parallel capacitance and resistance structure where the total resistance is the reciprocal of the sum of the reciprocal individual resistances, and the total capacitance is the sum of the individual capacitances. This means that as the total number of axons within a nerve bundle increases, the total resistance is expected to fall asymptotically while the total capacitance progressively rises. Since impedance is directly related to resistance and inversely related to capacitance, the net result is a large fall in impedance associated with nerve structures. As illustrated in FIG. 5, axon fibers 10 are believed to rise toward the skin from nerves 13 along their length. As a consequence, isocurrent lines 3 should extend between each electrode $e_1 \ldots e_3$ above the nerve 13 as illustrated in FIG. 5. Since the terminal, dermal axons 10 extend toward the skin surface 2 along paths more or less normal to the skin surface, current that passes through axons 10 may reveal the structure of the underlying nerve 13. Consequently, the current or voltage measured across electrodes 1 and 7 in electrical contact with the skin surface 2 can discriminate the underlying nerve 13.

It is believed that a primary physiological phenomenon measured by the present invention is the distribution and density of voltage-gated ion channels, such as sodium channels and potassium channels, in cellular membranes. Nerve, muscle, fat, viscera, tendon, tumor and other types of tissue have different concentrations of voltage-gated channels and therefore are expected to exhibit different levels of impedance allowing discrimination of the different tissues. For example, muscle has a higher density of voltage-gated channels than does fat. Also, non-neural tumors have been reported to lack innervation and consequently are devoid of the low resistance, relatively high capacitance signature of nerves. Thus, it is expected that the present invention will permit tumor tissue to be detected, discriminated from surrounding muscle, fat or viscera, and located based upon the tendency of electric currents to flow around them due to their high impedance.

Observations Related to Electrode Sizing and Applied Signal Parameters

It has been observed that zones of low impedance are exhibited on the skin directly above nerves. It is believed that this is due to the fact that axon fibers 10 preferentially rise from the nerve at approximately right angles to the skin surface. Thus, the low impedance zone due to the preferential conduction path through axon fibers appears just in the zone of the skin that lies directly above the nerve. As such, the presence and location of nerves is revealed by localized zones (typically narrow lines) of low impedance measured on the skin. It has been found that in order to sense the local low impedance associated with an underlying nerve, the sensing electrode (referred to herein as the waveform electrode) must be constrained to a small area, preferably about 10 mm² or smaller. Larger electrodes, such as standard electrocardiogram (ECG) electrodes which are typically circular with diameters of 1.5 cm or square with sides of 1.5 cm, and thus range in area from about 1.8 cm² to about 2.25 cm² (i.e., 180-225 mm²), electrically couple with the skin over areas much larger than the width of low impedance zones that lie above nerves, and thus measure average electrical characteristics of the skin (e.g., impedance) which obscure the low impedance of an underlying nerve. For similar reasons, the system according to the present invention employs a relatively large return electrode so impedance differences can be localized to conditions at the waveform electrode.

It is accepted in the electrode literature that impedance measurements performed with skin surface electrodes are pressure sensitive (see, e.g., Edelberg R: Electrical Properties of Skin, Biophysical Properties of the Skin. Edited by Elden H R, Wiley-Interscience, 1972, pp. 513-50). However, these observations are based on studies in which the interface medium (i.e., electrode) geometry was that of a standard ECG electrode, and not constrained to the small area of the waveform electrodes of the present invention. It is known that the resistance of an electrolyte is dependent on the length and cross-sectional area of the electrolyte according to:

$$R = \rho L/A;$$

where:
R=resistance;
$\rho$=resistivity of the electrolyte;
L=length of the electrical field path through the electrolyte; and
A=cross-sectional area of the electrolyte.

From this equation it can be seen that when pressure is applied to a deformable electrode in contact with skin where the interface medium has a large geometry (i.e., not constrained as per embodiments of the present invention) the pressure will result in a decrease in the path length through the electrolyte L and an increase in the cross sectional area of the electrolyte A, leading to a decrease in resistance R. However, if the interface medium is placed in a non-deformable enclosure, i.e., a plastic cylinder with the electrode at one end, the pressure sensitivity of impedance determinations can be eliminated. This has been demonstrated using the present invention.

Figure 14:
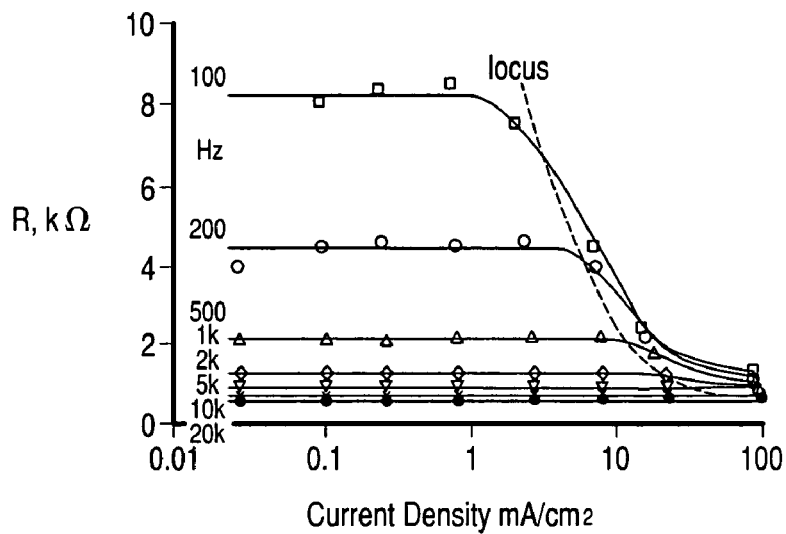
FIG. 14 presents resistance data measured across electrodes in saline as a function of current density, assuming a parallel RC equivalent circuit model.
Figure 15:
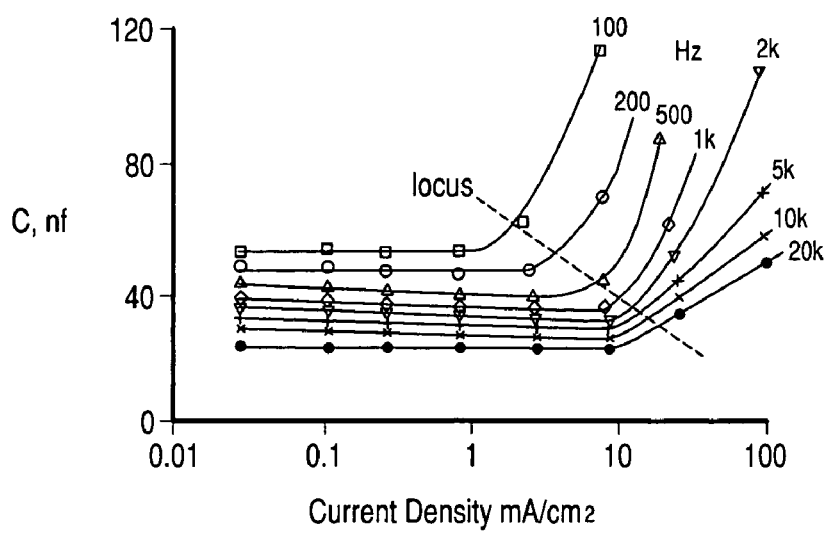
FIG. 15 presents capacitance data measured across electrodes in saline as a function of current density, assuming a parallel RC equivalent circuit model.
Figure 16:
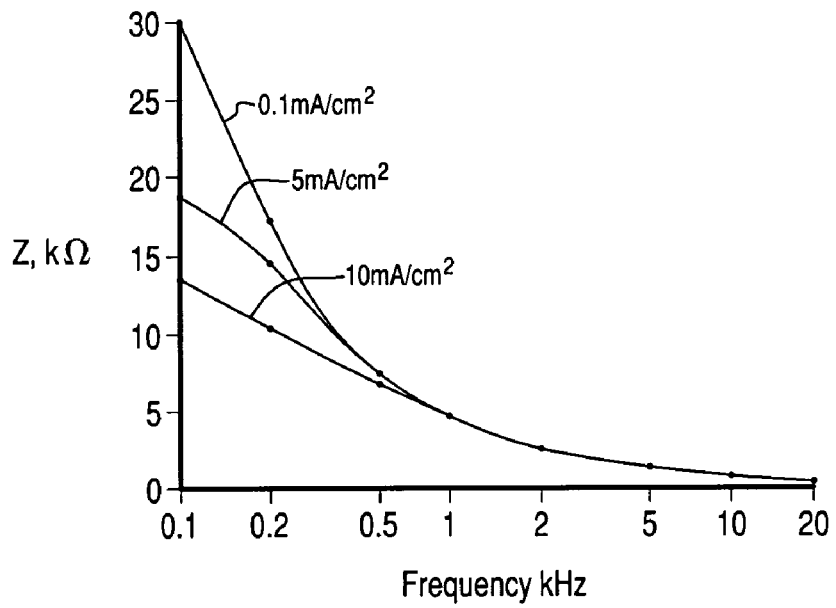
FIG. 16 presents impedance calculated from data measured across electrodes in saline as a function of signal frequency, assuming a parallel RC equivalent circuit model.
Figure 17:
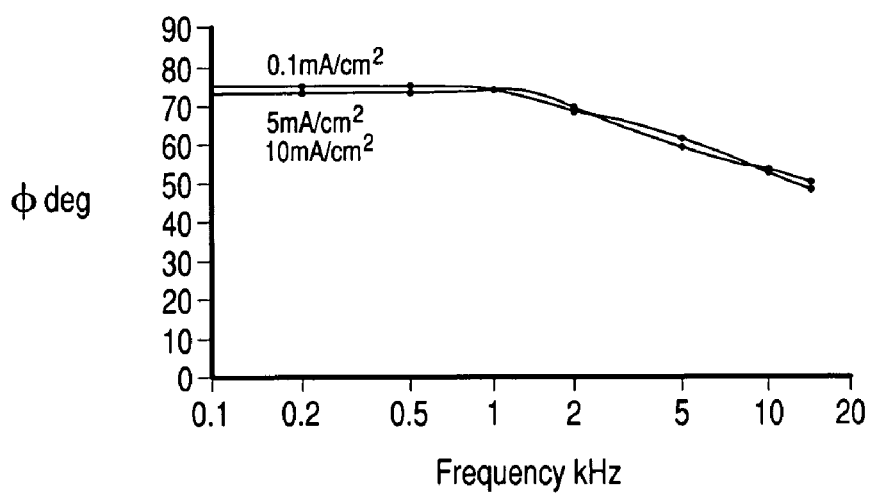
FIG. 17 presents phase angle data measured across electrodes in saline as a function of signal frequency, assuming a parallel RC equivalent circuit model.

Another factor to be considered in tissue discrimination according to the present invention is the effect of current density through the electrodes. This is because the resistance and capacitance of electrodes are affected by the current density. It has been reported that the current density and frequency dependencies of both the resistive and capacitive components of the impedance are observed from electrodes. See Geddes L A: Historical Evolution of Circuit Models for the Electrode-Electrolyte Interface. Ann Biomed Eng 1997; 25: 1-14. These effects are illustrated in FIGS. 14-17 which reflect data reported by Geddes. FIGS. 14 and 15 show the manner in which resistance (FIG. 14) and capacitance (FIG. 15) vary with increasing current density at different frequencies for a platinum/0.9% saline interface. As can be seen in FIGS. 14 and 15, relationships between current density and electrical characteristics (i.e., resistance v. current density shown FIG. 14 and capacitance v. current density shown in FIG. 15) become nonlinear as the current density increases and as the signal frequency increases. FIG. 16 shows the manner in which impedance varies with signal frequency for three current densities, while FIG. 17 shows how phase shift varies with signal frequency for the same current densities. As can be seen in FIGS. 16 and 17, the relationships between frequency and electrical characteristics (i.e., impedance v.

frequency shown in FIG. 16 and phase angle v. frequency shown in FIG. 17) exhibit inflection regions at a specific frequency. These relationships suggest that in order to maintain stable electrode impedance for skin surface measurements, the current density should be kept within the linear ranges for signal frequency and current density. A suitable range of frequencies for use in various embodiments of the present invention is from approximately 500 Hz to approximately 10 KHz, more preferably from approximately 1 kHz to approximately 2 kHz. A suitable range of current densities for use in various embodiments of the present invention are from a minimally achievable level approximately 10 mA/cm$^2$, more preferably from approximately 0.2 mA/cm$^2$ to approximately 10 mA/cm$^2$.

Figure 18:
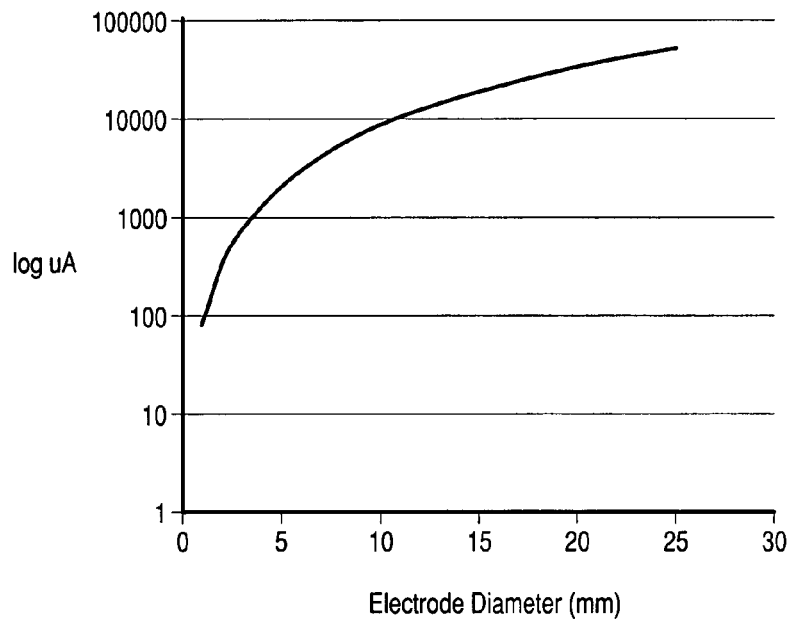
FIG. 18 presents current data measured across electrodes in saline as a function of electrode diameter, assuming a parallel RC equivalent circuit model and fixed current density.

The aforementioned phenomena need to be considered in setting the electrode size and the various parameters of the applied waveform signal in the present invention. As noted above, the use of small electrodes enables various embodiments of the present invention to measure the localized differences in impedance on skin associated with tissue structures like nerves. For any particular applied current, the smaller the electrode is, the greater the current density. This is illustrated in FIG. 18, which plots the maximum current in microamps against the electrode diameter in millimeters for a controlled applied current density of 10 mA/cm$^2$, which is a suitable upper limit for current density according to various embodiments of the present invention. FIG. 18 reveals an inflection point in the region of approximately 5 mm diameter electrodes. Balancing the various phenomena against the aim of detecting localized impedance differences leads to a suitable range for the diameter of electrodes used with various embodiments of the present invention of between approximately 1 mm and approximately 6 mm, more preferably between approximately 2 mm and approximately 5 mm, and even more preferably approximately 3 mm in diameter. Such electrodes have an area of approximately 10 mm$^2$ or less.

This selection of the electrode size impacts the current that may be applied to the electrodes, since as the electrode size decreases the current density increases for a given current. By way of example but not by way of limitation, an electrode approximately 3 mm in diameter has an area of approximately 7.1 mm$^2$. Referring to FIGS. 14 and 15, from studies of platinum electrodes in saline, it can be seen that currents above approximately 600 microamps ($\mu$A) flowing through an electrode of 7.1 mm$^2$ (i.e., 600 $\mu$A/7.1 mm$^2$=8.4 mA/cm$^2$) lie in the flat, linear portions of the resistance/capacitance versus current density curves for frequencies above 500 Hz. On the other hand, it has been found that a practical minimum in the applied current will be set by the system electronics, below which it is difficult to discriminate differences in electrical characteristics. An example of such a minimum current is approximately 10 $\mu$A, although it is specifically noted that improvements in electronics technology will allow this lower current limit to be decreased, and therefore this value is identified here for the sake of example only. Thus, a suitable range of currents for various embodiments of the present invention extends between approximately 10 $\mu$A and approximately 600 $\mu$A, more preferably between approximately 10 $\mu$A and 400 $\mu$A and even more preferably between 10 $\mu$A and 100 $\mu$A.

Electrodes may be of any construction known in the art as well as disclosed in the present invention. Electrodes may be made of metal, metal:metal salt combination, conductive polymer or an assembly of materials such as more fully described herein. Electrodes may be applied directly to the skin of a subject, i.e., dry, or in combination with a coupling interface material as more fully described herein.

Figure 39:
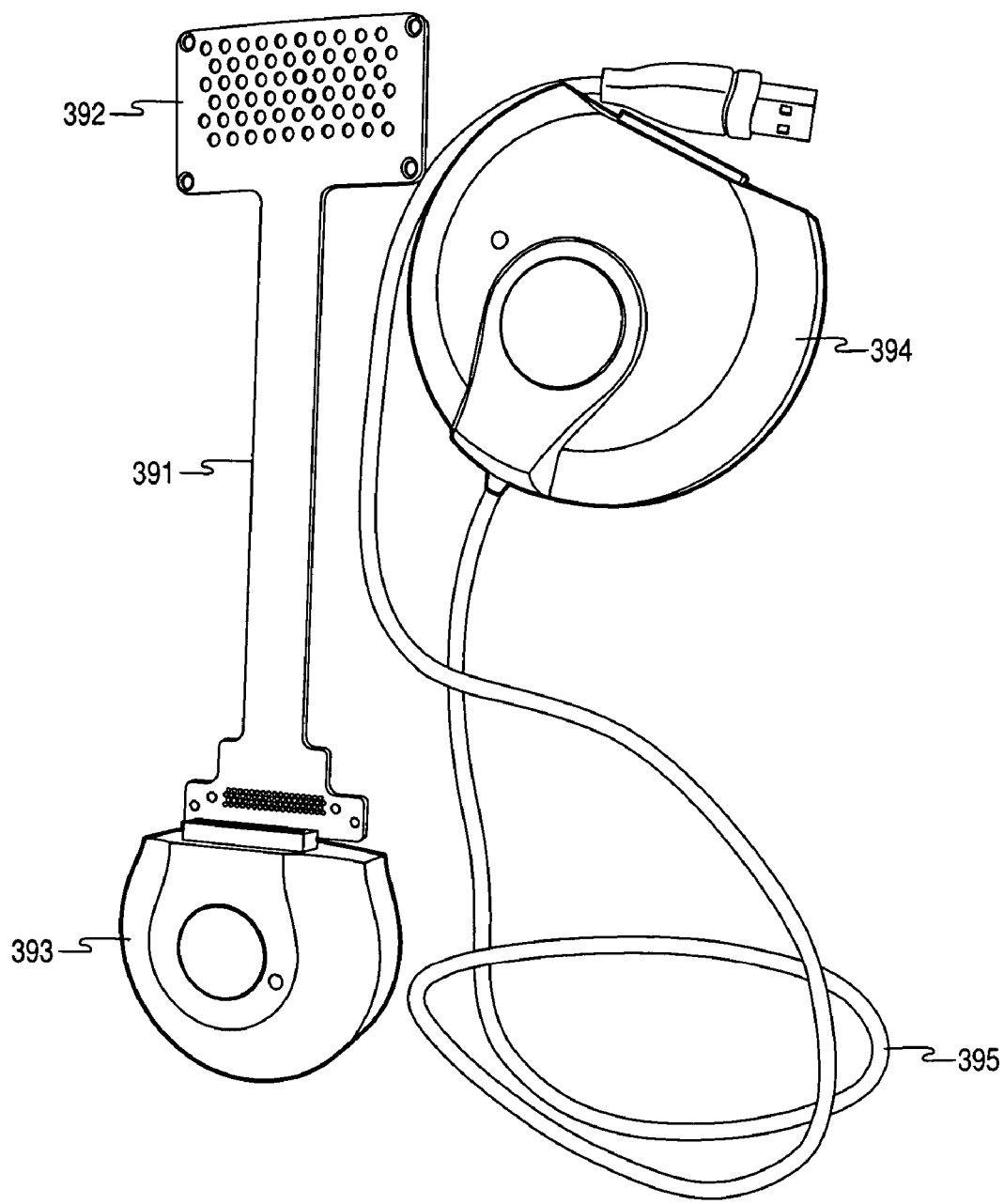
FIG. 39 is a photograph of an example of a wireless sensor system according to an embodiment of the present invention.
Figure 40:
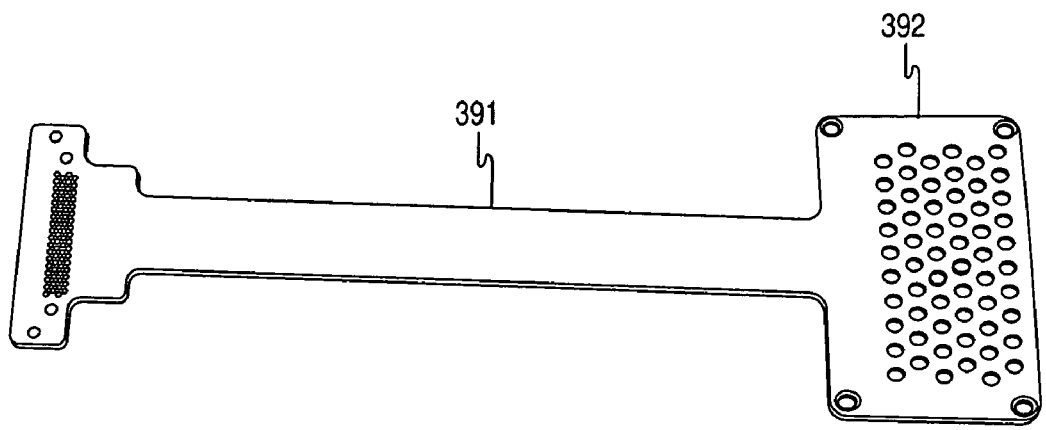
FIG. 40 is a photograph of an example of an electrode array assembly according to an embodiment of the present invention.

Waveform electrodes may be provided in the form of an electrode array assembly which may comprise multiple rows of multiple electrodes, e.g., 6 rows of 10 electrodes each as in the embodiment shown in FIGS. 39 and 40. As described in U.S. Pat. Nos. 6,564,079 and 6,609,018, a suitable electrode array assembly comprises a number of parts which perform different complementary functions when assembled together. As described in more detail herein, electrodes should be constrained in area to be able to detect localized electrical characteristic differences, and include a suitable coupling interface material (e.g., an electrolyte gel) to ensure good electrical contact with the skin. Additionally, the electrodes need to be insulated one from another and be connected to a signal generator and/or sensor circuits. Further, the assembly should be flexible and include connectors to facilitate connecting the assembly to system equipment. An example of a suitable electrode array assembly is illustrated in FIGS. 39 and 40. Thus, a suitable electrode array assembly will include electrodes configured as wells that can contain the coupling interface material for providing an electrical connection to the skin of a subject. When the constituent parts are assembled, the assembly may comprise an array of wells where each well is capped with an electrode, e.g., a gold or silver disk, and surrounded by a wall of insulating material formed by aligning an insulating layer with an array of through holes with an array of electrodes so that each cap electrode fits into a single well. Each cap electrode is electrically connected to a conductor, e.g., by means of a conducting metal paste, and the conductors are connected to an electrical coupling, such as a ribbon cable which can be coupled to a controller. A return electrode 7 is also configured to be electrically connected to the skin of a subject and located a distance (e.g., about 20 cm.) away from the electrode array assembly.

Figure 25:
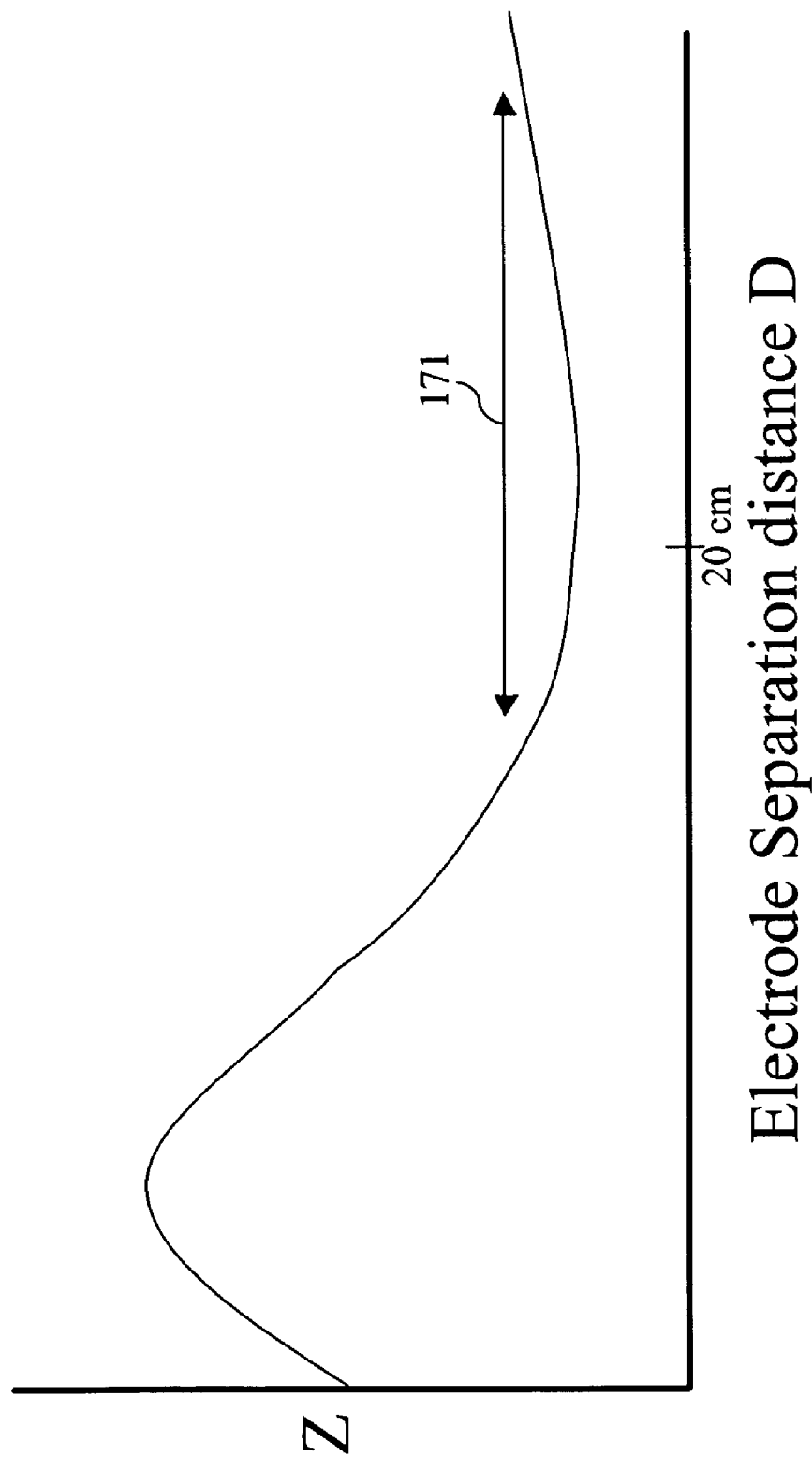
FIG. 25 illustrates the relationship between impedance Z and electrode separation distance D for a fixed frequency of an applied electrical field that may be observed using an embodiment of the present invention.

The inventors have discovered that, for a given set of measurement conditions, a distance exists between the waveform electrode 1 and the return electrode 7 over which impedance is at a minimum and nerves 13 may be discriminated by observing changes in impedance with waveform electrode 1 and return electrode 7 at such spacing. An example of this observation is illustrated in FIG. 25. As can be seen in FIG. 25, over short separation distances, the calculated impedance rises to a maximum. Beyond the maximum, the impedance declines asymptotically toward a non-zero minimum value and then trends upwards approximately linearly. Observations have determined that better (e.g., more revealing) nerve identification is obtained with separation distances in the tail region 171 of this Z vs. D curve. For example, about 20 cm is a workable separation distance. In the tail region 171, the rate of change of impedance with distance is lower, so that reducing the difference between the first and last rows in the array has less effect than at shorter separation distances. The optimum separation distance may vary based upon the individual, the body portion being examined, etc. For example, for pediatric subjects, the optimum separation distance may be different than for adult subjects. Thus, a method of applying electrodes to a subject may involve varying the placement of the return electrode on the subject to determine a near optimum electrode separation distance, ensuring that the electrode is located beyond the impedance peak on the Z vs. D curve. Accordingly, the various embodiments of the present invention may include structures or procedures for placing the waveform electrode 1 and return electrode 7 at a proper distance to facilitate obtaining better data. For example, the waveform electrode 1 and return electrode 7 may be positioned in the range approximately 20 cm apart.

System Overview

Figure 6:
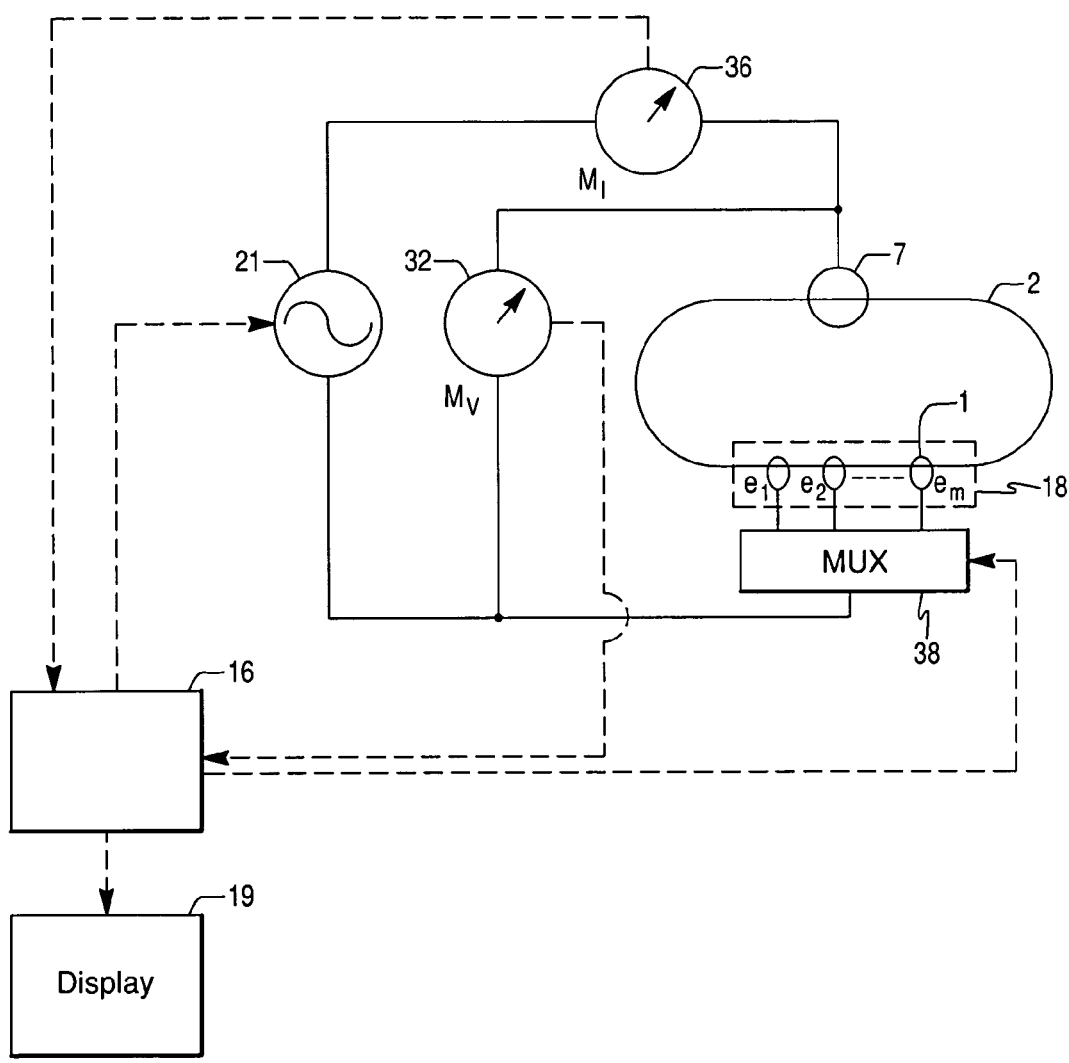
FIG. 6 illustrates a system block diagram of an embodiment of the present invention.

A system for scanning nerves and assessing nerve function is illustrated in FIG. 6. The basic system includes: a controller 16, such as a microcomputer, microcontroller or microprocessor, that is configured to control the generation of electrical signals, measure characteristics of signals, store data, and perform analysis of the data; a waveform generator 21, an electrical property measuring sensor (e.g., voltage meter 32 and/or current sensor 36); one or more waveform electrodes 1; and a return electrode 7. The waveform electrode 1 may be a plurality of waveform electrodes $e_1 \ldots e_m$, e.g., configured in the form of an electrode array assembly 18, to which the signal generator 21 is attached. Waveform electrodes 1 are preferably about 10 mm$^2$ in area or smaller in order to permit them to measure localized variations in impedance. In an embodiment, a multiplexer switch 38 may be used to switch the waveform signals to specific waveform electrodes 1 applied to the skin 2 of a subject. Return electrode 7 is also applied to the skin 2, and connected to the controller. A sensor is connected across waveform electrodes 1 and return electrode 7. The sensor may be any of a number of electrical signal sensors known in the art, such as a voltage measuring device 32 and/or a current measuring device 36. The sensor provides measurement data signals to the controller 16 for analysis. In alternative embodiments, the waveform electrode 1 may be a single electrode, while the return electrode 7 may be one of an electrode array assembly. The system will generally also include a display 19 coupled to and configured to receive display signals from the controller 16 and to generate a visual display of results, e.g., data displays in configurations that enable a user to detect or locate the presence of nerves within the subject.

Figure 7:
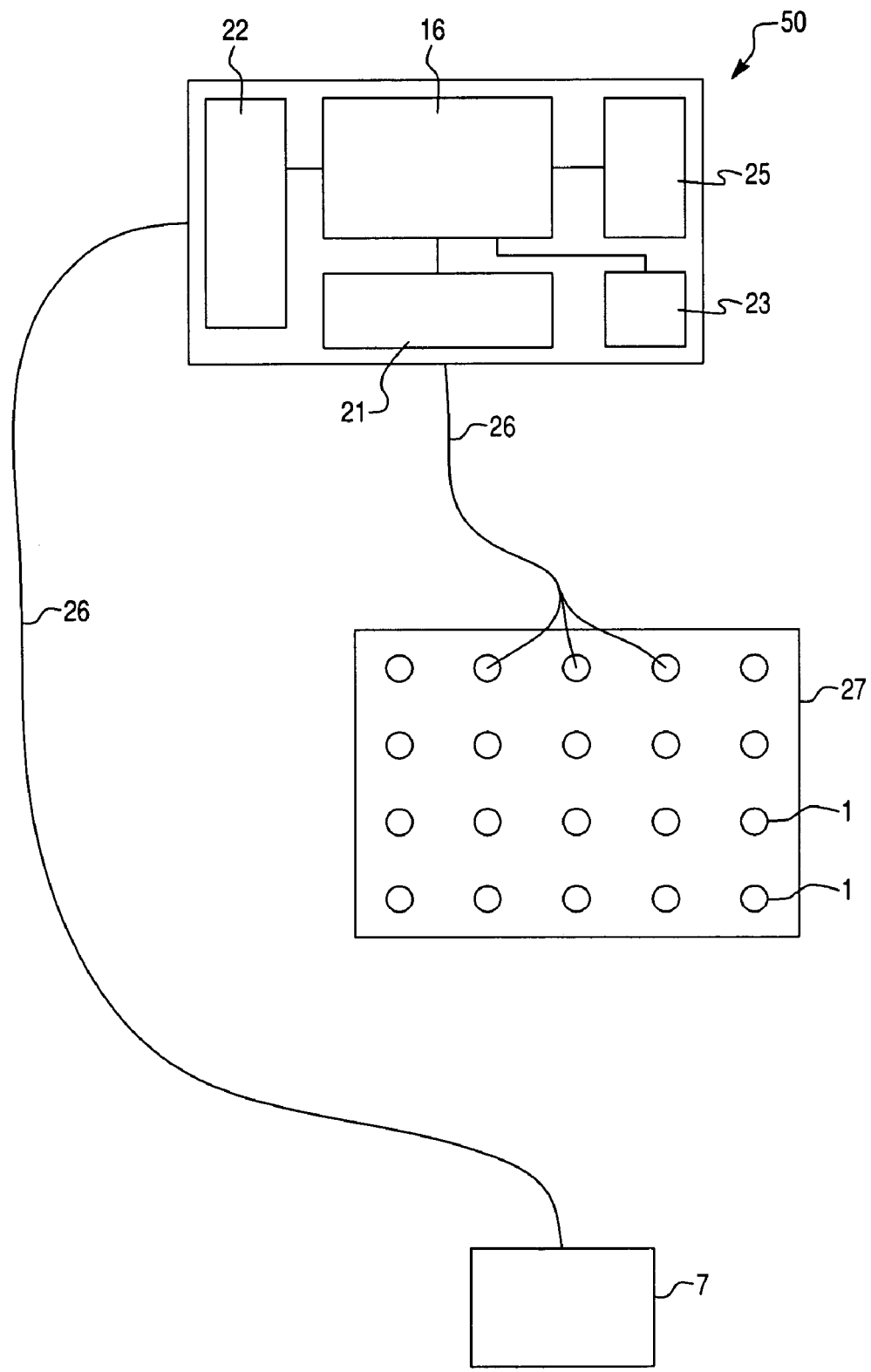
FIG. 7 illustrates a system for discriminating tissues according to an embodiment of the present invention.

In various embodiments, the components making up the controller, signal generator and sensors may be integrated into a single equipment package 50 connected to the electrodes, such as illustrated in FIG. 7. Such an integrated package 50 may include the controller 16 which itself may include a microprocessor, signal generator 21, amplifier circuitry 22 for amplifying the signal, power supply 23, memory modules 25, and cabling 26, which may be any form of electrical conductor or electrical leads of a size and form suitable for connecting the waveform electrode 1 and return electrode 7 to the controller 16 or other circuitry. In some embodiments described more fully herein with reference to FIG. 29, the controller may be a separate control unit 210 coupled to the signal generator assembly 211 by means of a wireless datalink transceiver 28 providing a wireless datalink 212 to a compatible transceiver 29. Cabling 26 may be coupled to circuitry by cable connectors 30 that permit the electrodes to be quickly connected. Cabling 26 may be one or more individual wires, one or more twisted wire pairs, a ribbon cable, or one or more coaxial cables as are well known in the electronic arts and are suitable for conducting microprocessor 20 electrical signals measured across the waveform electrode 1 or electrode array assembly 27 and the return electrode 7.

Referring to FIG. 6, the display 19 may be any form of electronic display known in the art or that will be developed in the future. Examples of suitable displays contemplated within the present invention include a computer screen; a cathode ray tube (CRT); liquid crystal display (LCD); plasma display; arrays of light emitters, e.g., light emitting diodes (LED); and combinations or variations of these example displays.

The controller 16 may be any electronic processing device capable of processing software instructions, receiving data inputs and providing data and command outputs. Examples of suitable processors contemplated within the present invention for uses as a controller include a microprocessor 20, microcomputer, and microcontroller, as well as external processors/computers, including a personal computer, laptop computer 226 (FIG. 30); work station; handheld computer, e.g., a personal data assistant; and combinations or variations of these example processors. A controller 16 or microprocessor 20 typically will include or be coupled to electronic memory 25 suitable for storing software instructions and data, including volatile and nonvolatile memory as are well known in the art. Data stored in the memory 25 will typically include the data recorded during operation of the system, and processed data representing tissue discrimination information. The memory 25 may also store data that are useful for operating the system and conducting analysis on measurement data. Data that are useful to an operator for operating the system may include operating instructions, user manuals, trouble-shooting guidance, medical diagnostic guidance, and image interpretation guidance. Such operator-useful information may be stored in the form of a database to provide ready access to a user operating the system. While the operator-useful information may be stored in memory on or near the device (e.g., a hard drive or compact disc reader), it may also be connected to the controller 20 via a network, e.g., the Internet, by suitable communications electronics as more fully described herein.

The test subject may be any tissue, including an external body part such as an arm, or an internal organ of a being. Test subjects (e.g., a human or animal) typically contain at least one electrically responsive membrane system comprising a lipid bi-layer containing embedded protein molecules, some of which are ion channels.

While the aforementioned embodiments employ a digital processor to receive and process sensed electrical parameters to determine the desired electrical characteristic, such as impedance, the present invention contemplates the use of analog circuit components to accomplish the same functions. For example, while the signal processing algorithms described herein employ digital sampling and curve fitting algorithms, the same functions may be accomplished by a synchronous demodulator such as employing a phased locked loop circuit element. Thus, the present invention is not intended to be limited to the digital components and system described in the example embodiments described herein.

Parameters Measurable By The System

Basic operation of the system that is the subject of the present invention comprises placing electrodes in electrical contact with the skin of a subject and applying a controlled current or voltage waveform, and measuring the voltage or current waveform through the tissue from the same electrodes, from which electrical characteristics or properties of the tissue, such as impedance, may be calculated. If a controlled current waveform is applied to the system, the voltage waveform across the electrodes and the intervening tissue may be measured. Conversely, when a controlled voltage waveform is applied to the system, the current waveform flowing through the electrodes and the underlying tissue may be determined. From these measurements, other electrical characteristics such as impedance may be calculated. As is well known in the art, electrodes may be placed in electrical contact with skin by placing the electrode in physical contact with the skin, preferably with a coupling interface material 31, e.g., a hydrophilic, silver-silver chloride gel. Measuring the waveform across the electrode—tissue system provides information on the electrical characteristics (e.g., impedance or admittance) of tissue between the waveform electrode 1 and return electrode 7. The time varying nature of the current and voltage waveforms provides additional information, e.g., the phase shift, as will be discussed more fully below.

In an embodiment, a controlled current waveform is applied between waveform electrode 1 and return electrode 7, while the resultant voltage waveform is measured across waveform electrode 1 and the return electrode 7. A controlled current waveform is maintained by adjusting the voltage waveform across waveform electrode 1 and return electrode 7 sufficient to maintain a desired current. In an alternative embodiment, a controlled voltage waveform is applied across waveform electrode 1 and return electrode 7 and the resultant current waveform determined. In various embodiments, the system may not detect current directly. Rather, the voltage drop across the known resistance may be determined from which the current can be derived. Similarly, field detection methods could be used to indirectly measure current. In various embodiments, the electrical property measured may be voltage drop across the tissue. In the controlled current mode, the current waveform parameters are selected by the controller 16 and the voltage waveform required to drive that selected current through the load (circuit, electrodes, and tissue) is detected.

The ranges of controlled currents and controlled voltages that may be applied are limited by safety concerns, but may include the following. The voltage across the waveform electrode 1 and return electrode 7 may be from minimally achievable to approximately 24 volts (V), more preferably between minimally achievable and approximately 5 V. As discussed above and depending upon the electrode size, when operating in controlled current mode, the current waveform applied between the waveform electrode 1 and return electrode 7 may be between approximately 10 microamps (μA) and approximately 600 μA, more preferably between approximately 10 μA and approximately 100 μA. Similarly, in the controlled voltage mode, the maximal current that is permitted to pass through tissues will be limited to between approximately 10 HA and approximately 600 μA, more preferably between approximately 10 μA and approximately 100 μA. The amplitude of the applied signal will range from minimally achievable to approximately 24 V, more preferably between minimally achievable and approximately 5 V in the controlled current mode, and from approximately 10 μA and approximately 600 μA, more preferably between approximately 10 μA and approximately 100 μA in the controlled voltage mode.

The waveform of the applied signal may be any wave shape, and more preferably may be either of a monophasic or a biphasic sinusoidal or square wave form. The waveform may be a sinusoidal wave, a rectangular wave, some other periodic wave, a constant non-zero amplitude waveform, a single impulse, some other aperiodic waveform, or some additive combination thereof. One preferred waveform (herein called a monophasic sinusoidal waveform) is the combination of a sinusoidal waveform plus a constant offset level resulting in entirely non-negative current or voltage amplitudes throughout the waveform. The frequency of a time-varying applied signal may range from approximately 1 hertz (Hz) to approximately 10 kHz, more preferably between approximately 0.5 kHz and approximately 2.5 kHz, and even more preferably between approximately 1.5 kHz and approximately 2 kHz.

In the controlled current mode, measurements of the voltage waveform may be made immediately upon applying the current waveform, after approximately 100 cycles (or more), or at any time in between, more preferably after approximately 20 cycles. In the controlled voltage mode, measurements of the current waveform may be made immediately upon applying the voltage waveform, after approximately 100 cycles (or more), or at any time in between, and more preferably after approximately two to approximately five cycles. While measuring a waveform, between 1 and approximately 500 samples may be taken per cycle of the waveform, and more preferably between approximately 20 and approximately 50 samples per cycle of the waveform. Measurement durations may range from approximately $10^{-5}$ seconds to approximately 1 second per each electrode, and more preferably for approximately 0.01 seconds per each electrode. In an embodiment, there is a single, large, return electrode 7, and a plurality of waveform electrodes 1 are fashioned in the form of an array. The distance or spacing on the skin 2 between the waveform electrode 1 and the return electrode 7 may range between as short a separation as is achievable to as large a separation as is achievable, and more preferably approximately 20 cm.

In an embodiment, a single electrode may serve as the waveform electrode 1, and a plurality of return electrodes 7 may be fashioned in the form of an array, such as disclosed in U.S. Pat. Nos. 6,564,079 and 6,609,018 which are hereby incorporated by reference. An example of an electrode array assembly according to the present invention is provided in FIGS. 39 and 40.

Figure 8:
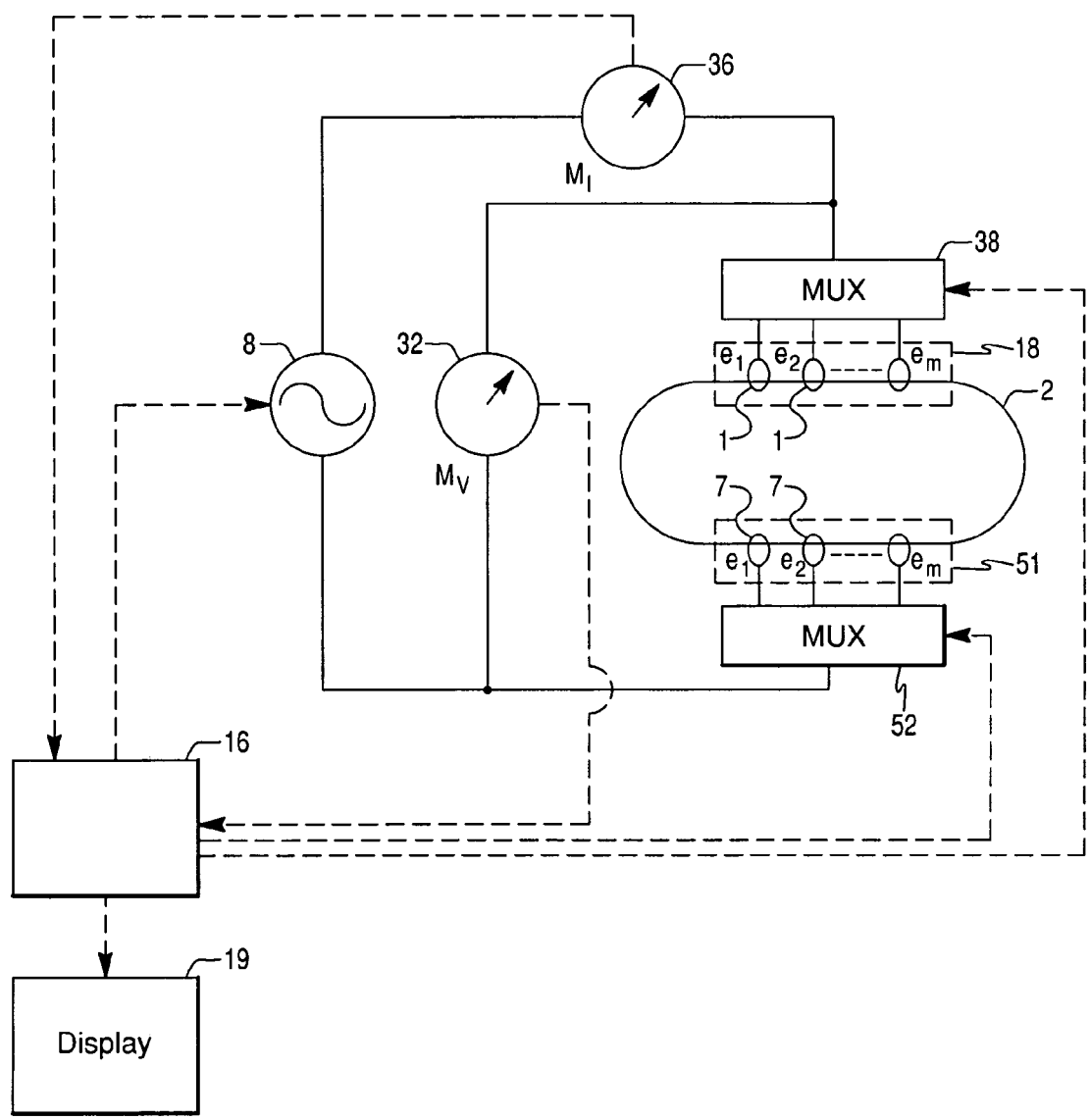
FIG. 8 illustrates a system block diagram of an alternative embodiment of the present invention.

In an embodiment illustrated in FIG. 8, the waveform electrodes 1 and return electrodes 7 may both be fashioned in electrode array assemblies 18, 51, e.g., complementary arrays. In this embodiment, another multiplexer circuit 52 may be connected to the return electrode array 51. An advantage of complementary arrays for waveform electrodes 1 and return electrodes 7 is that the linear inter-electrode separation on the skin surface 2 may be maintained at an optimum distance more precisely by using a return electrode 7 at the proper distance from each waveform electrode. A design consideration associated with using return electrodes 7 in the form of a return electrode array assembly 51 concerns the diameter of the return electrodes 7. Return electrodes 7 should contact a large enough area of the skin surface 2 to integrate the underlying impedance characteristics of the skin. Small return electrodes 7 may result in the underlying impedance characteristics not being integrated, and consequently being measured as lower than would be measured with a larger skin surface contact electrode. Thus, small return electrodes 7 may lead to a situation where a relatively high impedance site may be beneath the waveform electrode 1 and relatively low impedance site beneath the return electrode 7, but there may be no mechanism to determine which of the two electrodes was actually overlying the low impedance site. This design concern may be addressed by using an array 51 of larger return electrodes 7. Alternatively, all electrodes in the return electrode array assembly 51 may be sensed to obtain the effectiveness of a single large electrode followed by sensing of a single return electrode 7 within the array 51, with the processor comparing measurements to determine the underlying impedance characteristics of skin beneath the waveform electrodes 1 and return electrodes 7.

In an embodiment, the controller 16 provides instructions to the waveform generator 21 to control the amplitude, shape and duration of the applied waveform. The controller 16 may also send control signals to the multiplexer switching device 38 to provide the generated waveform to a selected waveform electrode 1 for a predefined period of time (a sampling period). Thus, the duration of the applied waveform may be controlled by the microprocessor via the multiplexer switching device 38 or via the waveform generator 21. In an embodiment, the controller 16 may direct the waveform generator 21 to produce waveforms of a specified amplitude, frequency, and/or shape, e.g., generating a pulsed train or square waveform, a sinusoidal waveform, a sawtooth waveform, etc. Alternatively, the controller 16 may instruct the waveform generator 21, perhaps in conjunction with the multiplexer switching device 38, to apply a plurality of different waveforms, each waveform being applied within a sampling time, to an individual waveform electrode prior to switching to another waveform electrode. Complex waveforms, comprising two or more waveforms of different shape and/or frequency, may also be applied in various embodiments of the present invention.

The multiplexer switching device 38 may be an electronically controlled switch, a multiplexer, a gate array, or any suitable device that may be controlled by the controller 16 to provide current waveforms or voltage waveforms from the waveform generator 21 across selected, individual electrodes within the waveform electrode array assembly 18 and one or more of the return electrodes 7 in the return electrode array assembly 51. In an embodiment, the switching device 38 may be controlled by the controller 16 to apply the generated waveform to a single waveform electrode, to a selected set of electrodes or to all of the waveform electrodes in the array assembly 18 simultaneously. The waveform generator 21 may also be controlled by the controller 16 in association with the switching device 38 to apply the same current to a plurality of waveform electrodes or all of the waveform electrodes independently of each other simultaneously, even when the waveform electrodes experience or exhibit different impedances. The waveform generator 21 and the switching device 38 may also be controlled by the controller 16 to apply a single current waveform or voltage waveform to all of the waveform electrodes or a plurality of waveform electrodes of the waveform electrode array assembly so that the single current waveform or voltage waveform is dispersed among the selected waveform electrodes. Using software executed by the controller to control the waveform, the applied current waveform or voltage waveform can be varied at an individual waveform electrode 1 within the array of waveform electrodes 18, either during one sampling window or after sampling across other electrodes in the array or in a sequential manner.

In an embodiment, the controller 16 is programmed with software that allows the controller 16 to receive commands from an operator to define the parameters of the waveform, e.g., the shape of the waveform, the positive and negative peak amplitudes, the frequency and the duty cycle. The controller 16 may also contain a memory having stored thereon a plurality of predefined waveforms and may select waveforms to be generated by the waveform generator from the predefined set of waveforms. The waveforms may vary in a number of parameters, including for example bias, positive peak amplitude, minimal amplitude, negative peak amplitude, frequency, shape, and/or duty cycle. Controller 16 may alternatively be configured to receive commands from another controller (e.g., a personal computer 226) electronically connected to the controller 16, e.g., by a digital datalink as known in the art (e.g., Fire Wire, USB, serial or parallel interface, etc.), or by means of a wireless datalink transceiver providing a wireless datalink as known in the art (e.g., infrared data (IrDA) serial link, IEEE 802.11 g, Bluetooth, or similar wireless datalink technology as exists or will be developed in the future), embodiments for which are more fully described herein.

The controller 16 may generate the waveform. Alternatively, a waveform generator circuit may be included, as is known in the art that is controlled by the controller 16 to generate the desired waveform at the desired amplitude (e.g., voltage or current), shape, frequency, duty cycle, etc. An amplifier or array of amplifiers may be provided between the controller 16 and the waveform generator circuit to boost the signal (e.g., voltage or current) to the desired value, which may be controlled by the controller 16.

In operation, the return electrode 7 completes an electrical circuit through the tissue with electrodes in the waveform electrode array assembly 18. In an embodiment illustrated in FIG. 6, the controller 16 receives a signal from a sensor 36 or 32, which may be current or voltage, measured across the waveform electrode array assembly 18 and the return electrode 7 during the sampling time (sometimes referred to herein as the sampling window). The controller 16 may then calculate and store information derived from the measured signal, e.g., impedance, resistance, reactance, admittance, conductance, and other electrical parameters determinable from a plurality of samples or sampling periods, and based upon a plurality of different waveforms applied across the waveform electrodes 1 and return electrode 7. In an embodiment, the controller 16 receives information from the sensors 36 or 32, through the switching device 38 relating to the current waveform and the voltage waveform measured across each waveform electrode 1 and the return electrode 7. The controller 16 may use the current waveform and/or the voltage waveform determined across each waveform electrode 1 and the return electrode 7 to calculate the impedance between each waveform electrode 1 and the return electrode 7. The controller 16 may include or be connected, either directly or indirectly, to data storage device or capability, e.g., a random access memory (RAM), or a recordable magnetic, optical, or magneto-optical disk device, or a tape storage device. Preferably, the data storage device or capability includes a database (e.g., data tables accessible via database software) for storing data in a machine-useable format. The controller 16 may store data indicative of the current waveform, the voltage waveform, and the calculated impedance across each waveform electrode 1 and the return electrode 7 and for each sampling period. Alternatively, the controller 16 may pass data directly to an external controller connected thereto. An external controller may then perform the data processing and recording.

Sampling of signals across the electrodes may be continuous, intermittent or periodic. If continuous, it may be detected as a digital signal, e.g., via an analog-to-digital (A/D) converter that converts the received analog signal (e.g., voltage or current) into a digital value by integrating the signal over brief sampling windows as is well known in the art.

When admittance Y is determined for all the electrodes in the array, those electrodes demonstrating the largest Y will most likely predict the course of a neuroanatomic structure, e.g., a nerve or nerve branch point, underlying those electrodes. If desired, the resistive and reactive components of Y may be derived. Those electrodes demonstrating the lowest resistance R or highest capacitance C will most likely predict the course of a neuroanatomic structure. Other, derivative functions of current I, voltage V, or impedance Z related to frequency, time, or distance may also be used to indicate the position of neuroanatomic structures.

Another embodiment of the apparatus of the invention is similar to the embodiments illustrated in FIGS. 6 and 7 except that a return electrode array assembly 51 is used and a single waveform electrode 1 is used (i.e., the polarity of the waveform signal is switched). As illustrated in FIG. 6, controller 16 provides instructions to waveform generator 21 to provide a waveform across the waveform electrode (7 in this embodiment) and the return electrode array assembly (18 in this embodiment) containing a plurality of return electrodes $e_1$ through $e_m$ which selectively complete an electrical circuit through the tissue with the waveform electrode when selected by a return electrode switching device (38 in this embodiment) to provide a signal to the controller 16. The impedance of various tissues beneath the skin 2 may be determined in the same manner as described in connection with other embodiments of the present invention, except that the current and voltage waveforms may be determined utilizing the return electrodes as waveform electrodes to allow for a more convenient broad area of coverage by the plurality of return electrodes. In order to address the design consideration associated with the use of small area return electrodes, the electrodes in the array may be made sufficiently large to integrate underlying skin impedance characteristics. Alternatively, all electrodes in the return electrode array assembly may be sensed to obtain the impedance integrating effectiveness of a single large electrode followed by sensing of a single return electrode, with the processor comparing measurements to determine the underlying impedance characteristics of tissue beneath the waveform and return electrodes. The methods of operating the apparatus illustrated in FIGS. 10-13 are equally applicable to this embodiment, except that the return electrodes are selected.

The characteristics of the signals that may be obtained from various embodiments of the present invention may be understood by considering the RC circuit characteristics of tissues, particularly nerve tissues.

Figure 10:
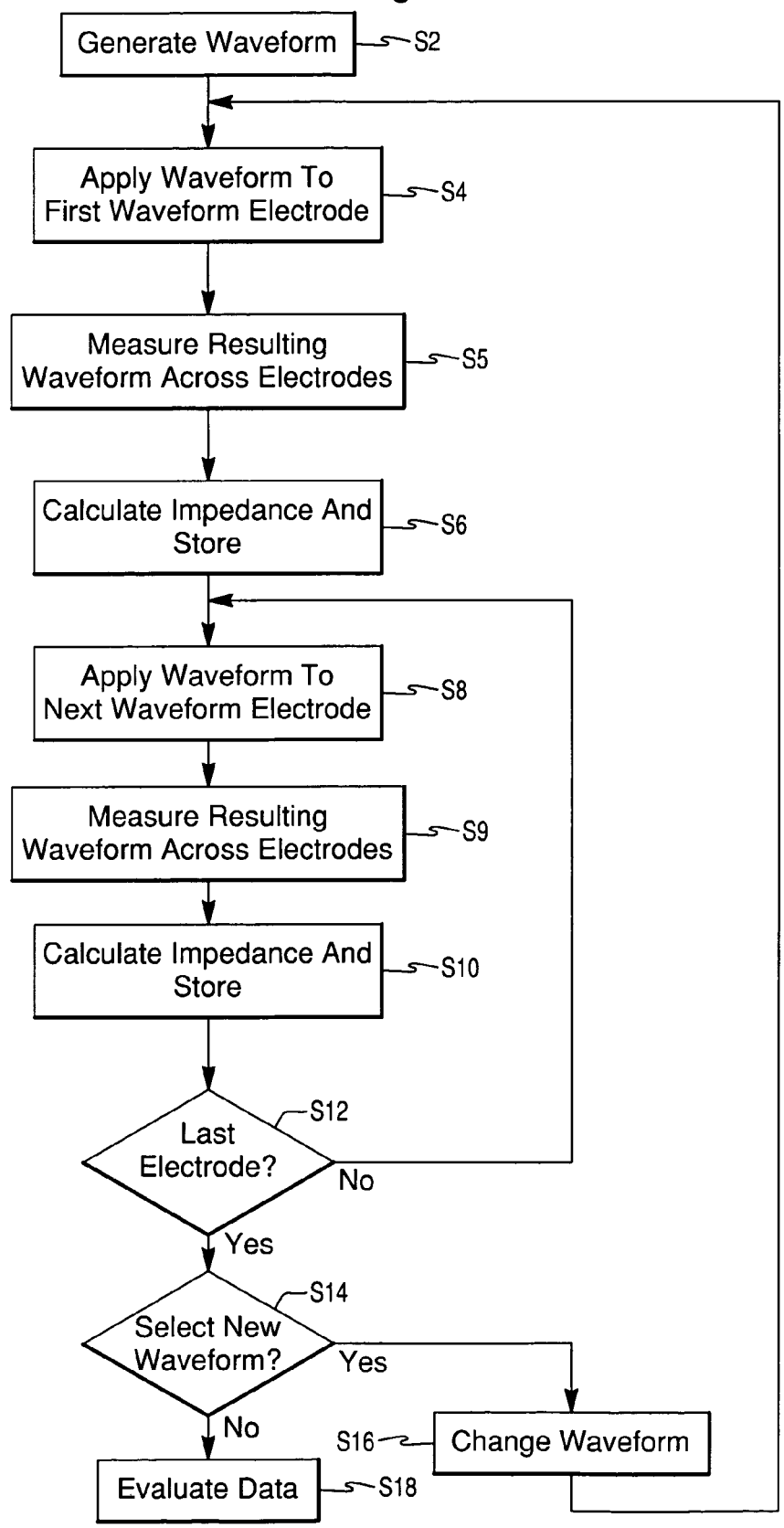
FIG. 10 illustrates a method of discriminating tissues which may be used with various embodiments of the present invention.

A method for discriminating tissue according to an embodiment of the present invention is illustrated in FIG. 10. In one method of the invention, the controller 16 instructs the switching device 38 to provide the generated waveform to a waveform electrode, e.g., $e_2$ for the sampling time, step S4. The generated waveform may be provided to each waveform electrode in a sampling cycle in either a predefined or a random order, Steps S8-S12. At the end of the sampling period, the controller 16 may instruct the waveform generator 21 to generate a different waveform to be applied to the sampling sensor system 12, Step S14, S16. Alternatively, the controller 16 may direct follow up sampling across specific electrodes based upon initial measurements, e.g., to confirm results, gather a statistically significant number of data points, or sample across particular electrodes over an extended period of time.

The impedances corresponding to each electrode in the array, which will correspond with underlying tissue structures, may be selectively determined for each generated waveform, S4. The operator may provide instructions to avoid determining the impedance for some of the waveforms. After determining impedance, various mathematical analyses may be performed using the plurality of impedance determinations, including calculating a ratio of impedance change to the applied current change. The mathematical analyses may also consist of calculations to support any effective data presentation technique, including but not limited to presentation of: raw data, normalization of raw data, rates of change between neighboring electrodes, rolling averages, percentage difference, derivative functions, or more complex analyses, e.g., Fourier analysis of frequency components, all of which may be presented graphically and/or numerically such as in a table of values.

The controller 16 may also determine from measured data the individual components of the impedance, namely the resistance and reactance. These may be calculated using known means, e.g., using a Fourier analysis technique to obtain amplitude and phase information of voltage and current waveforms and dividing voltage V by current I to determine the real (resistive) and imaginary (reactive) components of the impedance. Similarly, the controller 16 may calculate other electrical characteristics, such as permittivity, inductance, capacitance, etc.

In various embodiments, the controller 16 may provide a display signal to display 19. For example, the controller 16 may generate nerve tissue density distribution depicting x and y locators and a height related to the probability of nerve tissue under specific x, y coordinates to be displayed on the display 19. The generation of the images may be performed by using the impedance determinations with different waveforms. For example, directly measured values, or calculated results based on measured values, may be assembled into an image consisting of a single line, a 2-D density distribution, a display of tissue and nerve contents including nerve depth, or a 4-D display of the display over time, as more fully described herein. Among the values that may be displayed in a 2-D presentation are voltage, current, impedance, reactance, admittance, and phase shift, each of which are believed to disclose different information about the underlying tissues and structures, particularly nerves. Examples of various displays are provided in FIGS. 41-45. Alternatively, directly measured values, or calculated results may be displayed as a table of values, or numerical listings may be combined with graphical presentations.

Returning to FIG. 10, in a method according to an embodiment of the present invention, a waveform is generated (step S2) and applied to the first waveform electrode (step S4) during a sampling period. The waveform is sensed across the waveform and return electrodes and measured by the equipment (S5). At least one other characteristic is calculated based on the characteristics of the waveform measured across the selected waveform electrode and return electrode, e.g., voltage, current, frequency, duty cycle, etc., and the measured value and the at least one other calculated characteristic are stored by the controller (step S6). The waveform may then be applied to another waveform electrode (step S8), which may be selected by a switching device 38. The at least one other characteristic is calculated again based on the characteristics of the waveform measured across the newly selected waveform electrode and the return electrode. The measured value (step S9) and the at least one other calculated characteristic are stored by the controller (step S10). The apparatus applies the waveform to each of the waveform electrodes in turn by repeating steps S8 and S10 until the waveform has been applied to the last waveform electrode (step S12, NO). Once the waveform has been applied to all of the waveform electrodes (step S12, YES), the apparatus determines if there is another waveform to select (step S14) by determining if there are any waveforms in a predefined set of waveforms which have not been applied to the waveform electrodes or by prompting the operator to select another waveform. The new waveform may be changed from the previous waveform in any of the various parameters specifying a waveform, including maximum or minimum amplitude, shape of the waveform, frequency, duty cycle, etc. If another waveform is selected (step S14, YES), the waveform generator 21 generates a new waveform and the controller applies it to the first waveform electrode S4. Steps S4-S12 are then repeated with the new waveform. Once all of the waveforms have been applied to the waveform electrodes (step S14, NO), the controller evaluates the data by various calculations. For example, the controller may determine the $\Delta Z/\Delta I$ from the stored impedance, and the voltage and current data for each waveform electrode when applied with each waveform (step S18). The controller may also determine the reactance of the tissue. In an embodiment the operator may be able to instruct the controller to perform any type of calculation.

Figure 11:
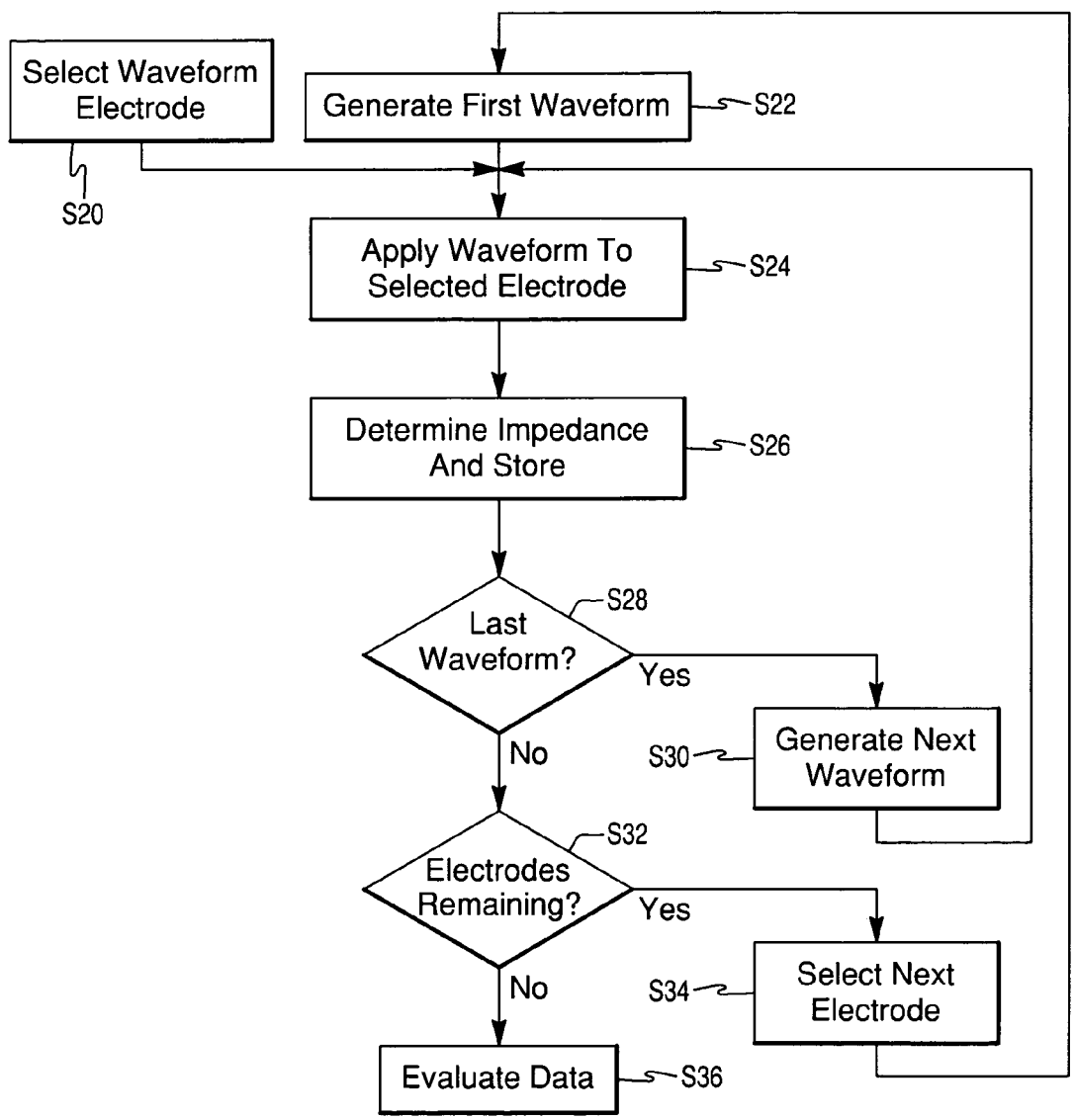
FIG. 11 illustrates another method of discriminating tissues which may be used with various embodiments of the present invention.

An alternative method is illustrated in FIG. 11. As illustrated in FIG. 11, a waveform electrode is selected (step S20) and a waveform is generated (step S22) and applied to the selected waveform electrode (step S24). The impedance or other electrical characteristic may be calculated based on the sensed signal and the characteristics of the waveform applied at the selected waveform electrode, e.g., voltage, current, frequency, and duty cycle, etc., and the characteristics and the calculated impedance may be stored by the controller (step S26). In step S28, the apparatus may determine if there is another waveform to select (step S28) by determining if there are any waveforms in a predefined set of waveforms which have not been applied to the waveform electrodes or by prompting the operator to select another waveform. The new waveform may be changed from the previous waveform in maximum or minimum amplitude, shape of the waveform, duty cycle, frequency and/or other parameter. If another waveform is selected (step S28, YES), the waveform generator 21 generates a new waveform (step S30) that may be applied to the selected waveform electrode (steps S24 and S26). If no more waveforms are selected (step S28, NO), the apparatus may determine if there are any waveform electrodes remaining which have not had a plurality of waveforms applied (step S32). If there are waveform electrodes remaining to be selected (step S32, YES), then one may be selected and another waveform applied to the newly selected electrode repeating steps S22-S30. If there are no waveform electrodes remaining (step S32, NO), the controller may evaluate the data by various calculations. For example, the controller may determine the $\Delta Z/\Delta I$ from the stored impedance, voltage and current data for each waveform electrode when applied with each waveform (step S18). The controller may also determine the reactance or other electrical characteristic of the tissue. In an embodiment the operator may be able to instruct the microprocessor to perform any type of calculation.

Figure 12:
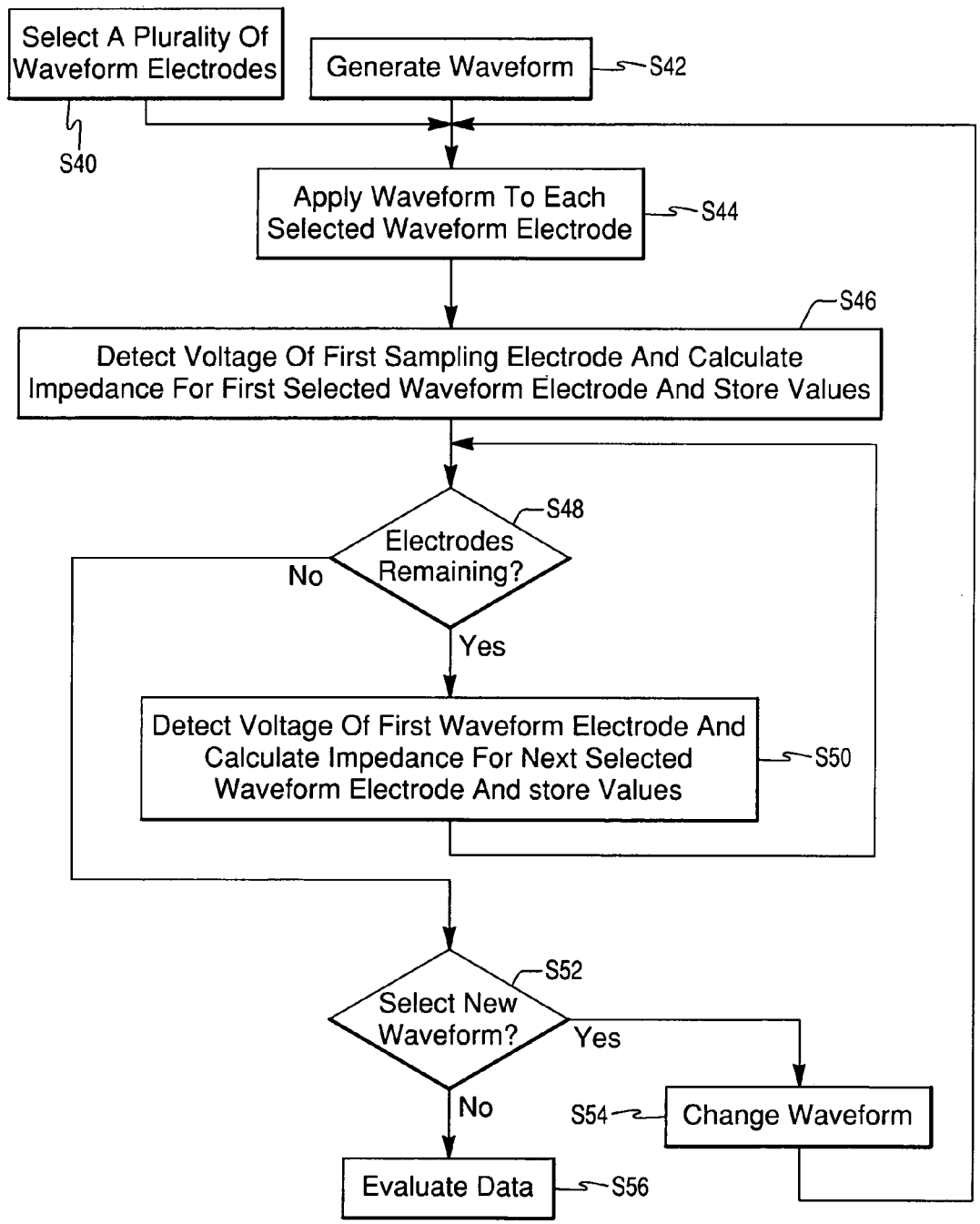
FIG. 12 illustrates another method of discriminating tissues which may be used with various embodiments of the present invention.

FIG. 12 illustrates another method embodiment according to the present invention. As illustrated in FIG. 12, a plurality of waveform electrodes may be selected (step S40) and a generated waveform (step S42) applied to each of the selected waveform electrodes in a manner so that each selected electrode receives the same current waveform (step S44). The voltage of each selected waveform electrode may be detected and the impedance or other electrical characteristic of each of the selected waveform electrodes may be determined (steps S46, S48 and S50). Since each of the selected waveform electrodes may be applied with the same current, the voltage may vary between each of the waveform electrodes, the voltage thus being the only unknown variable needed to determine the impedance. Once the impedance is determined for the selected waveform electrodes (step S48, NO), the controller 16 may determine if another waveform is to be selected (step S52). If a new waveform is to be selected, it may be generated (step S54), applied to the selected waveform electrodes, and steps S44-S52 repeated. If a new waveform is not selected, the controller may evaluate the data by means of various calculations. For example, the controller may determine the $\Delta Z/\Delta I$ from the stored impedance, voltage and current data for each waveform electrode when applied with each waveform (step S56). The controller may also determine the reactance or other electrical characteristic of the tissue. In an embodiment the operator may be able to instruct the microprocessor to perform any type of calculation.

Figure 13:
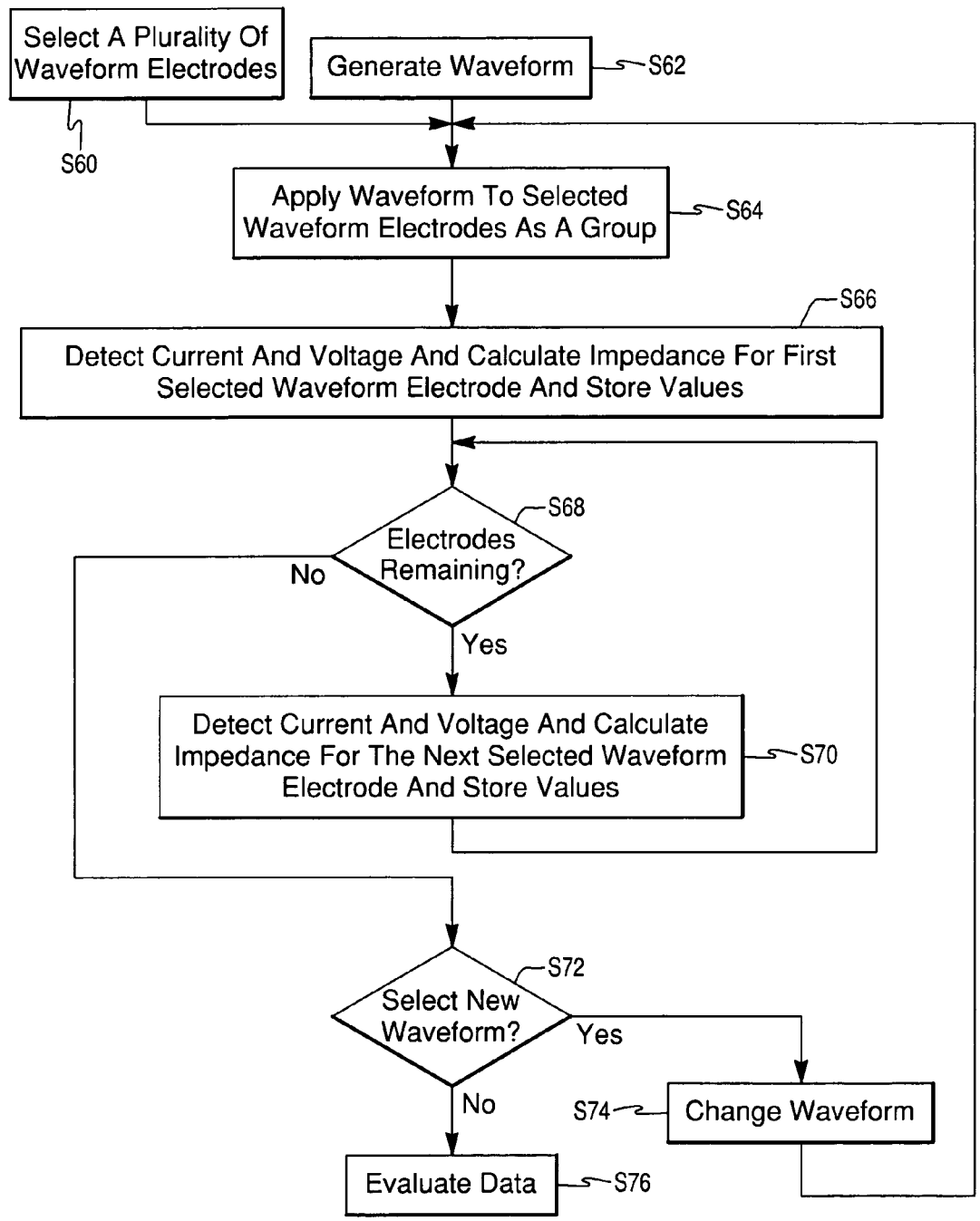
FIG. 13 illustrates another method of discriminating tissues which may be used with various embodiments of the present invention.

FIG. 13 illustrates yet another method embodiment of operating the present invention, in which a plurality of waveform electrodes may be selected (step S60) and a generated waveform (step S62) applied to the selected waveform electrodes as a group so that current of the generated waveform is distributed uniquely through each selected electrode (step S64). The current and voltage across each selected waveform and return electrode may be detected and the impedance determined (steps S66, S68 and S70). Since each of the selected waveform electrodes may receive a different current, and the voltage may vary between each of the waveform electrodes, both the current and voltage must be determined to calculate the impedance. Once the impedance (or other electrical characteristic) is calculated for the selected waveform electrodes (step S68, NO), the processor may determine whether or not another waveform is to be selected and applied to the selected waveform electrodes and the data are evaluated (S72, S74, S76) in the same manner as described for the preceding embodiments.

The apparatus of the embodiment illustrated in FIG. 8 may be operated in the same manner as other embodiments summarized in FIGS. 10-13 with the additional selection of the desired return electrode(s) in return electrode array assembly 51 which is/are used to complete the electrical circuit by switching device 52. The embodiment of FIG. 8 may also be operated in the same manner as described in connection with the embodiment of FIGS. 6 and 7, except that the waveform electrode in waveform electrode array assembly 18 to be used to complete the electrical circuit may be selected by switching device 38. In order to address the design consideration associated with the use of small area return electrodes, the electrodes in the waveform array and the return may be made sufficiently large (e.g., larger than approximately 10 mm$^2$) to integrate (i.e., average) underlying skin impedance characteristics. Alternatively, the waveforms across all electrodes in the return electrode array assembly 51 and the waveform electrode may be measured to determine the impedance integrating effect of a single large electrode followed by measuring the waveform across a single return electrode and the waveform electrode, with the controller 16 comparing measurements to determine the underlying impedance characteristics of tissue between the waveform and return electrodes. Alternatively, the waveform across all electrodes in the waveform electrode array assembly 18 and the return electrode may be measured to obtain the impedance integrating effectiveness of a single large electrode followed by application of the waveform across a single waveform electrode 1, with the controller 16 comparing measurements to determine the underlying impedance characteristics of skin beneath the waveform and return electrodes.

The embodiment illustrated in FIG. 8 also enables the system to select a particular return electrode from the return electrode array assembly 51 based upon the quality of the data measured across the waveform electrode array assembly 18 and the return electrode. As described above, nerves are associated with low impedance in narrow zones on the skin surface in the vicinity of a normal intersecting the plane of the skin surface and the underlying nerve. Consequently, the impedance between the waveform and return electrodes will depend upon the placement and contact area of the return electrode as well as the waveform electrode. Since nerves provide a preferential conductive path through tissue, it is expected that the quality of the measurement data, such as the degree of differentiation observed from waveform electrode to waveform electrode, will vary depending upon whether the return electrode is positioned above a nerve that is also beneath the waveform electrode array assembly 18. Accordingly, the embodiment illustrated in FIG. 8 may be operated in an iterative process to obtain data for the waveform electrode array assembly 18 according to any one of the methods illustrated in FIGS. 10-13 but further using, in turn, each return electrode within the return electrode array assembly 51 until a scan is obtained for each return electrode. This process essentially comprises repeating any one of the methods illustrated in FIGS. 10-13 as many times as there are electrodes in the return electrode array assembly 51. Having gathered these data, the controller 16 may then compare the results of the scans across the waveform electrode array obtained for each return electrode to identify the return electrode or electrodes providing the best resolution from the waveform electrode array assembly. Resolution may be measured in terms of the degree of discrimination observed from waveform electrode to waveform electrode (e.g., difference in measured or calculated values from one electrode to the next), from the peak waveform electrode to the average of all electrodes in the array, or a measure of statistical significance in the difference from one waveform electrode to another. Alternatively, resolution may be measured in terms of a rate of change in measured value from waveform electrode to waveform electrode. Once the controller identifies the return electrode that yields the best resolution in data obtained from the waveform electrode array assembly, further scans may be conducted using that return electrode according to any of the methods illustrated in FIGS. 10-13 in order to obtain more data for statistical analysis or to employ more waveforms, different frequencies or different testing modes (e.g., controlled voltage or controlled current modes). In this manner, the comparison of return electrodes and the selection of the return electrode yielding the best discrimination result are akin to focusing an optical instrument. Thus, the return electrode array assembly 51 may be a linear array that can be placed on the subject where the array should cross the nerve so the system can select the one electrode positioned above the nerve for conducting detailed scan operations.

An alternative embodiment is nearly identical to the above described structure and methods except that the frequency of the applied waveform is incremented or scanned across a range of frequencies, such as between approximately 500 Hz and approximately 2500 Hz, with data gathered for each frequency. As discussed above and illustrated in FIG. 19, it has been observed that different types of tissues exhibit different electrical responses to waveforms across this frequency range, so that contrasting the rate of change of the electrical characteristic (e.g., impedance, current or phase shift) as a function of frequency (i.e., determining $\Delta Z/\Delta F$, $\Delta I/\Delta F$ or $\Delta \Phi/\Delta F$) provides another basis for discriminating tissues. For example, it has been determined that nerve tissue, which has a high concentration of voltage-gated channels and a structure that exhibits greater capacitance than other tissues exhibits greater $\Delta Z/\Delta F$ than other tissues in the frequency range from about 500 Hz through approximately 2000 Hz (see FIG. 19). Thus, by conducting tissue discrimination scans according to the present invention at incremental frequencies ranging from approximately 500 Hz through approximately 2500 Hz, the different frequency responses of the calculated impedance can be used to recognize and discriminate different types of tissues. Further, this discrimination method can be used to contrast the waveform electrodes against each other to discriminate and localize the type of tissues underlying each electrode.

Figure 19:
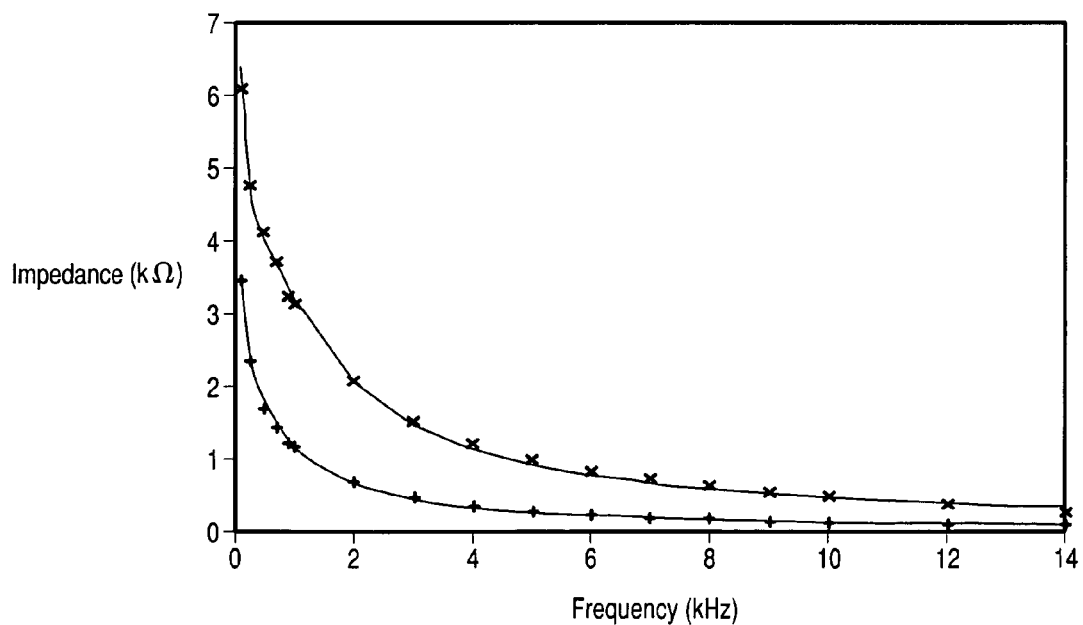
FIG. 19 presents impedance calculated from data measured across an acupuncture point and across a non-acupuncture point as a function of applied signal frequency.

FIG. 19 also illustrates a further refinement on this embodiment. By conducting tissue discrimination scans across a range of frequencies, such as from approximately 10 Hz through approximately 10 kHz, the data may be used to estimate resistance R and capacitance C of the RC equivalent circuit element representing tissue. Different tissue types are expected to exhibit different R and C values, and therefore the calculated values (e.g., R and C) may be used to identify the type of tissue underlying each electrode, such as in a table look up or filtering algorithm, i.e., neural network or fuzzy logic algorithm. By gathering measurement data for a range of tissue types from a range of subjects, characteristic R and C values can be determined, tabulated and stored in memory for use in an automated imaging, diagnostic and tissue discrimination system. Since the RC characteristics of tissues may vary from person to person and even from location to location on a given person, it is expected that the coefficient data may best be used in a filtering algorithm (such as are well known in the computer science art) which can accommodate such variability. Based on this, an embodiment of the present invention includes application of filtering algorithms to match measured RC electrical characteristics of tissues to standards, perhaps in combination with other information (e.g., operator entered information), to discriminate and identify underlying tissues. Such a filtering algorithm may also be able to recognize and discriminate mixed tissue types, such as nerves passing through muscle or tumors within muscle or viscera. This embodiment may further include the positional information provided by the waveform electrode array or the positionable electrode location systems described herein to map the locations of tissues within a subject. Such data may further be combined with standards or expected values for tissue distribution (e.g., typical positions and sizes of various organs or tissues) in a filtering algorithm to further refine the information obtained from a tissue discrimination scan according to the present invention.

Another alternative embodiment is nearly identical to the above described structure and methods except that the waveform is applied across the return electrode and all the waveform electrodes simultaneously.

An alternative embodiment is nearly identical to the above described structure and methods except that the return electrode is moved over the body while measuring across the return electrode and waveform electrode array assembly. This embodiment permits measuring changes in the electrical characteristics of tissue as the distance between the waveform electrode and return electrode 7 changes.

An alternative embodiment is nearly identical to the above described structure and methods except that multiple waveform electrodes 1 are applied to the body, e.g., on either side of the return electrode array assembly 51. This embodiment permits the waveform to be applied across various waveform electrodes and the return electrode, perhaps in alternating sequences between two waveform electrodes 1.

An alternative embodiment is nearly identical to the above described structure and methods except that there is no separate return electrode, rather the waveform is measured across one or more electrodes in the electrode array assembly 18 and one or more of the rest of the electrodes in the electrode array assembly 18. In this embodiment the waveform and return electrodes may be switched around the array 18 to determine if there is an effect on the measured data.

The example methods illustrated in FIGS. 10-13 may be executed or caused to be executed by the controller 16. Instructions for performing the steps of the methods may be stored in volatile or nonvolatile memory (e.g., PROM or EPROM memory) or on a computer readable medium connected to the controller. A computer readable medium is any tangible structure, e.g., a magnetic disk, an optical disk, or a magnetic tape; or intangible structure, e.g., a modulated carrier wave containing packetized data, which is a wireline, optical cable, or a wireless transmission; which is capable of being accessed by a microprocessor or computer. Thus, as used herein, the term "configured to" includes programmed to accomplish or function in the recited manner, as well as physically connected, assembled, wired or otherwise made to accomplish the function.

Figure 29:
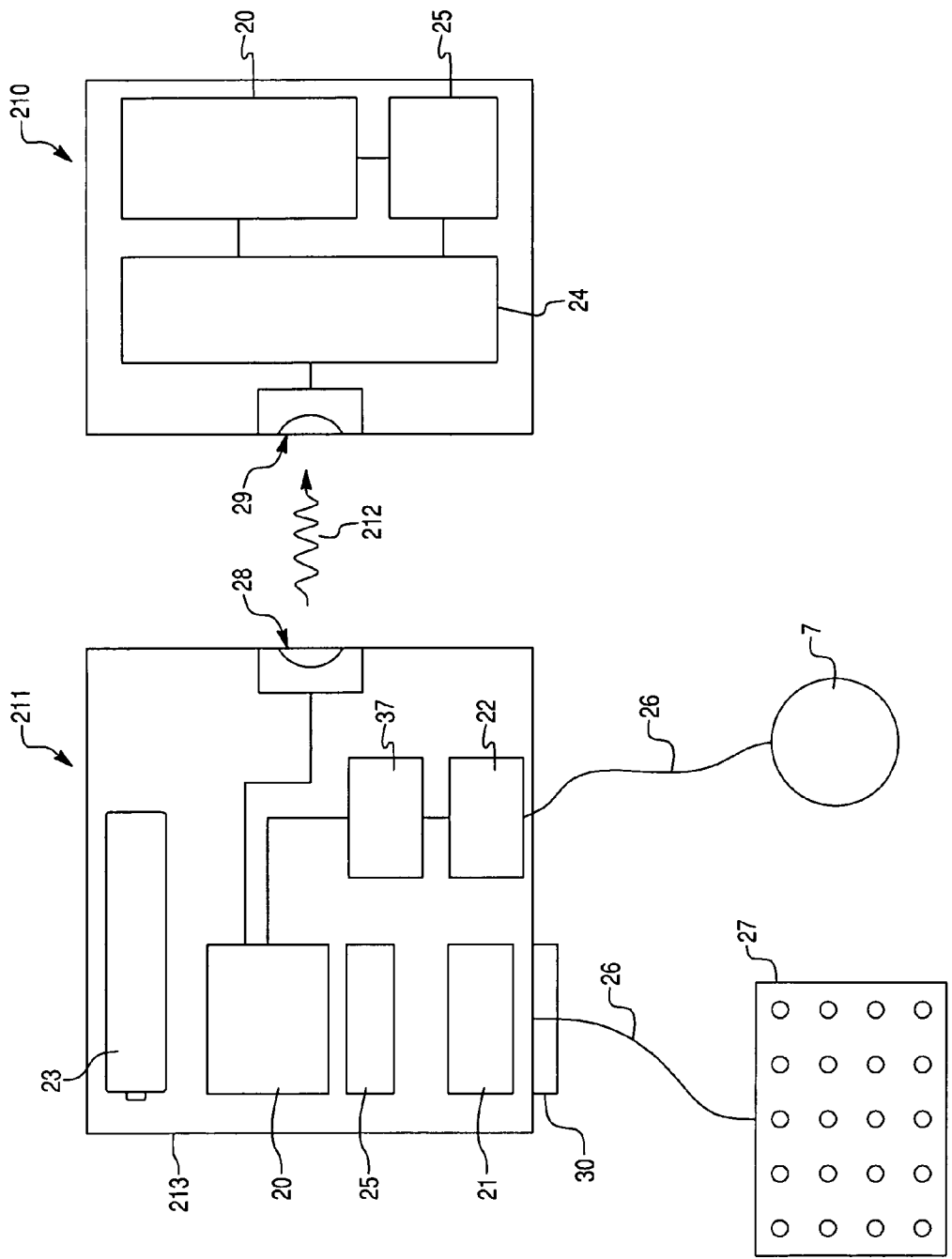
FIG. 29 illustrates a wireless embodiment of the present invention.

In an embodiment of the present invention, the waveform electrode array assembly may be configured as a system, such as illustrated in FIG. 39. In such a system, a conductor 26, e.g., a ribbon cable 391 or flex connector electrically connects each electrode in the electrode array assembly 392 to controller circuitry which may be contained in a housing 393. An example of such a ribbon cable conductor 391 is illustrated in FIGS. 39 and 40. The controller may be a computer, which includes a processor to operate control and processing software that is configured to generate specified commands to the circuitry, receive the measurement data from the array electrodes, and process the measurement and other data to determine useful scan information. Such information may include the location of discriminated tissue determined by computing the relative electrical characteristics of each electrode in the electrode array assembly. The system may also include a two-way communications link between the circuitry and a host computer to communicate the commands from the host computer to the circuitry and communicate the measured data from the circuitry to the computer. Such a datalink may be an electrical cable, e.g., a parallel cable or serial (e.g., RS-232) cable link. Alternatively, the datalink may be a means of wireless datalink transceiver providing a wireless datalink, e.g., infrared (IrDA), IEEE 802.11 g WiFi, Bluetooth or similar technology that exists or will be developed in the future. An example diagram of a system employing a wireless datalink is illustrated in FIG. 29, and a prototype embodiment is shown in FIG. 39. In the prototype embodiment illustrated in FIG. 39, a first wireless datalink transceiver is contained in the housing 393 connected to the electrode array assembly 392, while a second, compatible wireless datalink transceiver is contained in a second housing 394 which is connected to a USB cable 395 for connection to a personal computer (not shown). In the prototype embodiment illustrated in FIG. 39, the return electrode is built into the housing 393 (on side not shown) so that connection of the return electrode with skin can be achieved by laying the housing 393 on the skin of a subject, preferably with a layer of coupling interface material applied to the electrode and/or the skin. The wireless configuration illustrated in FIGS. 29 and 39 permits the electrodes and attached circuitry to be positioned on a subject when the host computer is separate and, perhaps, located a distance from the subject.

An alternative embodiment of the present invention includes an electrode array assembly configured to permit extended use on the skin of a subject. By extending the time that the electrode array assembly can remain on the skin, and thus the duration of monitoring nerve function, a number of diagnostic, clinical and surgical applications are possible. To increase skin contact time, modifications to the electrode array assembly patch may be required. These may include the use of materials with hypoallergenic properties, using sponge material with sufficient porosity to permit air to reach the skin between electrodes, and attachment methods (e.g., tape or straps) that do not cause skin irritation. Modifications to the electrode wells may also be used to increase useable time, e.g., increasing the volume of the electrode well, providing a reservoir for coupling interface material or providing a channel or access to permit periodic replenishing of the coupling interface material. The use of such long duration electrode array assemblies would permit clinicians to monitor nerve recovery, re-growth, or return of function after injury or in response to treatments, for example. Further, long duration electrodes would be useful in extended surgical operations to monitor the effectiveness of local anesthetic, permitting reapplication before nerve function returns.

In a further embodiment, the electrode array assembly and controller/signal generator may be configured as a wireless component or module configured so that it can be worn by a patient or placed on a patient at a distance from the host computer. As used herein, the terms "wireless," "wireless link," "wireless datalink," and "wireless connection" refer to any data communication system, technology or method capable of reliably transmitting and receiving data between two devices by means of transceivers which may be separated by a short (matter of inches) or long (matter of feet to miles) distance, including, by way of example but not by way of limitation, infrared datalinks (IrDA), IEEE 802.11 g, wireless fidelity (WiFi), and Bluetooth, and similar datalink technologies and/or standards that are well known in the art and/or will be developed in the future, wireless telephony e.g., FM radio (e.g., used in cordless telephones), cellular telephone, satellite telephones, and/or civil or military data transceivers. In certain hospital environments where electromagnetic radiation may need to be minimized, a standard infrared datalink (IrDA) may be preferred. Using a wireless datalink between the electrode array assembly and the controller minimizes the impact on other equipment and attending clinicians. This may permit the monitoring of large nerves on limbs or along the spine during surgery without the risk of connecting wires contaminating the sterile zone, tripping or interfering with the motions of clinicians, or becoming entangled with the patient or other equipment. The wireless configuration may also permit the monitoring of nerve function while the patient moves about or performs exercises. This would permit monitoring nerve function during physical movements that stimulate the nerve; i.e., to determine sources of pain, assess nerve function during movement or exercise, or assess nerve fatigue during exercise.

The elements of a wireless embodiment are illustrated in FIG. 29. These elements include an electrode array assembly 27, the electrical interface 30 for connecting the electrode array assembly to the transceiver module, a transceiver module 211, and a system transceiver 29. A photograph of a prototypical wireless electrode system is shown in FIG. 39. While the electrode array assembly 27 and the electrical interface 30 may be as described for the conventional system, the transceiver module 211 and system transceiver 210 may include additional elements as illustrated in FIG. 29.

Referring to FIG. 29, the transceiver module 211 may include a housing 213 within which are positioned a power supply 23, controller circuitry 20, memory 25 (e.g., flash memory, EPROM or volatile memory), and a transceiver 28. The transceiver module 211 may also include amplifier 22 and signal processing circuitry 37 capable of amplifying the signals received from the electrodes and performing preliminary signal processing.

The transceiver housing 213 may be made of a material that is compatible with sterilizing solutions or methods, and sealed such that it can be submerged during sterilization, so that the module can be sterilized sufficiently to permit its use in an operating room environment. Alternatively, the housing 213 may be disposable, e.g., a two- (or more) piece enclosing shell that can be clasped around the electronics in order to provide a sterile boundary around the electronics. Such a disposable shell or housing may be made of any sterilizable material, e.g., plastic, and in the form of two or more shells or pieces that snap, screw or otherwise couple together. A gasket or similar seal may be used to form a suitable seal between the shells or pieces. Nonlimiting examples of such housings include a container with a screw on cap or lid, a clam-shell configuration with a hinge on one side and a snap or latch on the other side, and two halves joined with a sealing configuration, e.g., tongue-in-groove or bayonet fit, to form a sterile boundary.

The power supply 23 can be any suitable store or portable source for electrical power, including, e.g., disposable (i.e., replaceable) batteries, rechargeable batteries, photocells, fuel cells, or other power supplies with sufficient stored energy and power capability to drive the controller 20 and amplifying circuitry 22, 37, and the transceiver 28.

The transceiver module 211 includes a transmitter and receiver, or transceiver 28, as are well known in the art, which is configured to transmit data received from the electrodes and receive control commands from the controller or host computer 210. In an embodiment, the transceiver module 211 may include only a transmitter, an embodiment that may be suitable for applications where control functions (e.g., on/off) can be accomplished via buttons or switches on the module itself. In various embodiments, the transceiver 28 may transmit and receive information via radio frequency according to any suitable wireless datalink as discussed above.

Referring to FIG. 29, the system controller 210 includes a transceiver 29 that is compatible with (i.e., capable of sending control signals to and receiving data and configuration signals from) the transceiver 28 in the transceiver module 211. The system controller 210 also includes circuitry sufficient to communicate the data received from the transceiver module 211 to the controller 210 or host computer and data processor. This circuitry may include signal conditioning electronics (e.g., gain amplifiers or filters) and cables for connecting to the controller/data processor. The circuitry may also include a microprocessor 20 operating software to provide control and signal processing in addition to or as an alternative to processing in the controller/data processor equipment. In an alternative embodiment, multiple wireless datalinks may be utilized to communicate data and commands between a host computer/data processor and the electrode array assemblies. For example, a first datalink may be an IrDA link within an operating room that is connected via an 802.11 g wireless local area network to a computer that further transmits data and commands via a satellite datalink to a processor at a distant location. Such configurations may be used in telemedicine and paramedic applications.

In the various embodiments, electrodes make electrical connection with the skin by means of a coupling interface material, which may be an electrolyte or electrolyte gel, e.g., a hydrophilic, silver-silver chloride gel. In any system where metallic conduction (i.e., wires, flat plates) transitions to ionic conduction in an electrolyte medium (e.g., within tissues), one must consider differences in the entities carrying charge for the two media. In metallic conduction, charge is carried by electrons moving between adjacent electron clouds surrounding the atomic nuclei. In ionic conduction, charge is carried in solution on ions which move toward oppositely charged electrodes. Contact adequacy at the boundary between the metallic phase and the electrolyte phase (e.g., at the skin) determines the efficiency of the transition. This contact ensures the effective exchange of the charge carried by ionic moieties with the metallic surface. In a medical electrode system, the interface medium between the metal (or metal: metal salt) electrode and the skin provides this contact. To maximize the contact efficiency, the coupling interface material should physicochemically wet the surfaces of both the electrode and the skin. Further, an aqueous coupling interface medium facilitates hydration of the skin and helps reduce the normally high impedance presented by the stratum corneum, thereby improving electrical conduction through the skin. The coupling interface material should also display a low energy contact that allows the material to spread effectively over the surface, filling any interstices that are present. Thus, the coupling interface material performs the function of facilitating the conversion of electrical signals from conduction via electrons in the electrode to conduction via ions within tissues. If there is an aqueous medium between the electrode and the skin surface, the conversion occurs in this medium. If dry metal electrodes are applied to the skin surface, the transition occurs in the stratum corneum layer of the skin.

Preferably, the coupling interface material exhibits low impedance itself. An example of a suitable coupling interface material is a Redux paste distributed by Parker. However, other commercially available and proprietary gels have been shown to work as well. In addition to exhibiting low impedance, the coupling interface material also should exhibit suitable viscosity/tackiness, safety on the skin, aqueous, (physicochemical) skin wetting, etc. Further characteristics of suitable coupling interface materials are disclosed in U.S. Pat. Nos. 6,564,079 and 6,609,018, which have been incorporated by reference. At least with certain coupling interface materials, good results are obtained on non-hydrated skin (readings within 5 minutes of array application to intact skin). In addition, it will be appreciated that materials other than gels that provide the necessary conductive skin interface may be used.

In an embodiment, electrodes may be applied on a mucous membrane, subcutaneously, or intraoperatively. Placement of electrodes on a mucous membrane or below the skin may obviate the need for a coupling interface material, and would permit placement of electrodes closer to some nerves of interest. For example, during surgery of the abdomen or large muscles, an electrode array assembly, which may be in the form of an array of pin or needle electrodes, may be placed on exposed tissue in order to locate and image underlying nerves, e.g., to ensure nerves are not cut in subsequent incisions. This may have utility for imaging nerves that lie far below the skin surface and thus may only be revealed during surgery.

In another embodiment of the present invention, electrically activated dyes are included in the coupling interface material. Such electrically activated dyes are activated when exposed to a voltage or current above a threshold, causing the dye to be released, formed or activated so as to mark the skin. An example of such a dye is one in which the dye is encapsulated in microspheres having membranes that will open or burst when exposed to a voltage above a particular threshold, e.g., a high enough voltage to change the polarity across the microsphere membrane. Another example of electrically activated dyes are a mixture of a catalyst and dye-constituent elements where applying a voltage or current above a threshold provides sufficient energy for the catalyst to assemble the dye molecules. Another example of electrically activated dyes are amine-activated dyes in which an ammonium ($NH_4^+$) group, which is typically colorless, is converted to the amino form ($NH_3$), which is typically colored, by the uptake of an electron as may occur when a voltage is applied to, or a current is passed through the medium containing the dye material. Including electrically activated dyes in the coupling interface material permits the operator of the nerve imaging system to mark a particular skin site corresponding to a specific electrode or electrodes, e.g., to indicate the presence of a nerve below it, by applying a bias voltage to activate the dye and leave a mark that will remain when the electrode array assembly is removed. This embodiment thus permits the nerve imaging system to mark the skin at the location of electrodes nearest to a nerve, thereby providing a rough trace of the nerve on the skin or marking a single electrode location as a preferred site for an injection or a location to avoid when making a surgical incision. Marking the nerve on the skin with a dye that will remain, e.g., after sterilizing of the area, would help an anesthesiologist or surgeon locate or avoid the nerve in subsequent procedures. In a further embodiment, multiple electrically activated dyes of different colors that may be selectively activated by different voltage/current thresholds may be used to permit the nerve imaging system to mark the skin with different colors. The use of multiple color electrically activated dyes may permit indicating a gradient in nerve function, shallow nerves (which may be traced in one color) versus deep nerves (which may be traced in a second color) or providing other information on the skin to aid clinicians in subsequent procedures.

Skin marking would allow the anesthesiologist to determine preferred sites for local anesthetic injection, while not piercing the nerve in the process. The surgeon's major use of nerve identification, at least initially, may be to avoid transecting a nerve in preparation for or during surgery. A significant application of nerve identification, particularly when combined with skin marking, may be to target anesthesia or other treatments to nerve specific tissues.

In another embodiment, the coupling interface material used in each electrode well may include a dye so that when the electrode array assembly is removed, a positive image of every electrode is left on the skin. Thus, the well itself provides a reservoir for the dye. As an alternative, the dye may be stored in a reservoir near one or more of the wells to leave a mark on the subject corresponding to the positions of the electrodes. An image of the electrode array would help an anesthesiologist or surgeon interpret results of the nerve imaging system and thereby avoid damaging nerves in subsequent procedures, for example. In a variation of this embodiment, the electrodes within an array may have different color dyes in the gel so that the location of each electrode can be recognized based on its color.

In another embodiment, the adhesive layer on the electrode array assembly or pad of the electrode array assembly may contain a dye (or a dye layer) that marks the skin wherever it makes contact. This embodiment will leave a "negative" pattern of the electrodes on the skin, i.e., electrode locations will not be dyed. The advantages of this embodiment are similar to those of the embodiment employing dye in the coupling interface material, with the added advantage that there would be no interaction of the dye with the coupling interface material.

Figure 30:
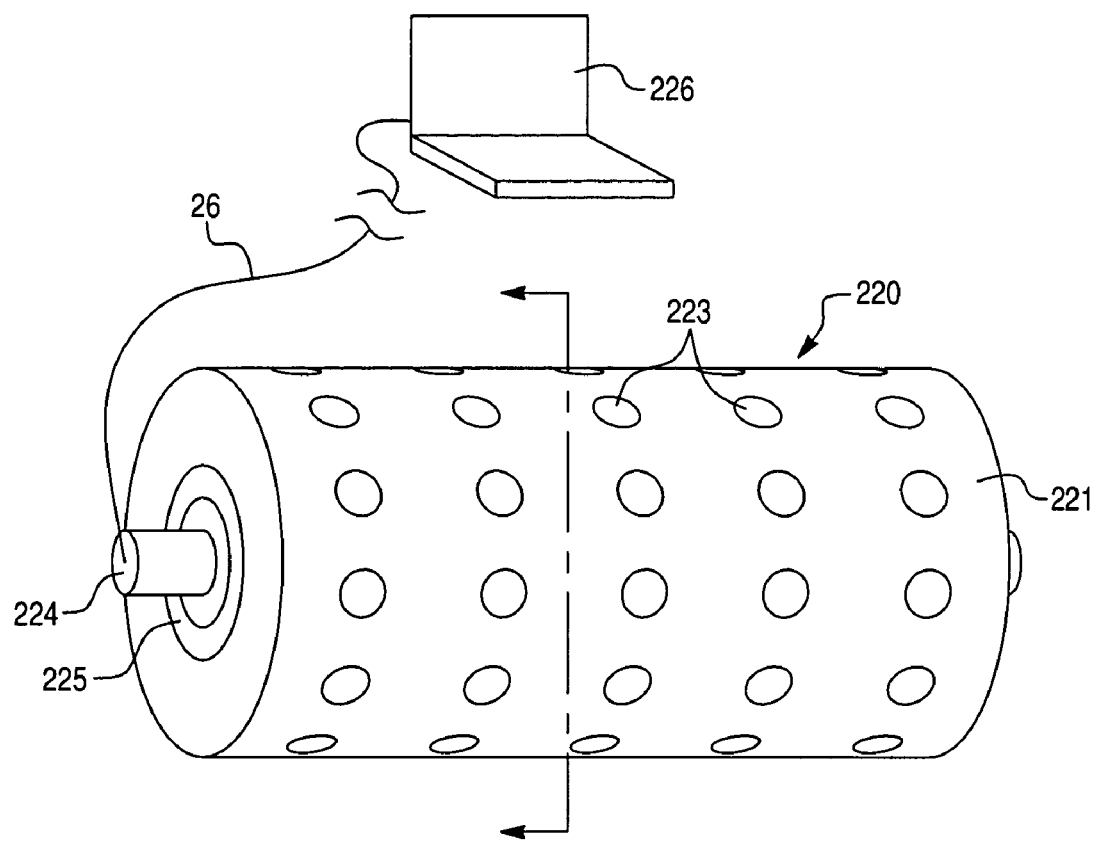
FIGS. 30, 31, 32, and 33 illustrate a rolling electrode array assembly sensor system according to various embodiments of the present invention.
Figure 31:
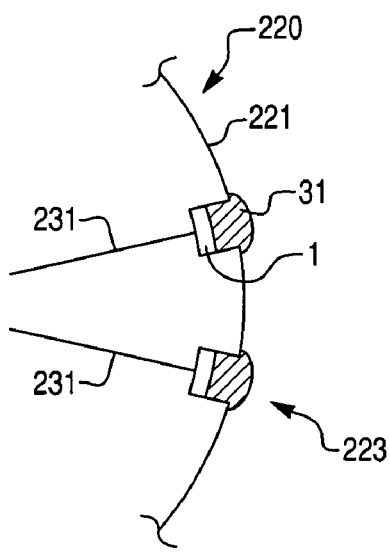

Another embodiment of the electrode array assembly is shown in FIGS. 30, 31. This electrode array assembly is in the form of a roller 220 configured to rotate about an axle 224 to permit scanning large areas of a body of the subject. In operation, the roller may be slowly advanced as sufficient data is gathered on each electrode. Electrode wells 223 are positioned on the cylindrical (or approximately cylindrical) surface 221 of the roller 220. Each electrode well 223 may contain an amount of coupling interface material, e.g., electrolyte gel 31 to provide suitable electrical contact with skin. An electrode 1, which may be simply a conductive disk or square within the volume of the well 223, makes electrical contact with the coupling interface material 31. Each electrode well 223 is electrically connected by electrical leads 231, e.g., wires or conductors, leading from the electrode 1 to a roller connection circuitry 225 that connects to a cable 26 coupled to the controller 226. The roller connection circuitry 225 may be a rotatable electrical conductor assembly that provides a continuous electrical connection between the roller electrode conductors 231 and the cable 26 while the roller 220 rotates about the axle 224. This rotatable electrical conductor 225 assembly may be a slip-ring connector as is well known in the art. Alternatively, the rotatable electrical conductor assembly 225 may be flexible cable or cables (not shown) sufficiently long and configured so that they may be rolled or twisted as the roller 220 advances without kinking or breaking contact. In a further alternative embodiment, a switching or multiplexing circuit, similar to that illustrated in FIGS. 6 and 8, may be positioned within the roller 220 so that the rotatable electrical conductor 225 only conducts a few electrical leads, such as one or more data leads and one, two or more data leads, such as one data lead and two address/switch circuit control signal leads. As in other embodiments, the controller may send signals to direct the switching or multiplexing circuit to electrically connect a selected electrode to the one or few data leads.

The roller design permits the electrode wells 223 to make individual contact with the skin while remaining electrically isolated from other electrodes. Wells 223 may be formed in the roller 220 by removing a volume of the roller (e.g., by drilling shallow holes in the roller) and placing the electrode 1 in the well, as illustrated in FIG. 31. Alternatively, wells may be made by positioning electrodes 1 on the cylindrical surface of the roller 220 and by wrapping the roller with an insulating pad (not shown) containing through holes similar to that disclosed in U.S. Pat. Nos. 6,564,079 and 6,609,018, with the electrodes 1 positioned on the roller to match the pattern of holes in the pad so that a single electrode 1 is positioned within each through hole (i.e., the positions of the contactors and through holes correspond one to another). In an embodiment, the roller assembly is configured as a replaceable part that slips onto an axle 224 on the handle 251 (illustrated in FIG. 33) and connects to conductors 26 on the handle 251 by means of an electrical connector (not shown). In this replaceable roller embodiment, the roller electrode assembly 220 may resemble a paint roller in the manner in which the roller electrode 220 is positioned on an axle 224 on the handle 251 with the electrical connector 225 being positioned at an end or as contactors on the inside of the roller 220 that match and make electrical connection with corresponding contactors on the axle 224 when the roller 220 is in position on the axle 224. In this embodiment, a peel-off sealing layer (not shown) may be used to seal the roller surface 221 to maintain the coupling interface material 31 within the electrode wells 231 until used.

Figure 33:
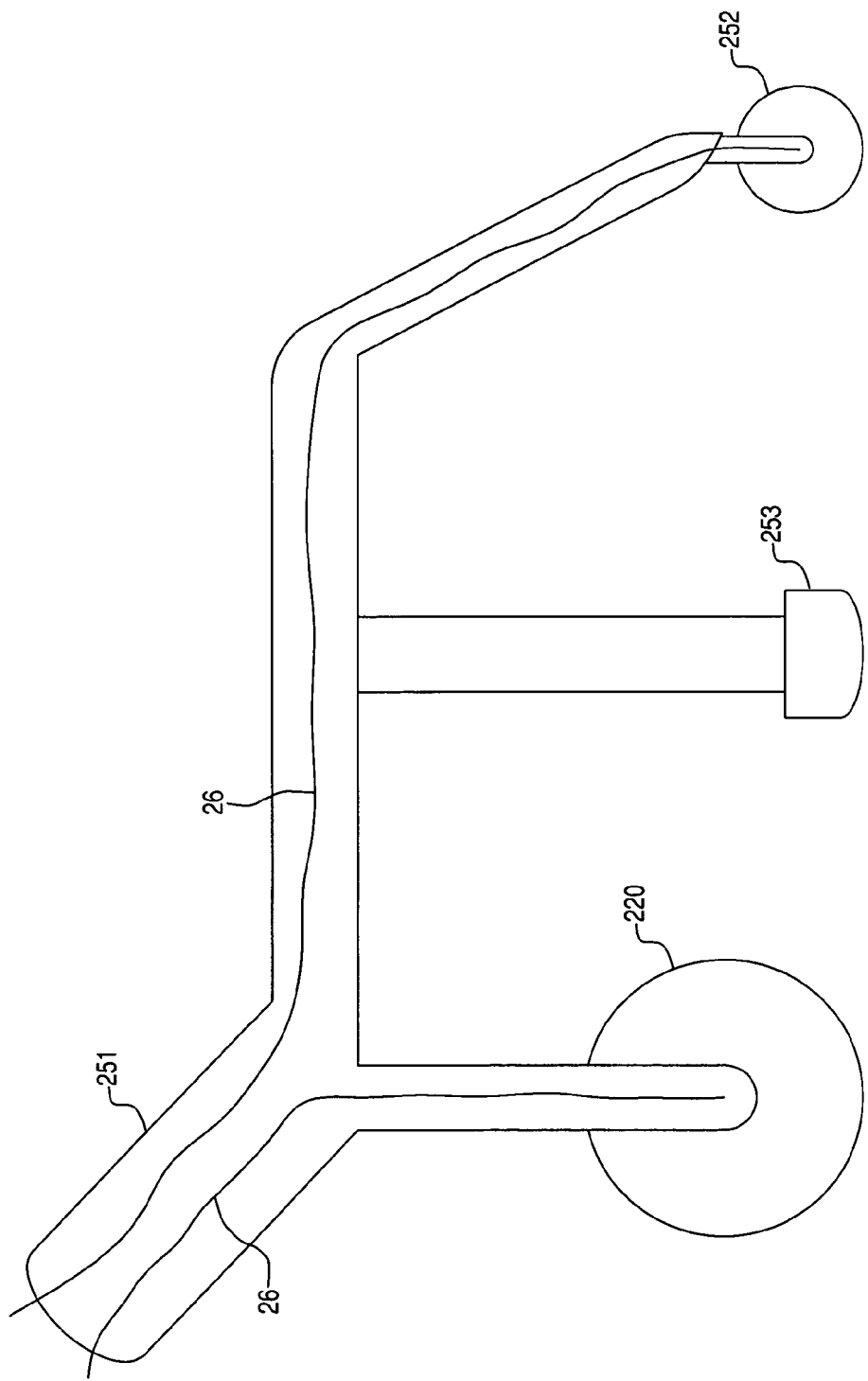

In another related embodiment illustrated in FIG. 33, the return electrode may also be in a form of a roller 252 with a rotatable electrical connector (not shown) that is rotatably coupled to the handle 251 so that the return electrode 252 to waveform electrode 1 distance remains constant as the assembly is rolled over the body of a subject. In yet another related embodiment, an ultrasound transducer 253 may also be mounted on the handle 251 to permit simultaneous ultrasound and tissue scans. As described more fully below, simultaneously scanning with the tissue discriminating system of the present invention and an ultrasound transducer may permit clinicians to correlate positions of discriminated tissues, e.g., nerves, with other tissue and bone structures imaged by ultrasound.

Figure 32:
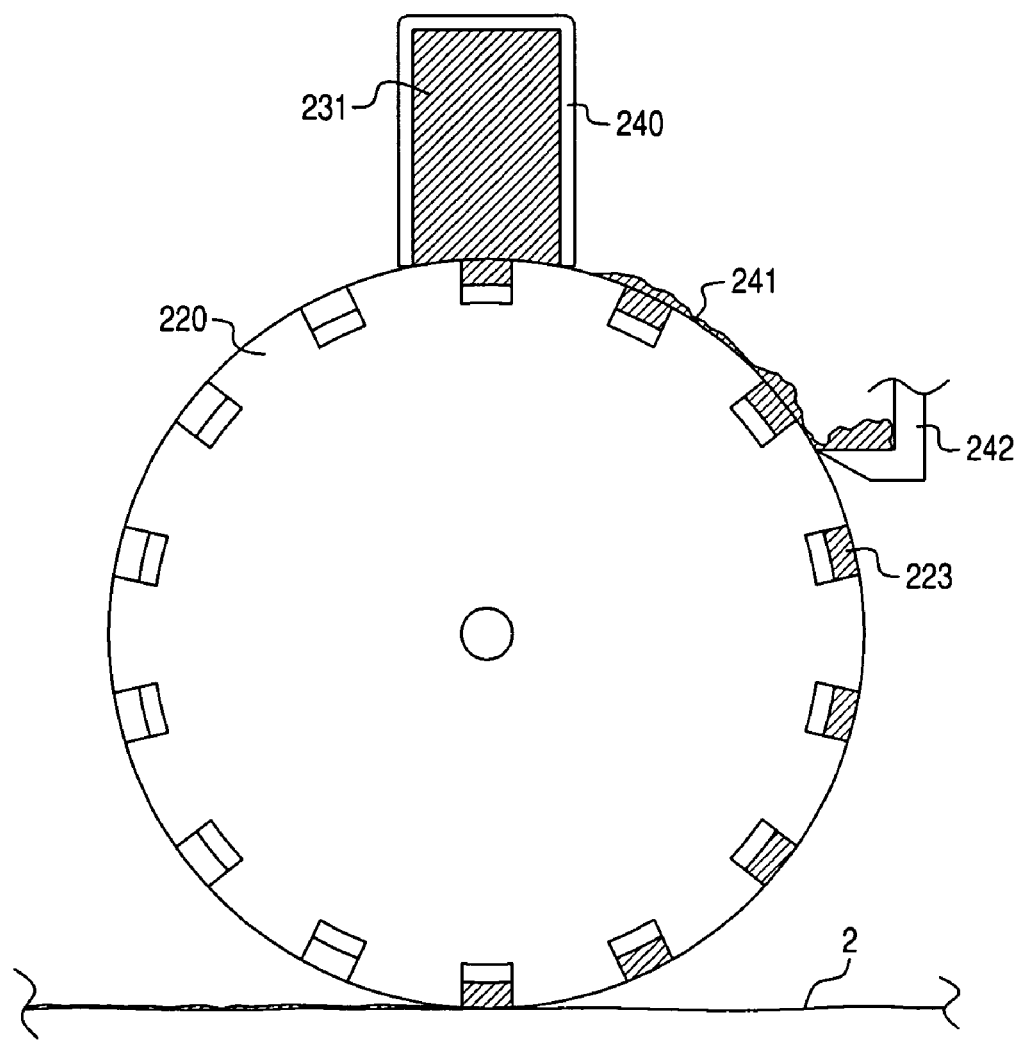

In another embodiment shown in FIG. 32, the electrode array roller 220 may be maintained in fluidic contact with an electrolyte gel reservoir 240 which fills electrode wells 223 with an electrolyte gel 231 as the roller 220 turns beneath it. A gel wiper blade 242 may be positioned behind (i.e., downstream) of the reservoir 240 to remove excess gel 241 from the surface of the roller in order to avoid short circuits from forming through excess gel 241 between adjacent electrode wells 223 when the wells are in contact with skin 2. Providing a continuous supply of electrolyte gel 231 ensures that an adequate and reproducible amount of coupling interface material is provided as the roller 220 is moved across the skin 2. This embodiment permits scanning an area of the body longer than the circumference of the roller. In an alternative embodiment, a film or pad is placed on the skin 2 which pre-conditions the skin for nerve imaging. The roller electrode assembly is then rolled over this film or pad in order to image a subject. Such a pre-conditioning pad or film would enable use of a non-gel coupling interface material since the pad or film would be the coupling interface, and thus serve the functions (e.g., skin hydration and electron-to-ion conduction coupling) of an electrolyte gel.

Figure 34A:
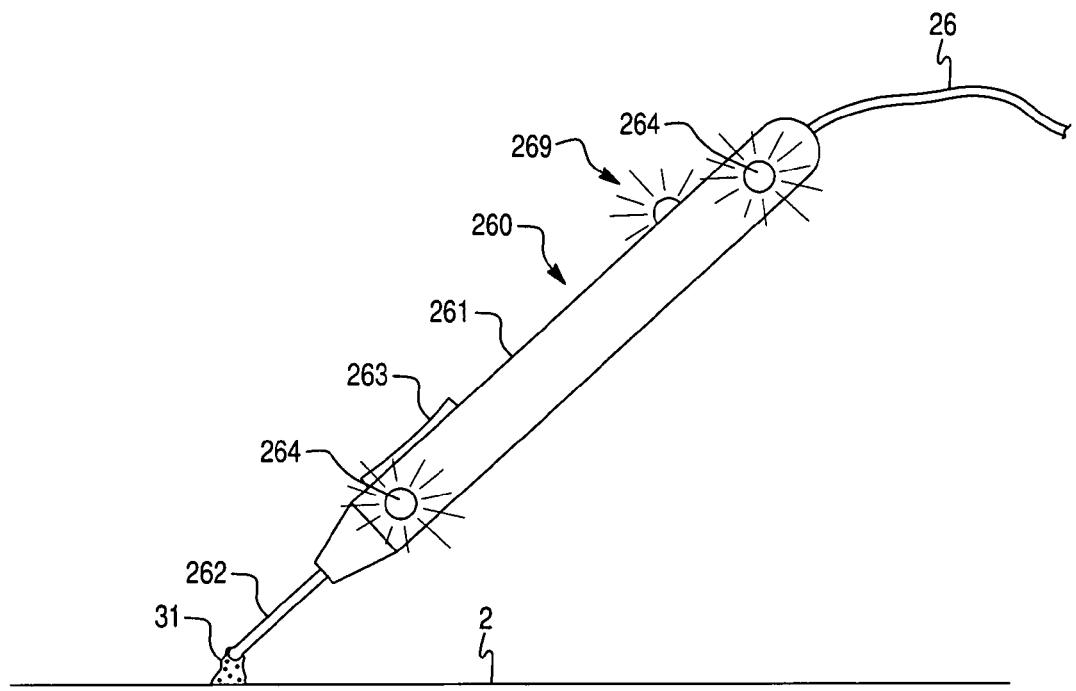
FIGS. 34 A-C illustrate a handheld electrode embodiment according to the present invention.

In an alternative embodiment, the waveform electrode 1 may be replaced or augmented by a handheld electrode, e.g., an electrode in a stylus or a pen system (referred to herein as a "pen electrode"). An example of a pen electrode is illustrated in FIGS. 34A. A pen electrode 260 may include a body 261 shaped suitably for being held by an operator, an electrode 262 extending from the body 261, and a cable 26 for connecting the electrode to a signal generator (not shown) or sensor circuit (not shown). In this embodiment, the pen electrode 260 may be used as a probe that can be freely placed on and moved about the skin of a subject until a signal peak is detected, at which point the pen may be used to make a dot on the skin where the signal peak was detected. This embodiment may include the use of a coupling interface material, e.g., an electrolyte gel 31, that is applied over an area of the body, not just on the electrode tip. Alternatively, coupling interface material 31 may be emitted from or about the tip of the electrode 262 from an internal or external reservoir (not shown), which may be dispensed by via dispenser (e.g., gravity feed, pump or air pressure in the reservoir) by the operator pressing an actuator such as a button 263. An actuator button 263 may also or alternatively be configured to allow the clinician to energize the electrode 262, such as by pressing the button 263 when a waveform signal is to be applied. In a further embodiment, the pen electrode 260 may include an status indicator light 269 that is coupled to circuitry and configured to indicate when an acceptable electric connection has been achieved with the skin of a subject, such as may be detected or indicated by impedance falling below a threshold or current rising above a threshold. The indicator light 269 may be configured so it shines red when the pen electrode 260 is energized but not in contact with a subject and green when the electrode 262 is in proper electrical connection with the skin of the subject. The circuitry required to drive the indicator light 269 is well known in the art and may be as simple as a circuit that compares current through the electrode 262 with a threshold standard.

Figure 34B:
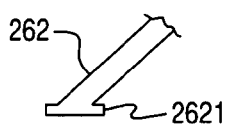
Figure 34C:
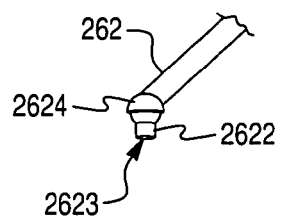

Embodiments of the pen electrode system 260 may include features on the electrode 262 to constrain the area of the electrode in contact with the skin. In an example embodiment illustrated in FIG. 34B, the electrode 262 may terminate in a flattened surface 2621, such as a disk or square, of constrained area, such as less than approximately 10 mm$^2$. Such a flattened surface may help reduce variation in skin contact resistance resulting from different amounts of applied pressure. In an alternative example embodiment illustrated in FIG. 34C, the electrode 262 terminates in a hollow cylinder 2622 containing a volume 2623 that can be filled with coupling interface material (e.g., electrolyte gel). As discussed herein, the use of a cylinder encompassing the coupling interface material reduces the effect of application pressure upon the skin contact resistance. Within the volume 2623 will be an electrode (not shown) that will make electrical contact with the coupling interface material in the volume. The cylinder 2622 may made of a conductive material or of an insulator material such as a polymer. Further, the cylinder 2622 may be physically coupled to the electrode 262 by means of a pivot 2624 so that the cylinder 2622 can be placed in right-angle contact with the skin regardless of the angle at which the pen body 261 is held by the clinician. The use of such a pivot 2624 may help to further reduce variations in resistance since the contact angle with the skin can be approximately the same from site-to-site and from operator-to-operator.

Figure 35A:
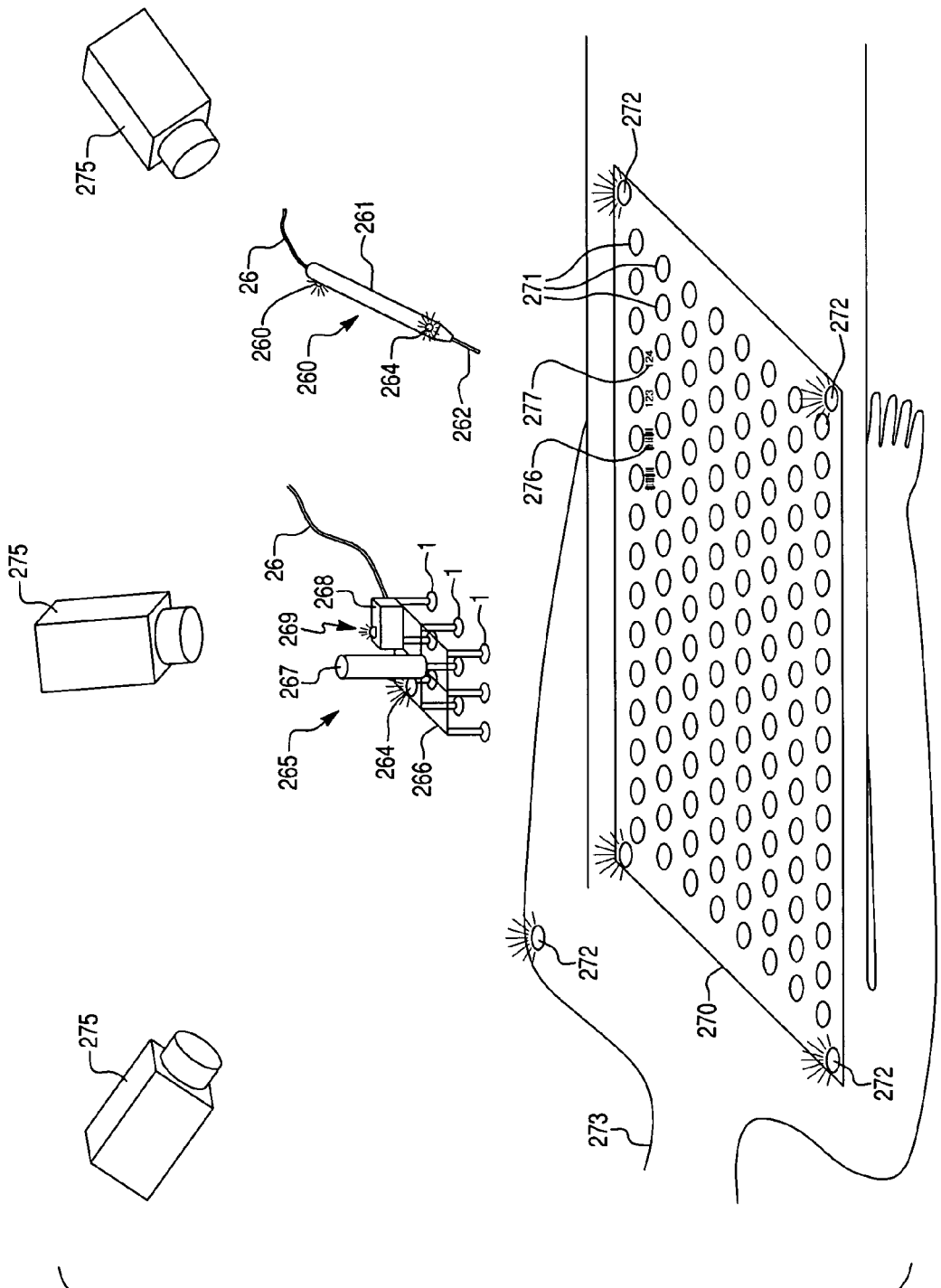
FIGS. 35A-C illustrate an image-guided system embodiment of the present invention.

In a related embodiment, a positionable electrode 265, illustrated in FIG. 35A, may include an array of electrodes 1 suspended from or otherwise supported by a frame 266 and connected by a cable 26 to a controller (not shown). A handle 267 may be attached to the frame 266 to allow a clinician to pick up and position the electrode array assembly by hand. A positionable electrode 265 may include attached electronics 268 for generating, amplifying or otherwise controlling the applied waveform. Also, a position-indicating fiducial marker 264 may be attached to the frame so the location of the electrode array assembly in space, e.g., with respect to the body of a subject 273, may be measured by a position measuring system 275 as discussed more fully below. In a further embodiment, the positionable electrode 265 may include a status indicator light 269 that is coupled to circuitry and configured to indicate when an acceptable electric connection has been achieved between all of the electrodes in the array and the skin of a subject, such as may be indicated by impedance falling below a threshold or current rising above a threshold. The indicator light 269 may be configured so it shines red when the positionable electrode 265 is energized but not in contact with a subject, yellow when some but not all electrodes 1 are in proper electrical connection with the skin of the subject, and green when all electrodes 1 are in proper electrical connection with the skin of the subject.

When employing the pen electrode and positionable electrode array embodiments, the waveform electrodes may be moved to any position on the body, onto which has been applied a layer of electrolyte foam or gel. In an alternative embodiment illustrated in FIG. 35A, the pen electrode 261 or positionable electrode array 265 may be used in combination with a pad or sheet 270 with an array of through holes 271 similar to that of the sensor system described above, but without the wiring of the flex circuit array described so far. The pad or sheet 270 may be made from a flexible insulating material, e.g., a polymer sheet or a foam pad, so that it may conform to the contours of a subject 273 and provide electrical insulation between the holes 271. Such a pad or sheet 270 would create a multitude of open wells bounded by the skin below and the holes 271 through the pad or sheet. In operation, these open wells may be filled with coupling interface material. In a preferred embodiment, at least some holes 271 may have an area of 10 mm$^2$ or less for use as waveform electrode wells, while holes intended for use as return electrodes may have a larger area. A tissue discrimination scan may then be conducted by alternatively positioning the conductor 262 of a pen electrode 260 in each hole 271 as illustrated in FIG. 35C.

Figure 35B:
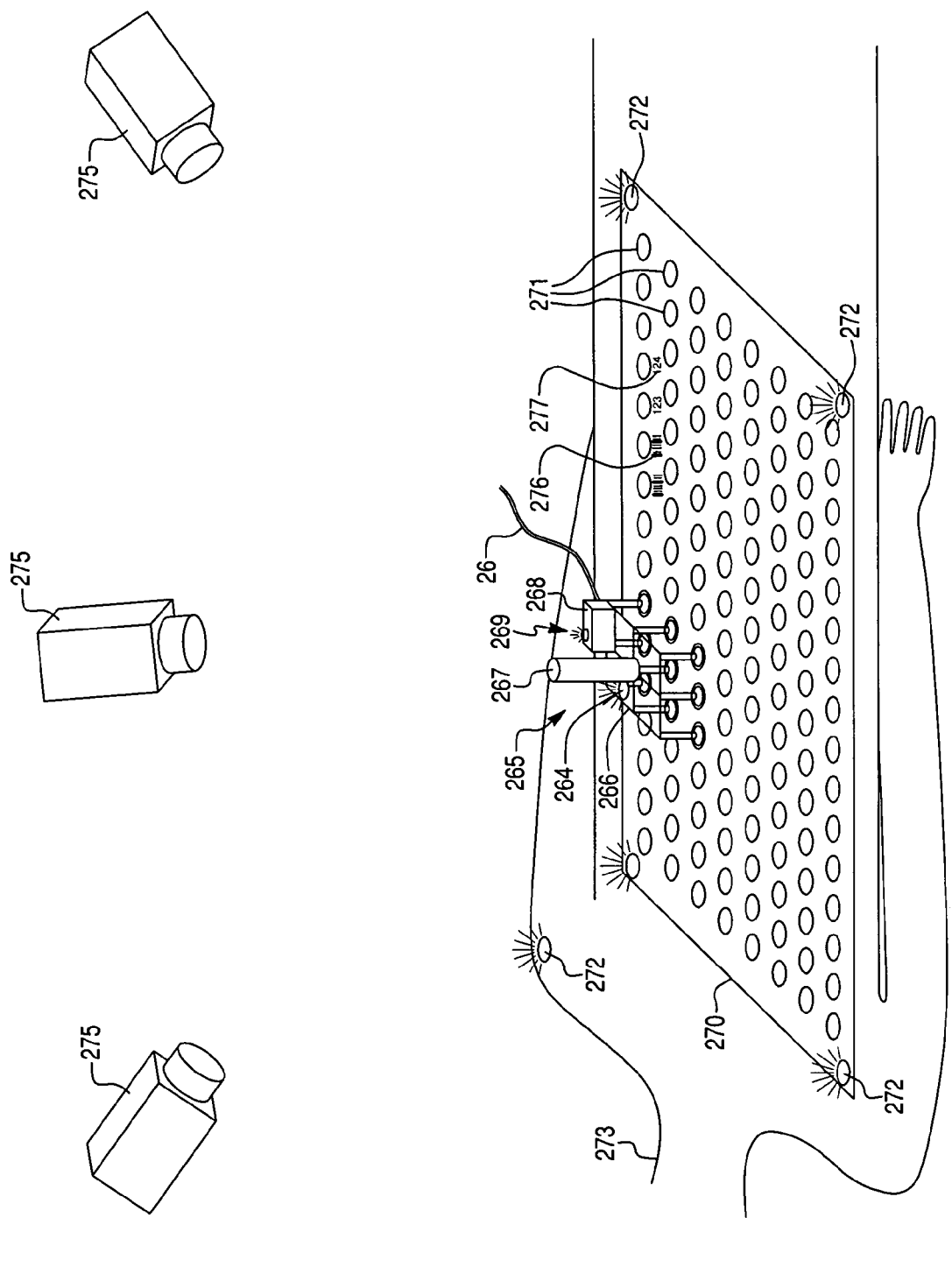
Figure 35C:
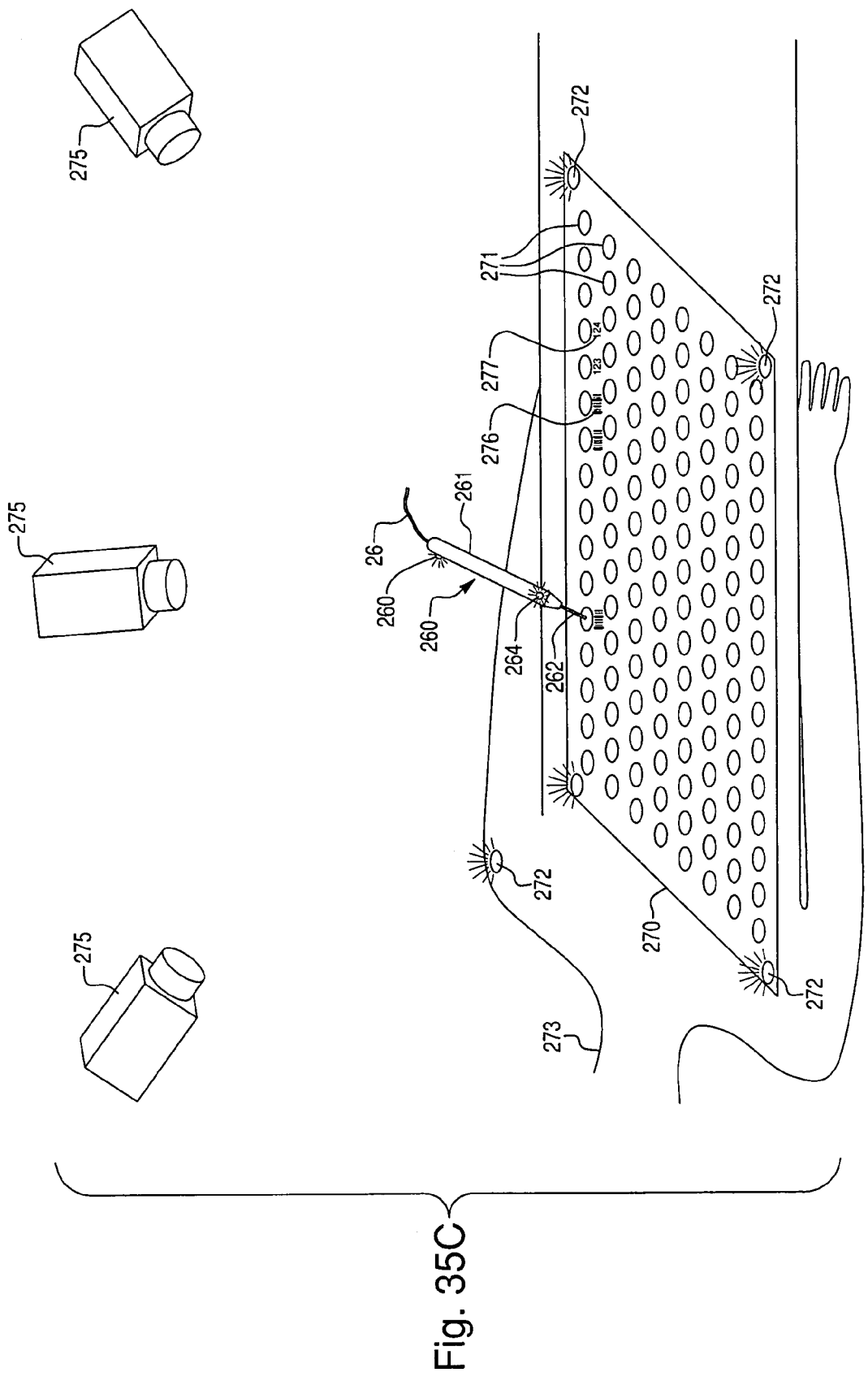

In an alternative form of this embodiment, a scan of a body may be conducted by applying the waveform electrodes 1 of the positionable electrode array 265 to the skin of the subject 273 in a plurality of the holes 271 in the sheet 270, as illustrated in FIG. 35B. After a scan is taken in one subset of holes 271, the positionable electrode array 265 may be moved to another subset of the holes 271 in the sheet 270. Thus, as illustrated in FIG. 35B, a scan using a positionable electrode 265 is accomplished by lowering the array of electrodes 1 into a matching set of holes 271 in the sheet 270 while observing the status indicator light 269 (if included in the embodiment)

to confirm that proper electrode contact has been established, followed by applying a waveform as described above. Similarly, a scan using a pen electrode 260 may be accomplished as illustrated in FIG. 35C by sequentially inserting the electrode portion 262 into holes 271 in the sheet 270 while observing the status indicator light 269 (if included in the embodiment) to confirm that proper electrode contact has been established, followed by applying a waveform as described above.

Contemplated within the present invention are any variations of the pad or sheet 270 that enables an electrode to make a single electrical connection with skin within a confined geometry as described herein. For example, contemplated embodiments include variations in which the pad does not include holes and the pad or sheet comprises a screen or honeycomb mesh of an insulating polymer material.

An embodiment of the pad or sheet 270 that does not include holes may be made of directionally-conductive materials and fabricated so that the pad conducts electricity perpendicular to the surface and presents high resistance to electricity flowing in directions parallel to the surface. When such a material is touched by an electrode on its top surface, electricity is conducted through the pad to the surface in contact with the skin of a subject. Since the pad material presents high resistance in directions parallel to the surface (i.e., in the plane of the pad or sheet 270), the electrified portion of the surface in contact with the skin of a subject is confined to an area approximately the same as the area of the electrode placed in contact with the top surface of the pad. Thus, the pad material itself serves the function of limiting the area of the skin contacted by the electrode. By using the appropriately sized electrode based upon the lateral resistance characteristics of the pad, the sensed area of the skin can be controlled so as to be less than approximately 10 mm$^2$. Examples of suitable directionally-conductive materials include insulator foam or polymer material in which thin conductors are oriented normal to the pad's surfaces. Such conductors may be fine wires, metallic fibers or whiskers, or carbon nanotubes.

Another embodiment of the pad or sheet 270 that does not include holes may be made of compressible foam which exhibits high resistance to electricity in the uncompressed state and relatively lower resistance to electricity when compressed. When an electrode is pressed into the top surface of a pad made of such material, the foam within the volume between the electrode and the skin of a subject is compressed, thereby lowering the resistance in that volume and presenting a limited electrified area on the surface in contact with the subject's skin. By using a small diameter electrode to contact and compress the foam, the high resistance characteristics of the uncompressed foam surrounding the point of contact will limit the area of the electrified foam in contact with the skin. In this manner, the sensed area of the skin can be controlled so as to be less than approximately 10 mm$^2$. An example of such a material is a foam of insulating material interspersed with granules or fibers of conductive material (e.g., metal powder or carbon nanotubes) at a density such that a path for electrical conduction only exists when the foam is compressed sufficiently to cause the conductive material to form electrical connections across void spaces.

Another embodiment of the pad or sheet 270 that does not include holes may be made of an insulating material, such as an organic polymer (e.g., polypropylene or polyethylene), interspersed with conductive pieces, such as metallic coins. In this embodiment, the conductive pieces fill holes in the insulating sheet, thereby providing a conductive path from one side of the sheet to the other. When placed in contact with the skin of a subject, such a sheet provides an array of electrode locations each of which may be individually energized or sensed by touching the top surface of the conductive piece with an electrode in a manner similar to that illustrated in FIGS. 35B and 35C.

A further element of the foregoing pad or sheet embodiments includes a layer or treatment on the skin-contacting surface to hydrate the skin. As described above, the purposes of the coupling interface material are to hydrate the skin and facilitate the conversion of electrical energy from electron-conduction to ionic-conduction at the skin interface. This coupling interface may be incorporated into the pad or sheet as a material layer, surface treatment, additional material (e.g., a conductive gel) or a combination of two or more of these approaches.

In another embodiment, the pad or screen 270 may be a screen or mesh of insulating material that can be laid over the skin and then filled with a layer of coupling interface material conductive electrolyte gel. A simple example of such a material is the polyethylene or polypropylene honeycomb mesh used for surgical applications. When laid on the skin of a subject, the polymer elements of the mesh act as electrical resistors inhibiting the flow of electrical signals from one opening in the mesh to the next. When a coupling interface material is applied over the mesh, each opening in the mesh may serve as an electrode well in the manner illustrated in FIGS. 35A-C. Alternatively, the mesh insulating material may be filled with uncured hydrogel, then subjected to UV light curing and produced as a sheet that may be converted to fit the electrode array. This converted sheet may be applied to the electrode array in advance of application on the skin surface or may be applied to the skin surface and the electrode array placed overtop of the in situ mesh interface material.

In each of the moveable electrode embodiments illustrated in FIG. 35A-C, as each electrode is moved from one location to another, its position may be registered by a camera system 275 and/or entered into the controller. Alternatively or in addition, the pad or sheet 270 may include indicators 276, 277 adjacent or near to each hole 271 through the sheet 270 that may be read or sensed to determine which of the holes is being interrogated by an electrode. Such an indicator may be in a form that can be sensed electronically at a short distance, e.g., a bar code 276, a tuned radio frequency (RF) oscillator (e.g., used in an RF identification (RFID) tag)(not shown) that may be sensed by an RFID interrogator, or other local sensible identification, observed by an operator, e.g., a number 277 or alphanumeric code that a user can record when inserting the electrode into a particular well, or a direct contact electronic indicator that will provide information to the sensor when touched, e.g., a contactor that provides a digital code or particular voltage that can be sensed when touched by the electrode. The hole position indicator 276, 277 provides a mechanism for quickly identifying and/or locating a hole 271 being used in a particular scan. The positionable electrode 265 or pen electrode 260 may include a sensor on it, e.g., a bar code reader or RFID interrogator (not shown), so that the hole indicator 276, 277 can be read when the positionable electrode 265 or pen electrode 260 is in the hole. With a direct contact sensor, the user touches the electrode to the contactor adjacent to a well before placing the electrode in the well. When the electrode touches the contactor, a signal, e.g., a particular voltage or a digital code, is communicated to the controller where it can be recorded, e.g., in a database for storing results of the tissue discrimination scan. The pad or sheet 270 may also include position fiducial markers 272 to permit a position sensor system 275 to locate the pad or sheet 270 in 3-D space, and thus its through-holes, within an external frame of reference or with respect to the body of the subject. The electrode may be handheld, such as the pen electrode 260 shown in FIG. 35A, or machine controlled, and may be an array of electrodes 265 or a single electrode 262. In this embodiment, the pad or sheet 270 may be inexpensive to produce in a variety of sizes, and therefore enable more flexible use by clinicians since it can be made in large sizes, conformed to the body, and cut to any dimensions or shape.

The roller and positionable electrode array, and pen electrode embodiments described above raise the potential need to register the position of electrodes to the position of the subject and/or an external frame of reference, such as an examination or operating room. As used herein, register refers to the locating, preferably precisely, of an object, such as an electrode, in 3-D space, typically relative to a frame of reference or relative to the position of another piece of equipment or the body of the subject. By registering an electrode in 3-D space, that positional information may be used to locate discriminated tissue, e.g., nerves, so that other diagnostic sensors, robotic surgery or machine-assisted therapy or surgical equipment may use that information in subsequent procedures. In cases involving surgery, particularly machine-assisted or robot-assisted surgery (e.g., image guided surgery), there is likely to be a need for an external registration system to locate the imaged nerves with respect to the operating equipment, the operating room and the patient. Similarly, a single roller electrode array assembly or a large number of roller electrode arrays, such as may be used to scan large areas, e.g., the back, may be combined with an external registration system. A suitable registration system may be a visual system such as two or more cameras 275 illustrated in FIG. 35A. In such a system, each camera 275 can detect and locate within space optical fiducial markers, such as colored dots or light emitting diodes (LED) 264, 272 placed on the object to be located (i.e., registered). For example, a pad or sheet 270 for use with a pen electrode 260 may include one or more position indicating fiducial markers 264 so that the pad can be registered within the frame of reference and, therefore, since the holes may be located in known sites on the pad, the location of each hole can be registered. As an alternative or augmentation to a visual registration system, a dimensional locating system may be positioned on or near the electrode and configured to provide positioning information to a host computer. Alternatively, fiducial marks (e.g., ink spots) may be left by the roller or the pen electrode that can be correlated to the image and to the external frame of reference.

In the pen electrode embodiment, position information of the pen may also be determined and recorded by a position locating system by including a fiducial marker 264 that may be positioned on or near the tip and/or end of the pen electrode 260 and configured to provide positioning information to a host computer. The use of a 3-D positioning system in conjunction with the pen electrode 260 may allow a clinician to free-scan the body of a subject. At each position that a measurement is taken, the positioning system can correlate the measurement data with the position on the subject, and thereby build up a scan of the tissue using essentially a virtual array in a manner similar to that employed with an electrode array assembly. The use of such a virtual array technique may obviate the need for an electrode array assembly, although it would require the clinician to apply the pen electrode 260 to the subject 273 many times to build up an image of discriminated tissue. Further, the clinician may use a pen electrode 260 to pre-screen a body area to locate an optimal placement of an imaging electrode array assembly, and then use the stored 3-D position information to correctly align the electrode array assembly to the subject.

Combining the roller electrode array embodiment with the pen electrode embodiments into a single system may allow the clinician to scan an extended or highly contoured portion of the body without the need for and expense of a large grid electrode array assembly that must be placed in a single location on the skin. Such combinations may also be used in combination with dimensional locating systems as disclosed above.

Figure 36:
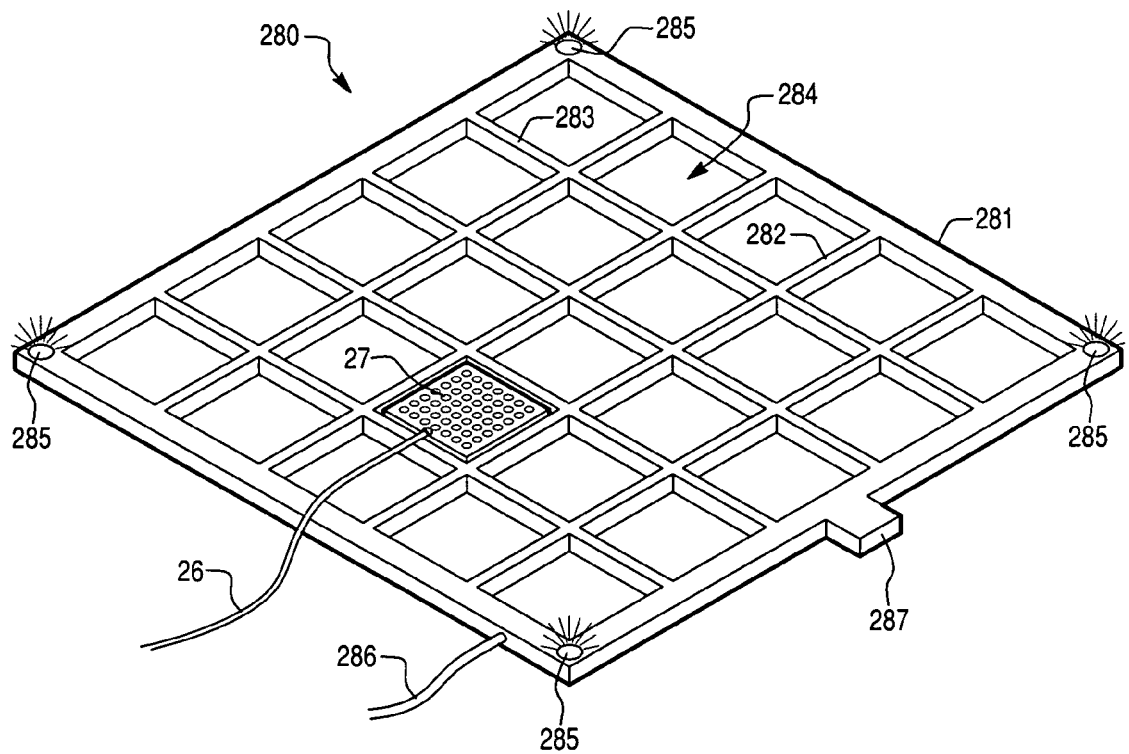
FIG. 36 illustrates a grid for positioning electrode array assemblies according to an embodiment of the present invention.

Another alternative embodiment to enable tissue discrimination and imaging of large aspects of the body, e.g., the back, without creating large and expensive electrode array assemblies, is to use a grid holder system 280 illustrated in FIG. 36, for positioning multiple standard sized (e.g., 60-100 electrode) arrays 27. Such a grid 280 may be as simple as a frame 281 enclosing horizontal and vertical cross members or slats 282, 283 to form a regular array of openings 284 into which an electrode array assembly 27 may be positioned. If the openings 284 are sized to approximately match the shape of the electrode array assembly 27, such as having the same shape but being slightly larger, the openings 284 can provide lateral support to minimize movement of the electrode array assembly 27, thereby holding them in a relatively fixed position and orientation with respect to the grid 280. Fiducial reference point markers, such as lights 285 (which may be LEDs, light bulbs, reflectors, colored dots, etc.) or other means may be included on the grid 280 to allow an external position sensor system, such as a set of cameras, to identify and locate in 3-D space particular known reference points on the grid 280. Software operating in the host computer may track which grid location and electrode is sampled as data are collected. This grid 280 may provide a reference system for the various scans using individual arrays 27, thereby permitting the scans to be correlated to provide results for the entire grid area. Electronics (not shown) may be provided on the grid 280 to automatically communicate to the controller the identity of the grid cell in which a measurement is being taken, such as by means of a cable 286 connected to the controller. A camera system, or other external means of registering data to a location on the grid, may also be used for registration of the array 27 within the grid 280. Alternatively, an operator may indicate which grid cell 284 is being scanned by entering a grid number into a computer. Software operating in the controller may implement display constructions to combine samplings from the entire grid into a correlated data set. The grid system could be flexible in size and conformation, such as by joining slats with pivoting connectors. In this embodiment a single return electrode may be used that may be repositioned at a distance appropriate for each grid location. Alternatively, the grid 280 may encompass one or multiple return electrodes 287 in its structure. With multiple return electrodes 287, the controller may select the appropriate return electrode for the grid location in use so that the appropriate return electrode to waveform electrode separation distance is used for each grid location scanned.

In another embodiment, the tissue discrimination system electrode array assembly may be combined or integrated with an ultrasound transducer to provide for simultaneously mapping blood vessels, bones and other tissues as well as nerve tissue. Signals from the electrode array assembly are processed by the systems according to the present invention, while signals from the ultrasound transducer are processed by an ultrasound imaging system as is well known in art. It is well known that major nerve plexuses are usually associated with major blood vessels. This anatomic relationship has enabled the use of ultrasound, which can image blood vessels, for placing continuous nerve block catheters in the vicinity of major nerves by keying off the position of blood vessels.

However, the ability to discriminate both vessels and nerves directly would be of great advantage for anesthesia purposes as well as other diagnostic and therapeutic procedures.

In various embodiments of the present invention, a single ultrasound transducer, two ultrasound transducers (enabling stereo imaging), or more ultrasound transducers (enabling 3-D imaging) may be mounted on, in or adjacent to the electrode array assembly. This embodiment may be used, for example, to detect a catheter in, or near, a blood vessel, locate its position with respect to surrounding nerves and monitor the activity of the nerves. This application would be useful in positioning regional anesthesia catheters in relation to targeted nerves. This embodiment would also permit mapping the nerves and blood vessels prior to arthroscopy, microsurgery, robotic surgery and image-guided surgery. Similarly, this embodiment, and the method of simultaneously conducting ultrasound and nerve scans would be useful in preparation for abdominal laparoscopy to help the surgeon avoid injuring the intercostal nerves.

In the embodiment combining ultrasound transducer(s) and ultrasound imaging system with the tissue discrimination system of the present invention, standard ultrasound transducers may be used. In some configurations, the ultrasound transducer may be configured to scan through the electrode array assembly, i.e., direct ultrasound through the array and into the subject. In another embodiment, a registration system (e.g., external structures or fiducial markers on the skin) may be used to register the ultrasound image with the nerve scan image so that the images can be obtained separately and then correlated, contrasted and/or combined into a single image or combined data set. In yet another embodiment, small ultrasound transducers, e.g., those based upon micro-electromechanical system (MEMS) actuators or miniature piezoelectric transducers, may be combined with the electrode array assembly to provide a single ultrasound array/electrode array assembly. In this embodiment, MEMS or miniature ultrasound transducers may be positioned in the interstitial spaces between electrode positions. In an alternative embodiment, the MEMS or miniature actuators may be positioned behind the electrodes within wells so that the electrode itself is the source of vibration and the coupling interface material (e.g., electrolyte gel) within the well acts as both the electric and acoustic coupling agent. Combining transducers within the electrode array assembly may eliminate the need to register the ultrasound and nerve images within an external reference system. Combined transducer/electrode array assemblies may also be used to discriminate tissue that is being imaged by the ultrasound. This embodiment may also employ coupling interface material that is applied over an area of the body so that the electrodes may be moved while taking readings. In this embodiment, the coupling interface material may be made suitable for use as an acoustic coupling material, permitting the same material to be used for both scans, which would facilitate simultaneous scanning with both technologies.

Figure 37:
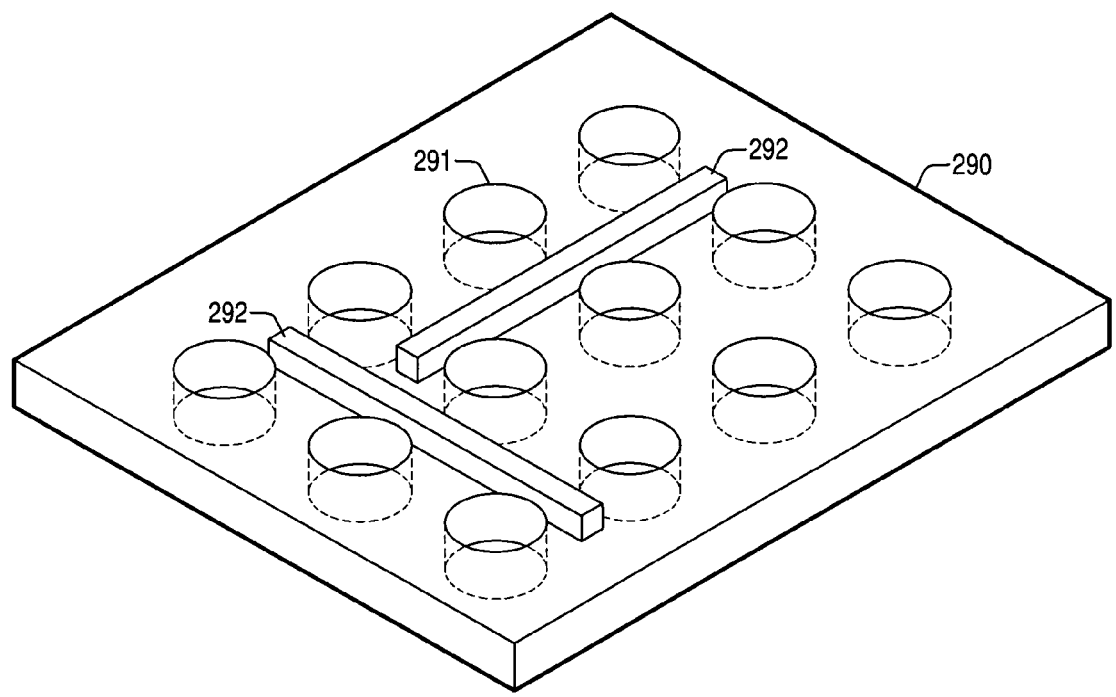
FIG. 37 illustrates a combined electrode array—ultrasound transducer array assembly according to an embodiment of the present invention.

In a further embodiment, illustrated in FIG. 37, an array of MEMS or small piezoelectric ultrasound transducers 292 positioned within the electrode array assembly 290 may be operated as an ultrasound phased array transducer as is well known in the ultrasound art. A phased array ultrasound transducer 292 comprises a number of transducers which are activated individually at controlled phase shifts (i.e., time-displaced signals) such that the sound waves from each transducer combine and interfere so as to generate a single focused beam that can be steered by adjusting the phase shifts among the transducers. In the embodiment illustrated in FIG. 37, the array of MEMS or small piezoelectric ultrasound transducers is positioned in the electrode array assembly 290 in a configuration that optimizes the phased array performance characteristics. For example, the array of MEMS or small piezoelectric ultrasound transducers 292 may be a linear array positioned between rows or columns of electrodes 291, a rectilinear array, or two linear arrays at an angle as illustrated in FIG. 37, e.g., a right angle (e.g., forming a cross) between two rows and two columns of electrodes 291. A linear array permits obtaining 2-D ultrasound images, while a rectilinear or two linear arrays at an angle permit obtaining 3-D ultrasound images, as is well known in the ultrasound art. In a further embodiment, MEMS or miniature ultrasound transducers within the electrode array assembly may be configured and operated in a phased array manner in order to focus on particular tissues discriminated in the scan, such as nerve structures identified by a nerve scan. In this way, clear ultrasound images may be obtained of particular tissues, such as nerves and/or of the structure near or surrounding those tissues, such as blood vessels or bone. This capability may offer therapeutic and diagnostic advantages when addressing nerve pain that is associated with or caused by structural (bone, tendon, cartilage, etc.) injury, inflammation, or impingement. For example, this embodiment would permit locating the precise position of spinal nerves in and around the spinal process and ultrasound imaging of the bone, disk and associated cartilage to determine sources of nerve injury. Similarly, the system may permit precise location of spinal nerves with respect to the spinal process, transverse process and vertebral body to reduce the risk of nerve injury during procedures like vertebroplasty.

Figure 23:
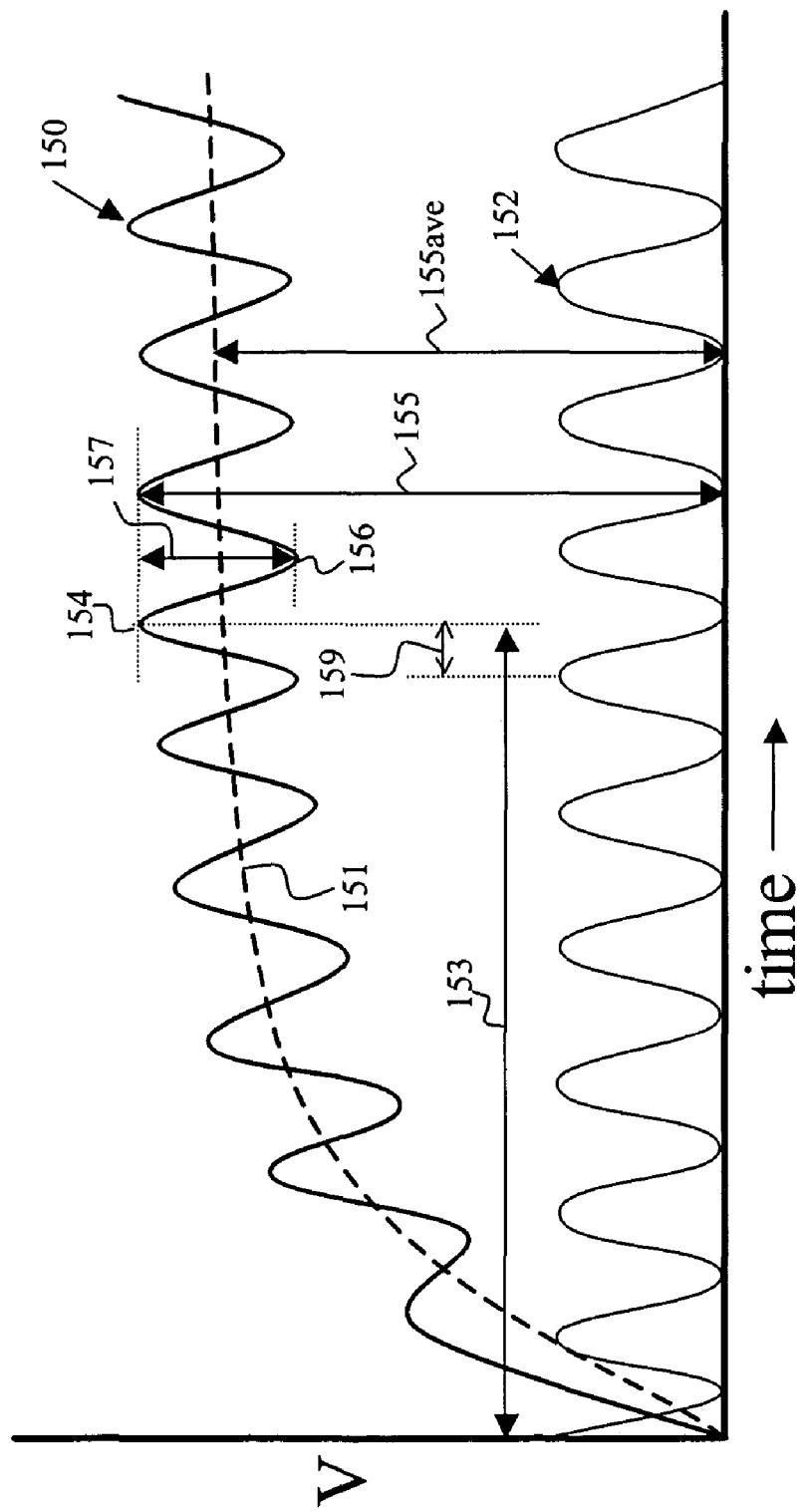
FIG. 23 presents a representative illustration of the changes in voltage over time in response to an applied controlled current waveform that may be sensed by an embodiment of the present invention.

The effects of tissue on the applied waveform are illustrated in FIG. 23 which illustrates data that could be obtained from a single electrode according to various embodiments of the present invention. Starting at time 0, a signal, e.g., a sine wave 152 of a particular voltage or current, at a controlled level, e.g., between 0 V and a positive voltage or negative voltage, is applied to the skin of a subject. Measurements of the voltage or conductance at the return electrode are graphed at data line 150. (It should be noted that the amplitude of the applied waveform and the measured values are not shown to the same scale in FIG. 23.) Typically, if the applied waveform is monophasic, the measured voltage or conductance rises over time, punctuated with peaks 154 and valleys 156 corresponding roughly to the applied signal.

The recognition that a significant capacitive component plays a role in the preferential conduction of electrical fields along axons implies that frequency relationships are important. This is in fact what has been observed by the inventors and others. For example, FIG. 19 displays data gathered by Johng et al. (Johng H M, Cho J H, Shin H S, Soh K S, Koo T H, Choi S Y, Koo H S, Park M S: Frequency Dependence of Impedances at the Acupuncture Point QUZE (PC3). IEEE Eng. Med. Biol. 2002; 33-6) of measured skin impedances with signals of different frequencies above an acupuncture point or acupoint (bottom line) and slightly removed from the acupoint (top line). It is known that acupuncture points are located on the skin overlying nerve structures, e.g., nerve branches and nerve plexuses. Thus, the data graphed in FIG. 19 contrasts the impedance versus frequency response of skin above nerves and above other non-nerve tissue. FIG. 19 reveals that the largest difference in impedance between an acupuncture point and a non-acupuncture point is exhibited between approximately 1 kHz and approximately 2 kHz. Thus, in order to maximize discrimination (i.e., enhance resolution) of nerve from other non-nerve tissue, the applied signal should be in this range. FIG. 19 also shows that other non-nerve and nerve tissue exhibit different rates of change in the measured impedance versus frequency ($\Delta Z/\Delta F$) which provides another mechanism for discriminating tissues with the present invention as described in more detail herein. FIG. 19 also shows that as the signal frequency is increased beyond approximately 10 kHz, the difference in impedance measured on the skin above an acupuncture point and a non-acupuncture point trends toward the same value, which means that tissue types will be less discriminated based upon measured impedance values for waveforms in the high kilohertz to megahertz range such as employed in EIT systems.

Figure 20:
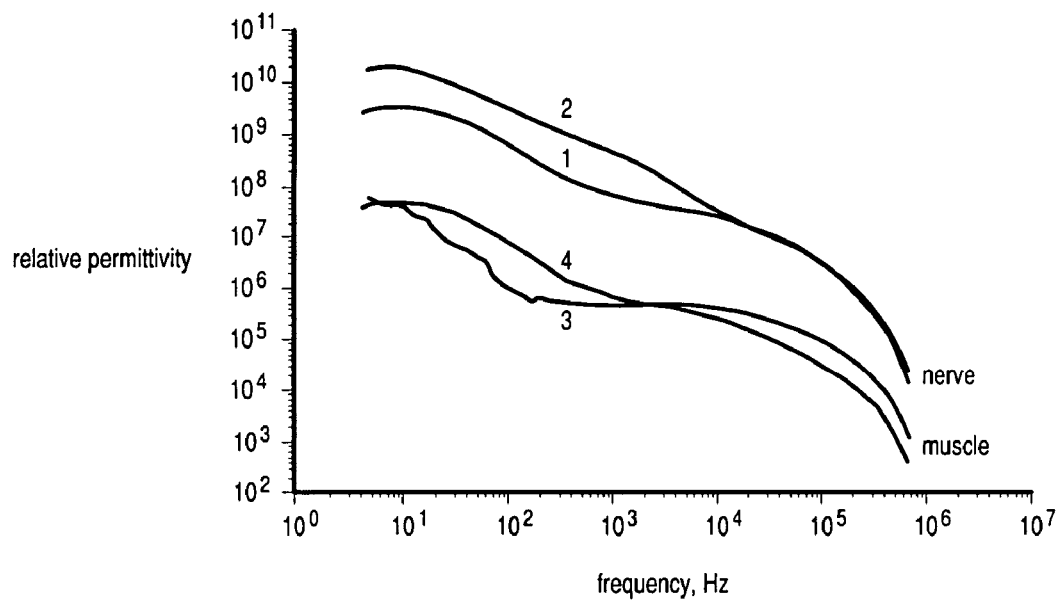
FIG. 20 presents relative permittivity data measured through electrodes applied across muscle and nerve tissues as a function of applied signal frequency.
Figure 21:
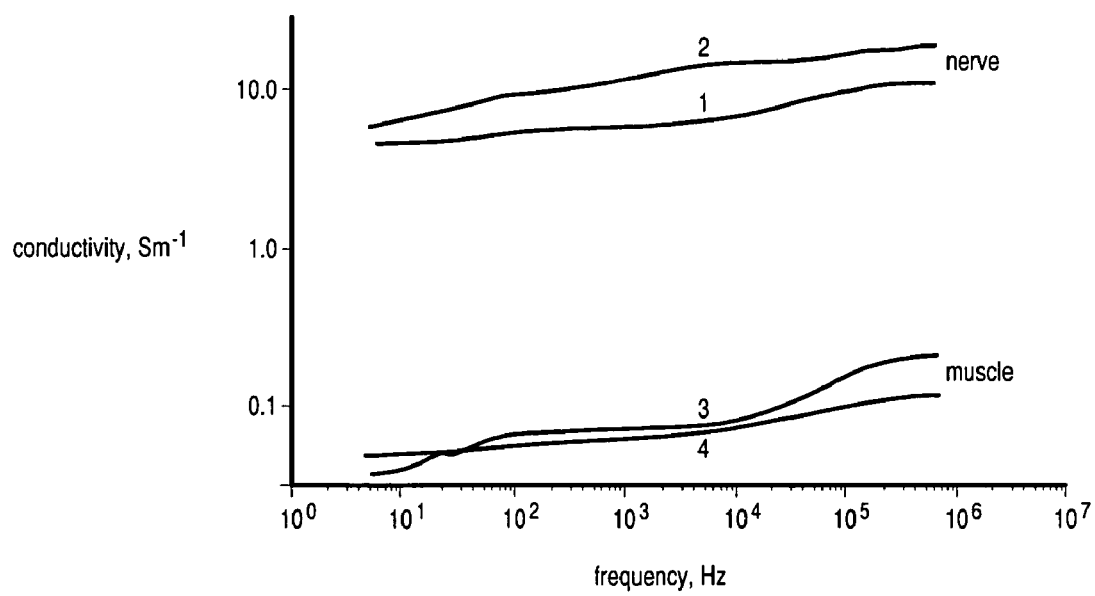
FIG. 21 presents relative conductivity data measured through electrodes applied across muscle and nerve tissues as a function of applied signal frequency.
Figure 22:
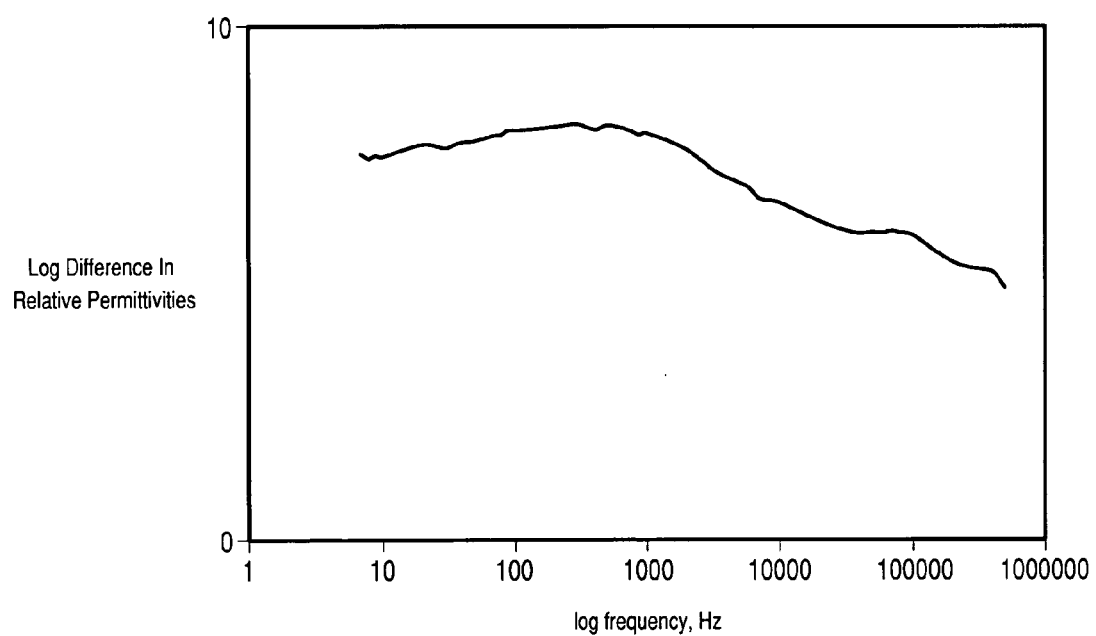
FIG. 22 presents calculated differences in relative permittivity between nerve and muscle tissue as a function of applied signal frequency.

Similarly, other electrical characteristics which may be measured by the system of the present invention exhibit a frequency dependency which indicates that tissue discrimination is best conducted in the range of between approximately 1 kHz and approximately 2 kHz. For example, FIG. 20 plots the dependence of relative permittivity of nerve and muscle to signal frequency, and FIG. 21 plots the dependence of conductivity of nerve and muscle to signal frequency, based upon data gathered by Prokhovov et al. (Prokhovov E, Llamas F, Morales-Sanchez E, Gonzalez-Hemandez J, Prokhorov A: In Vivo Impedance Measurements on Nerves and Surrounding Skeletal Muscles in Rats and Human Body. Med. & Biol. Eng. & Comput. 2002; 40: 323-6). By plotting the difference between the relative permittivity for nerve and muscle as a function of frequency, as illustrated in FIG. 22, an optimum frequency range for discriminating between nerves and muscle based upon permittivity can be determined. Referring to FIG. 22, it can be seen that discrimination based upon permittivity can best be achieved in frequency range of approximately 500 Hz to approximately 2000 Hz, with a broad peak in the range around approximately 1000 Hz.

FIG. 23 illustrates various phenomenon employed by the inventors, using a monophasic waveform, to locate, discriminate and image tissues, particularly nerves, using the apparatus and methods of the various embodiments. While the current waveform 152 varies between approximately zero amps and the controlled level, the voltage waveform 150 tends to be biased so as to exhibit an average voltage 151 (either positive or negative). (Note that the amplitude of the current waveform 152 and the voltage waveform 150 are not shown to scale in FIG. 23.) Based upon experimentation and analysis, the inventors believe that the rising trend in line 151 may be due in part to tissue capacitance, and thus reflect the charging of capacitive structures that exists within the body, particularly within nerve cells. In particular, it is believed that nerves exhibit a capacitance between individual nerve cells isolated from each other and the body by the epineurium. The capacitance of nerve fibers appears related to the size of the nerve (e.g., number of nerve cells within the nerve), the health of the nerve, and other aspects related to neuroanatomy and neurophysiology. Axons vary in diameter from about 6 microns to 30 microns. Consequently, the individual axons will demonstrate different capacitances based on both their length and diameter. When the present invention fixes the length by electrode spacing, the diameter should be a primary effecter on individual axonal capacitance. Consequently, measurement of the voltage waveform in the vicinity of nerve fibers enables the collection of useful information about the nerve in addition to its location.

Figure 24:
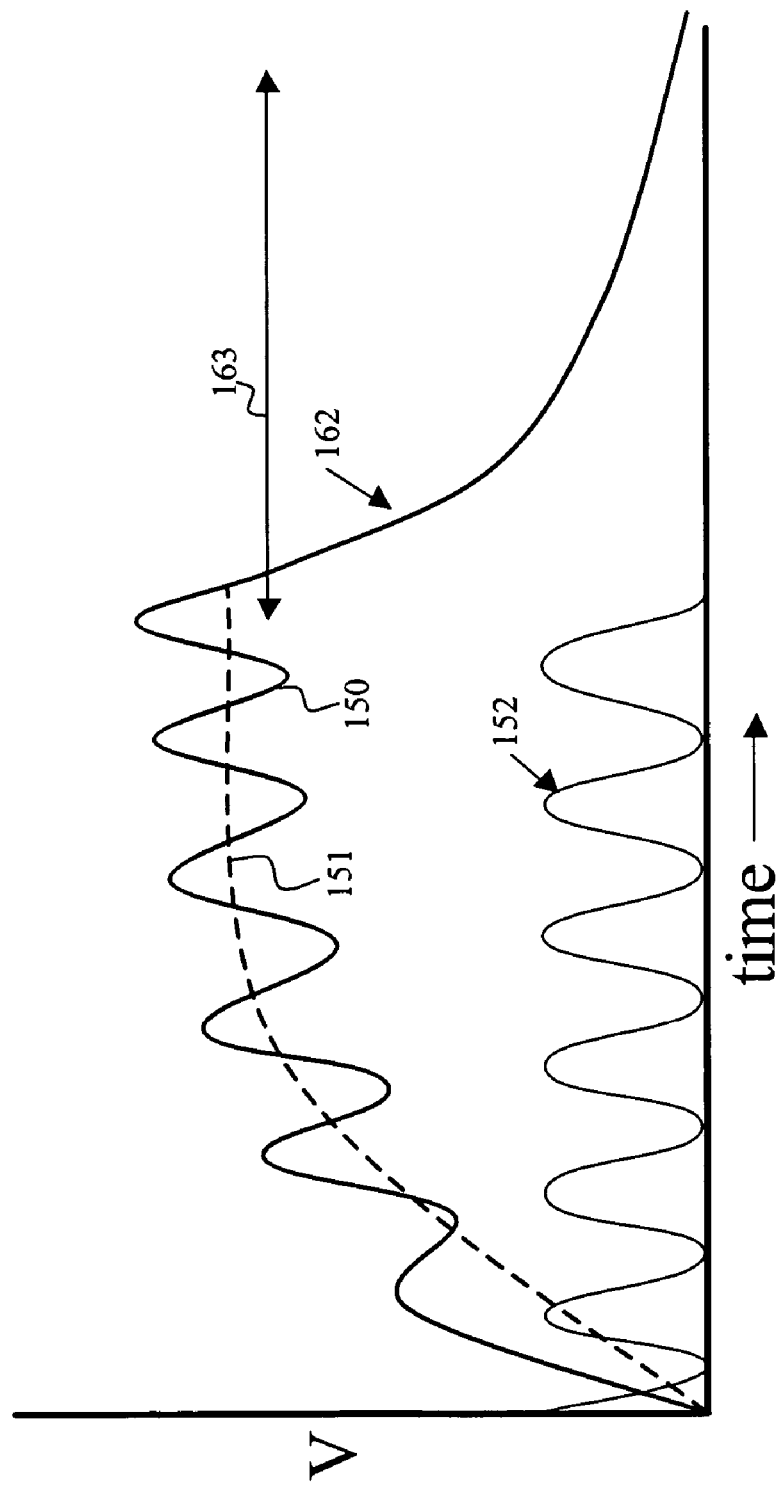
FIG. 24 illustrates the voltage signal decay that may be sensed by an embodiment of the present invention once the applied controlled current waveform is terminated.

Data line 150 illustrates a number of parameters that may be measured or calculated and used for various nerve imaging and diagnostic purposes. The maximum signal level 154 reflects the maximum voltage measured after the waveform has been applied for sufficient time 153 for the average measured voltage 151 to reach an approximately steady state. Line 151 represents the average voltage received over time. This maximum voltage level 154 or 151 may be used to determine or estimate a number of characteristics of the nerves underlying the skin, including by way of example but not by way of limitation: the size of the underlying nerve, a relative indication of nerve health and/or function, nerve injury, the depth or distance of the nerve from the electrode, and the presence or absence of major nerves in the vicinity of the electrode. Additionally, the maximum voltage level 154 may be used to calibrate or contrast the efficiency of various electrodes, e.g., to detect an electrode with poor electrical coupling to the skin. The magnitude of the difference 157 between peaks 154 and valleys 156 indicate the relative admittance of the underlying tissue, including in particular nerves in the vicinity of the electrode. The difference 157 as a measure of relative admittance may be used to determine or estimate a number of characteristics of the nerves underlying the skin, including by way of example but not by way of limitation: nerve activity, nerve health and/or function, the depth or distance of the nerve from the electrode, and the presence or absence of major nerves in the vicinity of the electrode. Other useful features include the time 153 to reach the maximum voltage level 154 and the phase shift 159 between the current and the voltage data. Similarly, the change in the measured voltage waveform after an applied current waveform is terminated may also yield important information about the underlying tissue, such as the rate of decay 162 of the developed potential (voltage) and the time 163 for the voltage to return to zero, as illustrated in FIG. 24. These various parameters may be used singularly or in combination with one or more other characteristics to distinguish tissues, for nerve imaging and/or for nerve diagnostic purposes. Further, the collection of measurement data and the calculations in the preferred embodiment may be performed by automated systems which can translate the various electrical characteristics of the measured waveform to deduce information about the tissue underlying the electrodes.

The aforementioned description of the physiological phenomena upon which the present invention is based reveals how the present invention differs significantly from EIT in the system elements, discrimination methods, measured data and useful results. In EIT, an external electric field is applied to a subject, such as by means of a first electrode applied to the head or upper torso of the subject and second electrode applied to the feet or legs of the subject, and a voltage between a second pair of electrodes is measured at an intermediate location (i.e., a tetrapole system). The electrical feature measured is typically voltage. EIT is premised upon the conventional belief that electric fields do not follow preferred paths through tissue and that conduction is primarily by way of extracellular fluids. So premised, EIT methods typically employ high frequency signals, such as in the hundreds of kilohertz to megahertz range, and large sized electrodes. The relatively large electrodes used in EIT, which are typically standard ECG electrodes and thus much greater in area than 10 mm$^2$, integrate and average any local differences in impedance. EIT employs tomography back-projection analysis algorithms to attempt to image tissue structures based upon assumed effects of the tissue on the electric field passing through a homogenous body. No useful information can be obtained from the measured voltage data site-to-site without performing the back-projection analysis.

A theoretical problem exists with the tetrapolar electrode arrangements in that, with a current distribution model revealed by the present invention, the classic assumptions regarding the distribution of potential on the skin surface are inaccurate. Assuming a smooth, prolate ellipsoid distribution of current flow through a bulk conductor leads to the prediction that such electrical fields will be associated with a smooth distribution of equipotential lines on the conductor surface and that the distribution of surface potential may be directly related to the underlying total current flow. With an anisotropicity that dictates a right angle relationship, the surface potential distribution will not be smooth, but will demonstrate discontinuities, particularly in regions where the current flow transitions from a track coursing normal to the surface to a track coursing roughly parallel to the surface. This transition will be reflected by more closely spaced equipotential lines on the surface at some distance from the current carrying electrodes and will be related to the preferential conductance pathway depth. As a consequence, surface potential measurements performed between the current carrying electrodes will demonstrate variability that is most marked in these transition regions.

In contrast to EIT, the present invention employs waveform electrodes of approximately 10 $mm^2$ or smaller, which will detect and distinguish the local variations in impedance on the skin which correspond to differences in the impedance of underlying tissue. Also, the present invention preferably employs applied signal frequencies in the range between approximately 500 Hertz and 2500 Hertz, more preferably between 1500 and 2000 Hertz, frequencies which on the same order of magnitude as the time course of voltage-gated channels. (In this regard, it is worth noting that the type of signal generator required to produce the megahertz signals employed in EIT is significantly different in electronic design from the ~1-2 kilohertz signal generator employed in the present invention.) Typically, the calculated electrical characteristic in the present invention is impedance, although other electrical parameters may also be considered as described above. As a further difference, the present invention measures the local effect upon the waveform applied across the waveform and return electrodes, and the intervening tissue, in order to determine the local impedance (or other electrical characteristic) at each electrode location—no back-projection algorithms are employed. Thus, a useful display of data from various embodiments of the present invention may simply be a graph or tabular listing the measured impedance of each electrode in an array—no back calculation of field effects is required to image underlying structures since site-to-site differences are the key measurement aspect.

As will be appreciated by one of skill in the art, while the present invention and EIT technologies differ significantly in physiological and physical characteristics, the data produced by these different technologies may be combined to provide added information about tissues. For example, EIT primarily measures field transmissions (i.e., permittivity) through tissue while the present invention preferentially measures tissue ionic transmission characteristics (e.g., impedance). As another example, Brown, et al. in Blood Flow Imaging Using Electrical Impedance Tomography, (Clin. Phys. Physiol. Meas. 1992; 13 suppl A: 175-9) discuss the use of real time EIT to discern the flow of blood through the vascular system. By combining the techniques of EIT, which can discern blood flow, with nerve imaging by the present invention, both blood vessels and nerves may be distinguished using the same electrode array assembly to provide a more complete depiction of the underlying neurovascular anatomy. Thus, an embodiment of the present invention combines EIT with tissue discrimination data according to the present invention to yield information based both on intracellular and extracellular conductive paths and phenomenon. Such combination of EIT and tissue discrimination according to the present invention may be accomplished by conducting both scans using the same electrode array assembly or by using data registration to permit 2-D or 3-D correlation of data from the two technologies to yield a combined image.

In another embodiment, results of EIT scans and tissue discrimination scans according to the present invention may be combined to enhance the EIT image by identifying anisotropies, most notably nerves, within the scanned tissue so the anisotropic effects may be subtracted or otherwise removed from or compensated for in the EIT data. Thus, tissue discrimination data may be used to image anisotropic features, such as nerves, and to allow EIT calculations to compensate for such features in the back-projection algorithms. It is expected that the result of such a combination will be a more accurate EIT image since it is believed that a large source of error in EIT is the effect of electrotonic nerve conduction upon electric field distribution in tissues.

In another embodiment, the methods of the present invention are combined with EIT technology and/or other imaging technologies based on different physical phenomena, such as X-ray (e.g., a CT scan), magnetic resonance imaging (MRI), positron emission tomography (PET), and ultrasound. It is expected that combining imaging results from different physical phenomena, which interact with tissue in different ways, may provide improved discrimination and resolution of tissues compared to any single imaging technology. This embodiment may be particularly useful in identifying and locating breast cancer tumors where the different phenomenological imaging technologies can be combined to more clearly discriminate tumor from healthy tissue.

For the purposes of providing an easy to understand display, the minimum and maximum of a display of the measured admittance or voltage may be scaled to an arbitrary range, e.g., from 0 to 1 or from 0 to 100%, or any other scale. Normalizing data for display may also be accomplished with colors or shaded displays where electrode locations or areas featuring relatively stronger signals are indicated with lighter colors or shades compared to electrode locations or areas featuring relatively weaker signals.

It is generally appropriate to limit the magnitude of the applied signal (e.g., voltage) to a maximum based upon a number of physiological limits. For most applications, of course, the waveform must be limited to physiologically safe values, and appropriate circuit breakers or voltage/current limiting circuitry may be included to ensure the applied waveform remains within safe values, even in the event of equipment faults. Such safety limits may vary depending upon the location of the electrodes on the body and the presence of other nearby equipment. Secondly, the applied waveform will normally be maintained below a level that may cause pain and/or direct stimulation of the nerve. One of the advantages of the present invention over the prior art is its ability to scan and locate nerves without the patient discomfort of nerve stimulation. Thirdly, the applied signal will generally be limited based upon the sensing circuitry. Circuits designed to measure millivolts and milliamps may exceed their range of accurate readings above certain values, so it will be important to maintain the waveform parameters below such levels. Fourthly, the electrophysiological response of body tissues may change as the waveform values exceed certain thresholds. By maintaining the applied waveform within a range where tissue responses are predictable, e.g., exhibiting linear behavior as a function of signal level, the accuracy of readings may be enhanced. Waveform values that exceed a circuit or physiological limit are sometimes referred to herein as reaching the rail or "railed," meaning that the value has exceeded some limit.

In addition to measuring the waveform across individual electrodes and a return electrode over time to obtain the data discussed above, the various measurements obtained for one electrode may be compared to those for each of the other electrodes in the array. Such electrode-to-electrode comparisons are useful in detecting the location of nerves according to an embodiment of the present invention, as well as providing other diagnostic information on nerve physiology. In one embodiment, the average detected signals (e.g., impedance Z or maximum admittance Y) for each electrode in the array may be scaled appropriately and graphed. Such a presentation, as illustrated in FIG. 26, shows the relative signal across a row on the array of electrodes, providing a simple indication of the presence of a nerve 13 beneath the array as a peak or valley in the measured or calculated signal, such as the dip 180 in impedance Z. As shown in FIG. 26, dermally projecting axons 10 have been found to extend from nerves 13 toward the skin 2 at an approximately right angle to the skin 2, thereby providing a preferential conduction path, i.e., point of low impedance Z, at right angles to the skin 2. Thus, the electrode directly over nerve 13, namely electrode #6 in FIG. 26, exhibits lower impedance Z compared to adjacent electrodes even though the path length from adjacent electrodes to the nerve 13 is not significantly different. This characteristic of nerve axons simplifies nerve discrimination and location when the electrodes are constrained in area (e.g., <approximately 10 $mm^2$). The crossing point of a nerve and a row in the electrode array assembly is found by identifying the electrode exhibiting the lowest impedance (or highest permittivity, highest conductivity, etc.). By aligning results for each of the rows in the array on a display, the path of a nerve may be traced from valley to valley for impedance (or peak to peak for characteristics like permittivity and conductivity) across the array. Such an analysis can be readily accomplished visually by displaying a matrix of values, or calculated using Microsoft Excel® or similar software, though more sophisticated analysis software is preferred.

Figure 27:
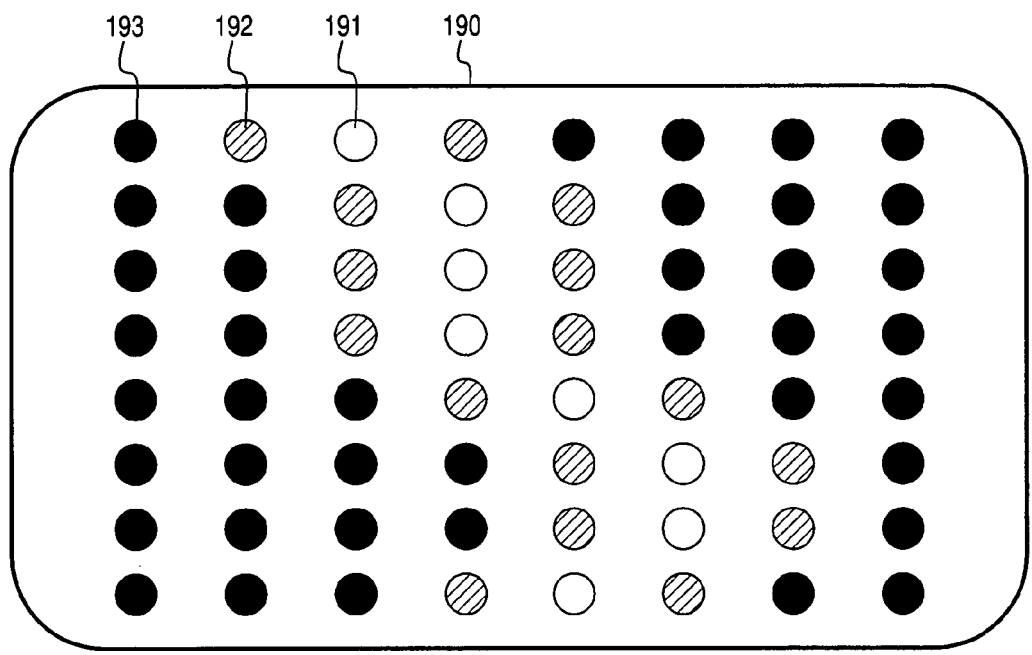
FIG. 27 illustrates an embodiment of the present invention where a sensed signal is displayed as spots or lights of varying intensity.
Figure 28:
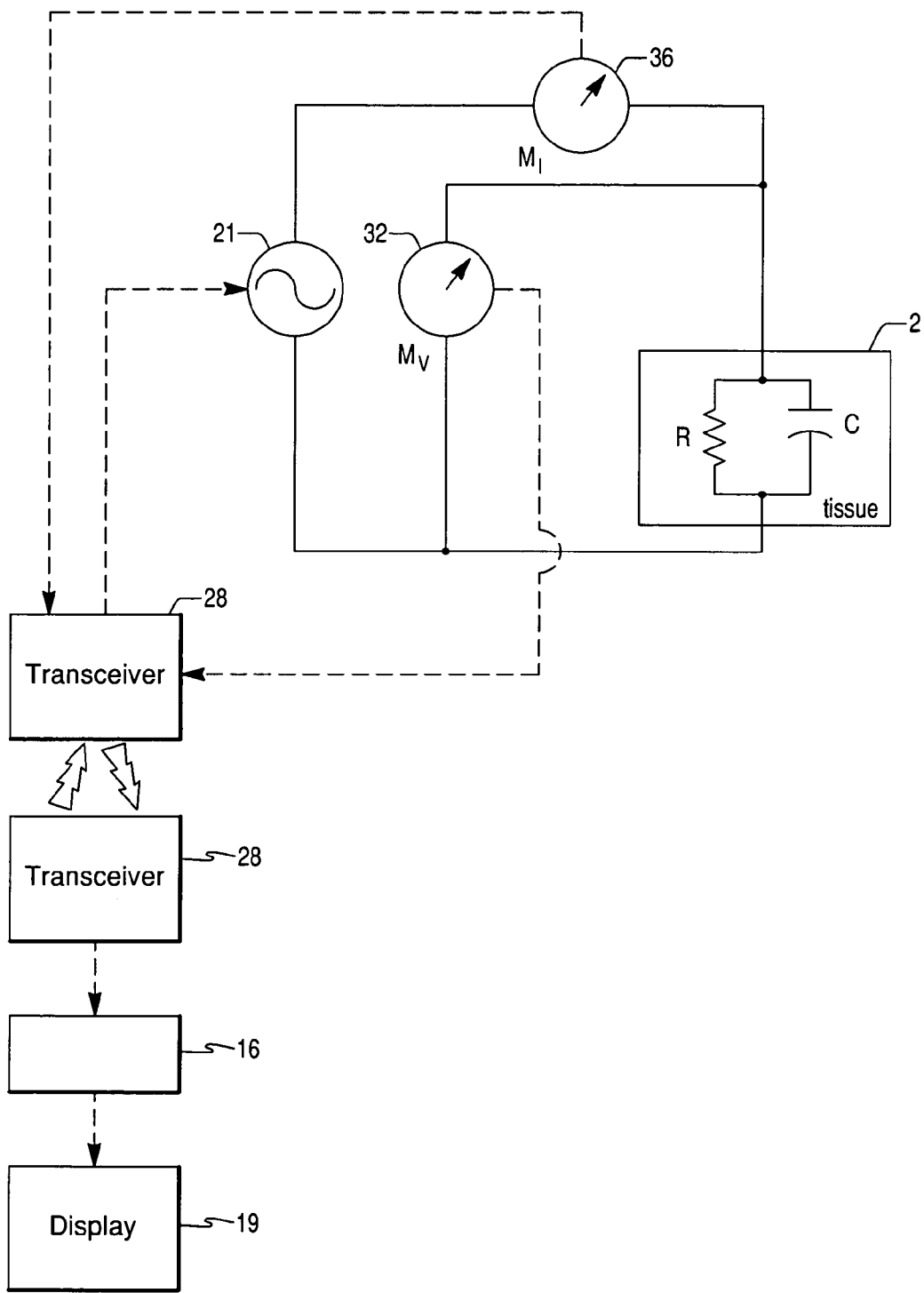
FIG. 28 illustrates a functional block diagram of a wireless embodiment of the present invention.

While a linear representation of the measurement data across the array provides obvious usefulness, data analysis and presentation can be further enhanced. Using color (or gray-scale) displays to indicate received signal magnitude, recorded signal values from all electrodes may be presented in a 2-D display 190, such as illustrated in FIG. 27. Instead of presenting this display on a computer terminal, an alternative configuration comprises small illuminators 191, 192, 193, e.g., LED, positioned on the top surface of each electrode in the array to provide a direct indication of the underlying nerve. As illustrated in FIG. 27, indicating measured signal strength with a relative luminosity of each illuminator can provide a simple yet effective display of underlying tissue. For example, if a relatively strong signal is indicated with a relatively light illuminator 191, a moderate signal is indicated with a moderately dim illuminator 192 and a weak signal indicated with a dim illuminator 193, the path of the underlying tissue driving the signal can be viewed directly.

While the first order processing of data described above discriminates tissues such as to disclose the location and pathways of nerves, further refinements of this measurement data presentation may be made using statistical analysis of the data to provide a topographical display. As will be explained more fully herein, contours of admittance (or voltage, impedance or other measured or derived parameters) across the area of the array may be estimated using interpolation, e.g., linear, geometric or cosine interpolation. Further, statistical analysis of the data may be used to enhance signals that exceed noise so as to more clearly reveal the position of nerves beneath the array. Alternative methods for analyzing the data across the array are disclosed below.

Figure 41:
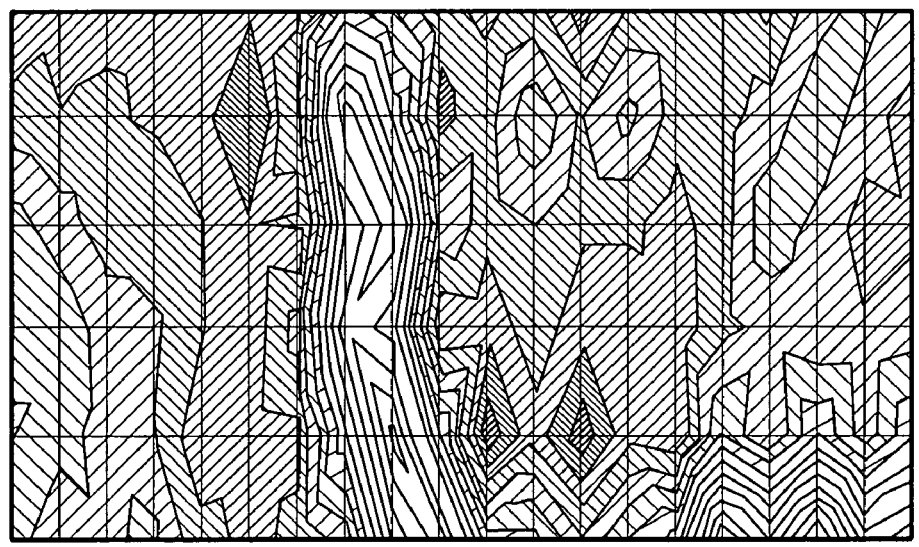
FIG. 41 shows a color coded display of tissue discrimination data according to an embodiment of the present invention, this image revealing the location of the right interscalene brachial plexus.

By indicating greater received signals (e.g., indicating lower impedance) in lighter colors and weaker received signals in darker colors, the path(s) of nerve tissue can be readily perceived. FIG. 41 shows a representational display of a scan of the right interscalene brachial plexus. As can be readily seen in this figure, higher signal values—in this instance the measured value is admittance—are normalized and inverse impedances (admittances) are shown in lighter color, which appears to make peaks out of valleys, and consequently, the path of the brachial plexus is readily apparent.

Figure 42:
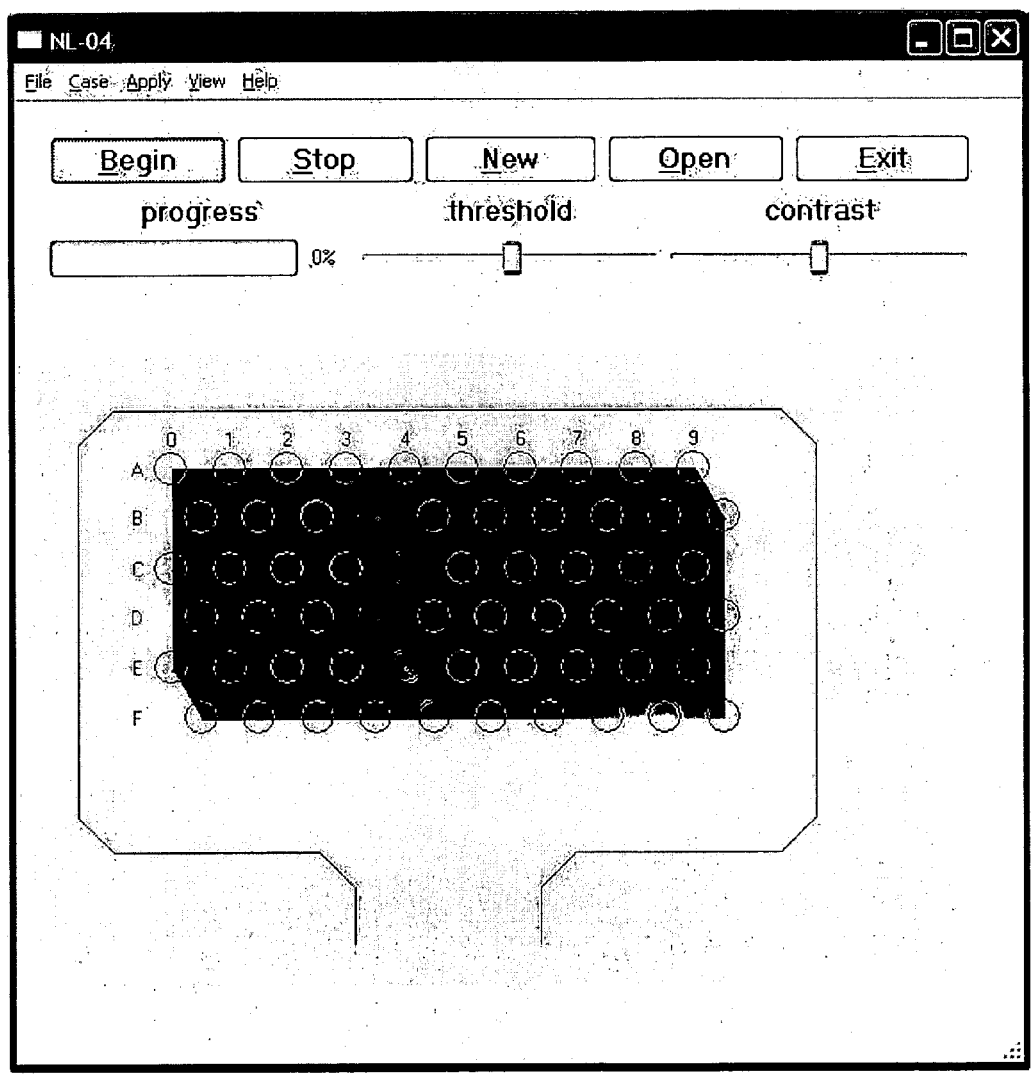
FIG. 42 shows a screen shot of a display of tissue discrimination data according to an embodiment of the present invention.
Figure 43:
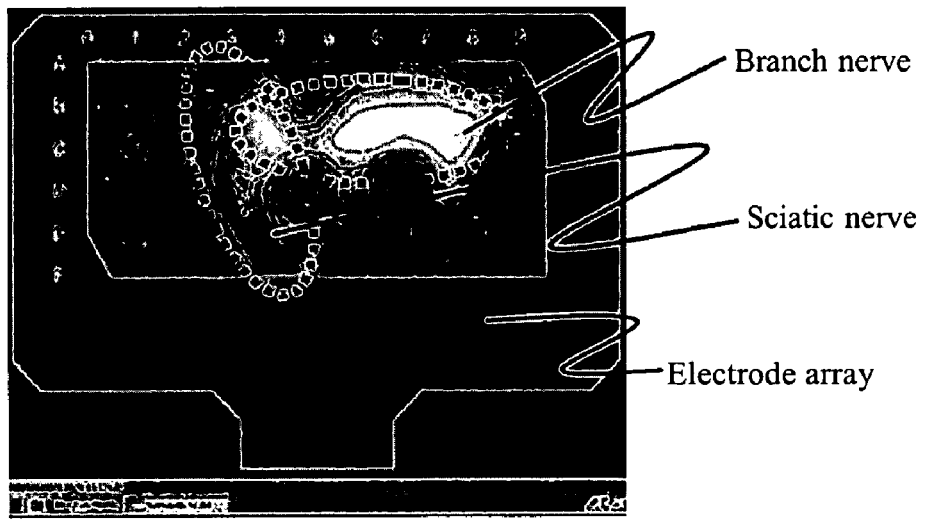
FIG. 43 provides a screen shot of a data display from an embodiment of the present invention imaging a portion of tissue of a subject.
Figure 44:
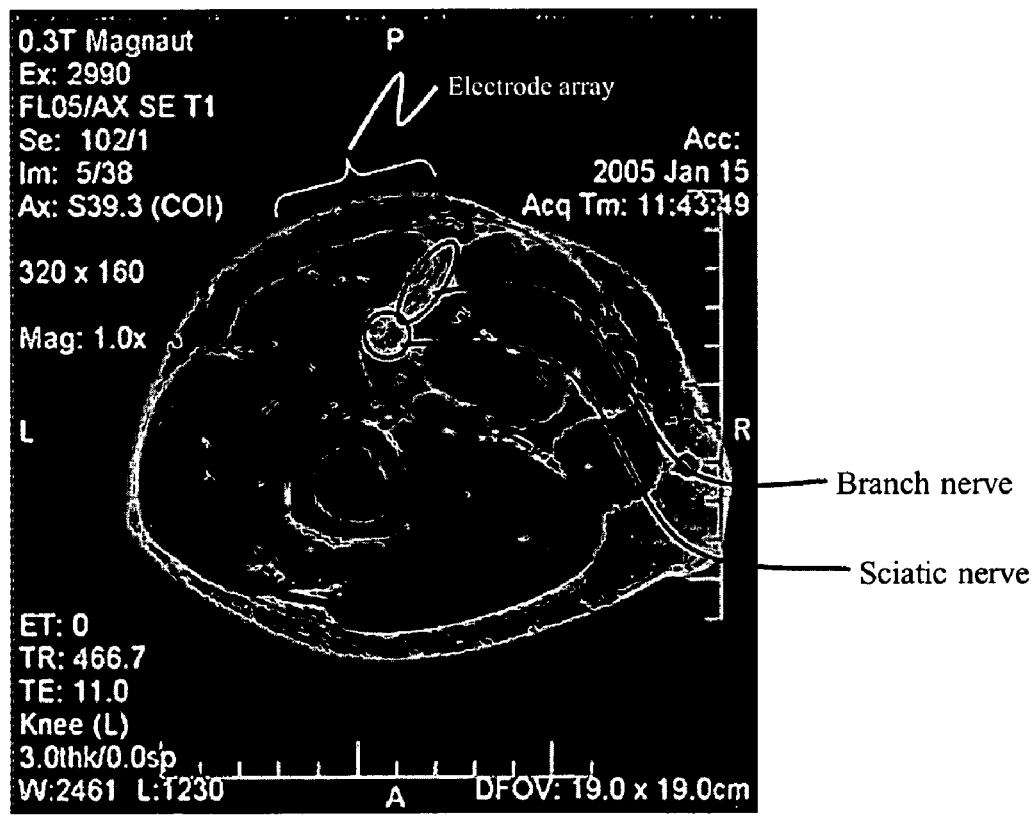
FIG. 44 shows a magnetic resonance image (MRI) of the same tissue as imaged in FIG. 43, which is rotated ninety degrees to the plane of FIG. 43.
Figure 45:
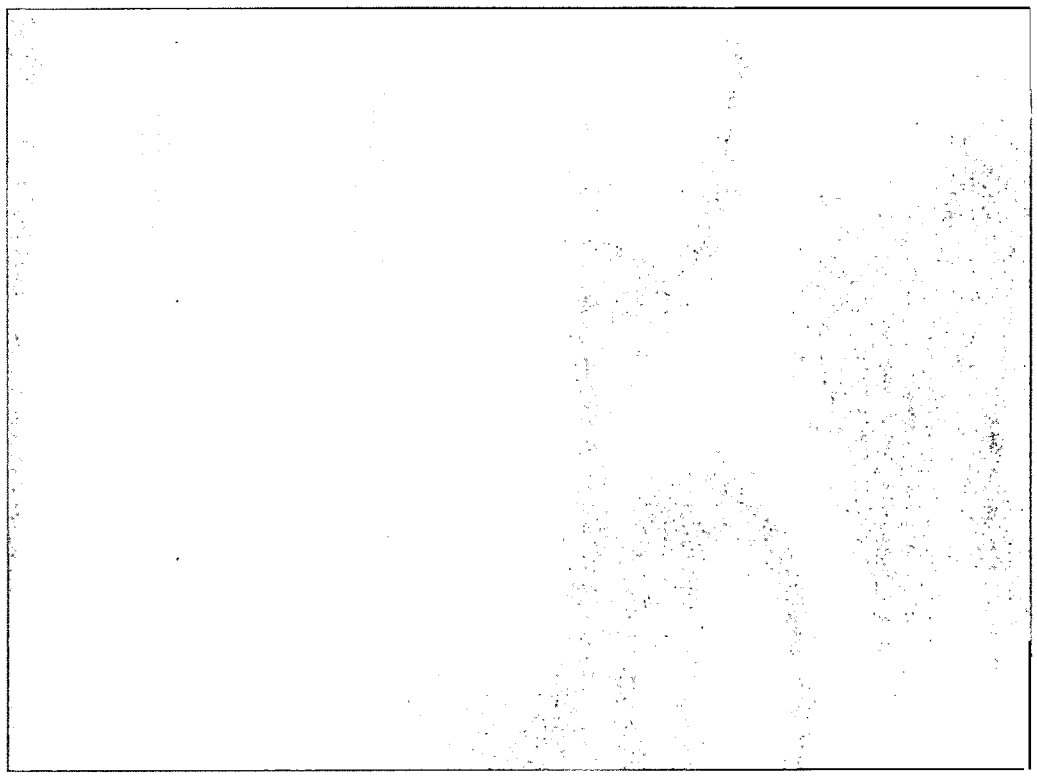
FIG. 45 shows an alternative display of tissue discrimination data according to an embodiment of the present invention, this image revealing the location of the right infraclavicular brachial plexus.

Using the various data analysis techniques described herein, the fidelity and usefulness of the data displays can be enhanced to meet the needs of the clinician. For example, a simple image of a nerve relative to the electrode array assembly is illustrated in FIG. 42. The display illustrated in FIG. 42 has enhanced data to eliminate noise in order to more clearly image a particular nerve. However, in many applications, such processing may eliminate important information. Another example display is illustrated in FIG. 43 where the display includes the use of contour lines to help the clinician make sense of more data. The image in FIG. 43 corresponds to a tissue scan of the area of tissue imaged in the MRI scan illustrated in FIG. 44 with corresponding structures identified. A further example of a data display is provided in FIG. 45 which graphically displays data from a tissue discrimination scan that reveals the right infraclavicular brachial plexus as the large white structure on the right side of the image, while the right lateral pectoral nerve is revealed in the narrow white streak on the left side of the image.

In an embodiment, the calibration of the instrument, optimization of the input signal, detection and recording of data from the array, and analysis of the data are automated. In such an embodiment, circuits, firmware and/or software operating on a processor will first initialize the equipment, then conduct the scan and gather data. Finally, the data will be analyzed to provide meaningful information to an operator. The method steps implemented in such automated processes are described below.

As a nonlimiting example of the operation of an embodiment of the present invention, one or more of the following steps may be performed in circuitry, firmware and/or software, with and/or without operator involvement, in order to initialize the equipment and conduct a nerve scan:

1. Perform start-up, self-test, and initialization of the hardware and firmware.
2. Monitor input from the control computer through the communications link.
3. Respond appropriately to commands which configure the operation including:
   a. Return the hardware/firmware version numbers (or identifiers).
   b. Return the result of a self-test or other initialization procedure.
   c. Set the amplitude, frequency, and shape of the waveform to generate.
   d. Determine whether the waveform voltage or the current is being controlled.
   e. Set the number of waveform cycles to generate before measurement.
   f. Set the number of waveform cycles to be measured.
4. Upon a command to apply the waveform to a specific electrode or electrodes, apply the waveform as specified before beginning measurement, then apply the waveform as specified during measurement.
5. Measure the resulting electrical response by:
   a. sampling the waveform (e.g., at least 20 samples per waveform cycle), b. converting the samples to digital value(s),
c. transmitting the digital sample values to the host computer,
d. when a controlled voltage is applied, measuring the corresponding current flow, and
e. when a controlled current is applied, measuring the voltage required to maintain the current waveform.
6. Return an indication of the hardware status and the success or failure of each command.

As another nonlimiting example of the operation of an embodiment of the present invention, the equipment may perform the following steps while operating to set up measurement parameters, gather data and adjust measurement parameters between data gathering windows. Such operations may be controlled and commanded by a host computer, sometimes referred to herein as a controller, connected to the equipment or by a microprocessor embedded in the electrode array assembly interface module itself, with and/or without operator involvement. Such example operations may include one or more of the following steps:

1. Establish communication with the circuitry/firmware of the nerve scan equipment over the communications link.
2. Send commands to initialize the circuitry and to set up a default configuration. A nonlimiting example of test parameters that may be configured in the equipment and nonlimiting example settings for each includes:
    a. mode=controlled voltage
    b. amplitude=2500 mV
    c. frequency=2000 Hz
    d. wave shape=sinusoidal
    e. cycles before measurement=2
    f. samples to take per cycle=20
    g. iterations over all electrodes=1
3. Determine the characteristics of the electrode array in use, including:
    a. the geometry of its physical substrate/superstructure,
    b. the number, identifiers, and size of the electrodes, and
    c. the local 2-D location coordinates of the electrodes.
4. Establish parameters for an alternative configuration, as directed by the user, including for example:
    a. amplitude, shape and frequency of the waveform(s) to be applied,
    b. selection of whether the voltage waveform or the current waveform to be applied is controlled,
    c. duration (or number of cycles) of applied signal before acquiring measurements,
    d. duration (or number of cycles) during which to acquire sample measurements,
    e. the set or sets of electrodes to which to apply the waveform,
    f. the ordering and/or grouping of the electrodes applying the waveform, and
    g. number of iterations over the set of electrodes.
5. For each electrode (or electrode set):
    a. generate the commands for the circuitry to apply the waveform,
    b. retrieve and save the samples (perhaps 400) for each electrode, and
    c. determine characteristics of each set of retrieved samples, e.g., for example, mean peak-to-peak amplitude.
6. Optionally, also measure the phase shift in the received signal.
7. Alternatively, measure the charge time of a DC-biased waveform, such as to determine capacitance.
8a. Convert the measured amplitude to volts (if the applied current is controlled).
8b. Alternatively to 8a, convert the amplitude to microamps (if the applied voltage is controlled).
9. Find the maximum and minimum amplitudes among all the valid electrode amplitudes.
10. Compute a normalized, relative "value" $R[e]$ for electrode e, such as the following nonlimiting example equation:

$R[e]$=(maximum–$A[e]$)/(maximum–minimum), where $A[e]$ is the absolute, measured amplitude for electrode e. In controlled voltage mode, $R[e]$=($A[e]$–minimum)/(maximum–minimum), since the impedance will vary inversely as the applied current.

11. Store in memory the points ($X[e]$, $Y[e]$, $R[e]$), where $X[e]$, $Y[e]$ are the location coordinates of electrode e.
12. Optionally, apply a function to the set of values $R[e]$ for all the electrodes e, which smoothes, filters, and/or exaggerates each $R[e]$ relative to its neighbors. For example, scale $R[e]$ by the vertical component of the estimated normal at electrode e. As another example, multiply each $R[e]$ times the estimated maximum curvature at electrode e (for example, scale $R[e]$ by its height relative to the mean height of its neighbors).
13. Interpolate the points ($X[e]$, $Y[e]$, $R[e]$) to estimate values at interstitial points between electrodes, e.g., to produce a continuous or near-continuous lofted surface. As a simple example, such interpolation may use three adjacent points to form a triangularly faceted surface. As another example, such interpolation may use adjacent points to form a mesh of bi-variant polynomial patches. As another example, such interpolation may use statistical analyses, e.g., Bayesian statistical methods described herein, to estimate interstitial values based upon known measurements and statistical information on the distribution (e.g., linear shape) of discriminated tissues (e.g., nerves) within body tissues.
14. Produce a display of the data, e.g., by plotting a graph of the surface, e.g., by means of one or more of the following examples:
    a. Use topographic contour lines. Plot cross-sections or grid-lined surfaces.
    b. Use shading to indicate height, e.g., lighter values for larger $R[e]$.
    c. Use shading to indicate lighting and shadows as from a light source.
    d. Use oblique views in conjunction with one or some of the above.
15. Identify and highlight "peaks" and "ridge lines" on the lofted surface.
16. Identify potential branch points of ridge lines.
17. Graphically correlate the plotted graph with physical points on the array, e.g., for example, by:
    a. overlaying the shape of the electrode array on a top view of the plot;
    b. labeling the locations of the electrodes relative to the plot of the surface, and/or
    c. displaying grid lines on the plot corresponding to grid lines on the array.
18. Optionally, allow the user to adjust the viewpoint, coloring, shading, elevation, exaggeration (peak-to-average enhancement) and other visual aspects of the surface display.

Note that at least some of the algorithmic operations attributed to the host computer could be performed by the circuitry and firmware, or by a microprocessor within the electrode interface before sending the resulting data across the communication link to the host computer, or to a display computer e.g., a personal digital assistant (PDA) or laptop computer. Further, in some embodiments, the operations will be performed by electronics (e.g., a microprocessor) within the electrode array assembly and presented on a display packaged with the electrode array assembly as a unitary package.

In an embodiment, instead of basing measurements on the mean peak-to-peak amplitude for the measured signals of or from an electrode e, the root-mean-square of the amplitudes of measured signals relative to the mean amplitude of measured signals may be used. As a further alternative, the processor may perform an algorithm that uses the peak value of a correlation function between the measured signal waveform and the applied (source) function.

In a further embodiment, the processor may perform an algorithm based on a "box-car filter" with a length equal to the applied source waveform cycle to determine the R-C (resistor-capacitor) circuit charging time of the tissue capacitance.

In a further embodiment, the processor may process the measured data using statistics related to the measured individual electrode waveform peak-to-peak amplitudes, e.g., the standard deviation for example, to quantify the quality (e.g., statistical significance, margin of error, etc.) of measurements and identify faulty or untrustworthy measurements. Additionally, nonlinear and statistical functions may be applied to the data to emphasize peaks while suppressing noise below a threshold.

Interpolation among the electrodes in an array may be performed between adjacent electrodes in a row, between adjacent electrodes in a column, and between diagonally-opposed electrodes. In the case of interpolation between diagonally opposed electrodes, information from four adjacent electrodes may be used to better approximate the contour of the signal in the interstitial space. Nonlinear interpolation methods may be used to optimize the information available across the array. Such interpolation may also be enhanced using statistics drawn from measurements on other individual electrodes, as well as statistical information on the average distribution of nerves within tissue, to permit better estimations and predictions of nerve paths.

For example, in an embodiment, the interpolation method may use the knowledge that nerves generally follow connected paths. Knowing that a nerve detected in two portions of the array most likely is connected there between, statistical methods may be used to enhance the interpolation between locations where the nerve is localized. For example, statistics may be gathered on the distribution and curvature of nerves across different distances (e.g., on the order of the separation between electrodes in an electrode array assembly), including statistics for particular nerves or parts of the body. Other knowledge, including statistical information, regarding the distribution of nerves and the typical signal produced in the electrode array assembly under various settings (e.g., waveform, frequency, voltage and/or current levels, etc.) may also be useful in interpolating results. For example, the inventors have determined that branches in nerves correspond to peaks in the detected signals. Thus, if the array data show a peak at one location in the array, there is increased likelihood that the nerve has branched, and therefore patterns corresponding to two or more nerve paths should be looked for in the surrounding data points. Such methods must take into account the fact that a nerve abnormality (e.g., neuroma) may also exhibit a peak signal, and thus if a peak signal is detected but not a connected branching nerve, there is increased probability that a neuroma is present.

One method for using knowledge about normal nerve distribution and physiology to enhance the analysis of measurement data and interpolate between electrodes involves the use of Bayesian statistics. Bayesian statistics allows the calculation of the probability of condition A given condition B where there is a statistical correlation between independent conditions A and B. Thus, given statistics on the path profiles of particular nerves (e.g., frequencies/probabilities of various curvatures) over various distances, a measurement localizing a nerve at two or more points can be used to calculate the probability of the nerve at various positions between those points (i.e., the probability the nerve lies at an intermediate point given that it is localized at two adjacent points). To support this analysis, statistics would need to be gathered on nerve path profiles over varying distances, which may include gathering statistics on the path distribution of different types of nerves and for different parts of the body. Statistical information on average measurement data for different parts of the body and for different nerve features may also be gathered to support diagnostic analysis.

An example of an embodiment for processing data involves finding the normalized impedance equivalent by determining the maximum value in the array of measured values, subtracting the individual measured values from the maximum value, and dividing the total by the difference between the maximum and minimum values in the array (maximum-value)/(maximum-minimum). This gives a range of values between 0 and 1 with the highest inverse impedance value being 1. Since the rows may be staggered on a sixty-element array like that illustrated in FIG. 40, the blank cells in a spreadsheet calculation may have values assigned that are the average of the immediately surrounding cells.

An embodiment for processing data involves finding the transverse and longitudinal slopes for each value in the array of values. These slopes are determined by finding the difference between measured values on each side of the value of interest and dividing by the linear distance between those sites. On the edges of the array, the distance between the value of interest and its neighboring value may be used, as well as the difference between those measured values; e.g., the transverse distance between values on the electrode array assembly is 5 mm, for the example array illustrated in FIG. 40. The longitudinal value is approximately 4.33 mm for the example array illustrated in FIG. 40. Thus, for this example, the transverse slope (Slope$_t$) would be $(R_1C_3-R_1C_1)/10$ mm for the $R_1C_2$ value, and the longitudinal slope (Slope$_l$) for the same cell would be $(R_2C_2-R_1C_2)/4.33$ mm. These slopes may be used to find the vector in the Z-direction by the following equation:

$$Z_{vector} = \sqrt{(0-5)*Slope_t^2 + (0-4.33)*Slope_l^2 + 5^2 + 4.33^2} \quad \text{Eq. 2}$$

Since the projection of the $Z_{vector}$ ($Z_{proj}$) on the (x,y) plane is always equivalent to $\sqrt{x^2+y^2}$, the cosine of the angle of the Normal to the (x,y,z) plane is $(Z_{proj})/Z_{vector}$. This number will approach 1 as the slope of the (x,y,z) plane approaches 0 (e.g., the Normal is vertical). Multiplying the normalized admittance values from Eq. 2 by the cosine of the Normal to the (x,y,z) plane will maintain the height of the admittance surface where peaks occur (e.g., slope is 0). The height of all other sites that have non-zero slopes will be diminished. The net effect is to narrow the profile of the peak while keeping the amplitude of the peak unchanged.

In an embodiment, multiple measurements are obtained for each electrode to obtain a statistically significant sample. The statistically significant sample size may depend upon the noise and other variation in the measurements. Between about 5 and about 15 readings may be taken for each electrode. Using statistical analysis, those electrodes exhibiting high readings for all measurements will stand out above those electrodes exhibiting random readings. For example, the standard deviation may be obtained for the data for each electrode, and those data points with a narrow deviation may be emphasized over those data points with broad deviations.

Statistical processing of the data may further be used to enhance data points (i.e., electrode positions) where there are statistically significant readings above the background noise level, while suppressing data points where measurements are close to the background or noise level. One such processing example is vertical-cosine suppression which narrows the vertical peaks to more clearly indicate the underlying nerve which is known to be a narrow structure. Another such processing example involves simple threshold gating which suppresses signals below a potentially adjustable threshold (e.g., adjustable by the operator) to reveal islands and ridges in the data.

Further mathematical processing of the data using knowledge of the linear nature of nerve structures permits "ridge following" to trace and extrapolate the path of nerves beneath the electrode array assembly. Since nerves are generally linear structures, the measured signal falls off on each side of the "ridge," so the vector normal to the signal gradient will tend to point along the path of the nerve. By connecting such vectors from electrode point to electrode point, a processor can interpolate the path of the nerve. As described below, such processing must include tests (conditions and criteria) for identifying nerve terminations and branches.

It is anticipated that the electrical connection between electrodes and the skin may vary across the array and from measurement to measurement due to inevitable inconsistencies in skin wetting, chemical variation of gels (e.g., due to contamination from the skin), etc. As a result, the impedance of each electrode may vary from one to another. In an embodiment, the relative impedance of each electrode is determined and addressed in the processing of the data by the controller. As a simple example, the impedance of the electrodes may be normalized across rows, and/or columns or across the entire array so that variations in electrode impedance are compensated for. Alternatively, each electrode may be calibrated so that individual measurements can be adjusted during data processing.

One method for calibrating electrodes or compensating for electrode-to-electrode variability involves ramping the voltage applied across each waveform electrode and the return electrode from zero and determining the lowest voltage detectable. Alternatively, or in addition, the conductive pads of the array may be packaged in contact with a conductive foil and the array checked for continuity and variability prior to removal from its package. It should be noted that if the measured impedances for all electrodes in the array are high, then it is likely that the coupling of the single return electrode (or in some embodiments the single waveform electrode 1) to the skin is poor.

Some electrodes may fail to establish a reliable electrical connection with the skin. Such situations may be addressed in the processing of data so that the test need not be interrupted to reapply or replace an electrode array assembly. An example of a method of addressing a bad electrode is to simply ignore the data from that point. A hole in the data may be acceptable. Readings from surrounding electrodes may be used to estimate the true signal by means of interpolation, such as by methods described herein. Alternatively, an average signal value for all electrodes may be applied to the missing data point.

In the controlled current mode of operation, voltage limits may be exceeded as the applied current increases. This problem can be avoided by operating in the controlled voltage mode, allowing the applied current to "follow" the controlled voltage based on the underlying impedance. Consequently, the system will not be in the position of trying to drive a particular current with inadequate voltage when the underlying impedance exceeds a critical value. Operating in the controlled voltage mode also maximizes the tissue population of voltage-gated channels in the open mode (a transmembrane voltage gradient dependent event).

As a consequence of site to site impedance differences, optimum controlled current I varies from site to site on a body, and/or individual to individual. A range of suitable currents is from about 20 µA to about 300 µA. To determine a suitable controlled current and avoid saturating (railing) sensors when operating in the controlled current mode, the following example partial algorithm for data review and analysis may be used:

1. Determine whether one or more electrodes rail at 20 µA or less. If NO, proceed with data collection up through the current range under test. If YES, proceed with data collection and answer a second question: Determine whether the exact same electrodes rail in each I level tested. If NO, data are inconclusive and the recommendation is made to use a different electrode array assembly. If YES, then subsequent data analysis should proceed as below, but omitting that specific electrode or electrodes.
2. For the set of electrodes that do not rail at 20 µA or less, and that are tested at serially increasing current, determine whether there is a current at which one or more of the electrodes in this set rails. If NO, then proceed to review data as below. If YES, then cease sampling at higher I and/or omit all data sets that include railed electrodes.
3. Of the data sets resulting from the above, determine the range of measurement error observed over the electrode array assembly. Omit data sets with measurement error exceeding some value (e.g., 15% of x for that electrode).
4. Proceed to graph data sets that survive the above three screening methods. This algorithm initiates sampling at low current (e.g., 20 µA) runs until the first data set in which any electrode rails, and then reviews the data. An exception occurs when one or more electrodes rail at 20 µA.

In an alternative embodiment, the operation may determine the viable current I range for any site, and then sample at small intervals of I, e.g., conducting scans of the site at various currents, raising the possibility of a "movie" and/or of "focusing" through the tissue.

Electrical characteristics of the tissues between waveform and return electrodes may be derived from the measure electrical parameters by a number of methods different methods and algorithms. The following example embodiment provides a suitable method for determining electrical characteristics by analyzes a series of discrete measurements made at discrete times t to estimate coefficients of a mathematical function F(t) which will provide a "best fit" approximation match to the digital numeric sequence W' at time t=iT, where T is the interval between discrete measurements i and W' is the sequence of measurement values. Such a mathematical function may be chosen from a number of parameterized functions which differ only by the values of a small number of parameters or coefficients. The independent variable of the function may be time t or a unit related to time (e.g., clock cycles, sample numbers, etc.).

Figure 9:
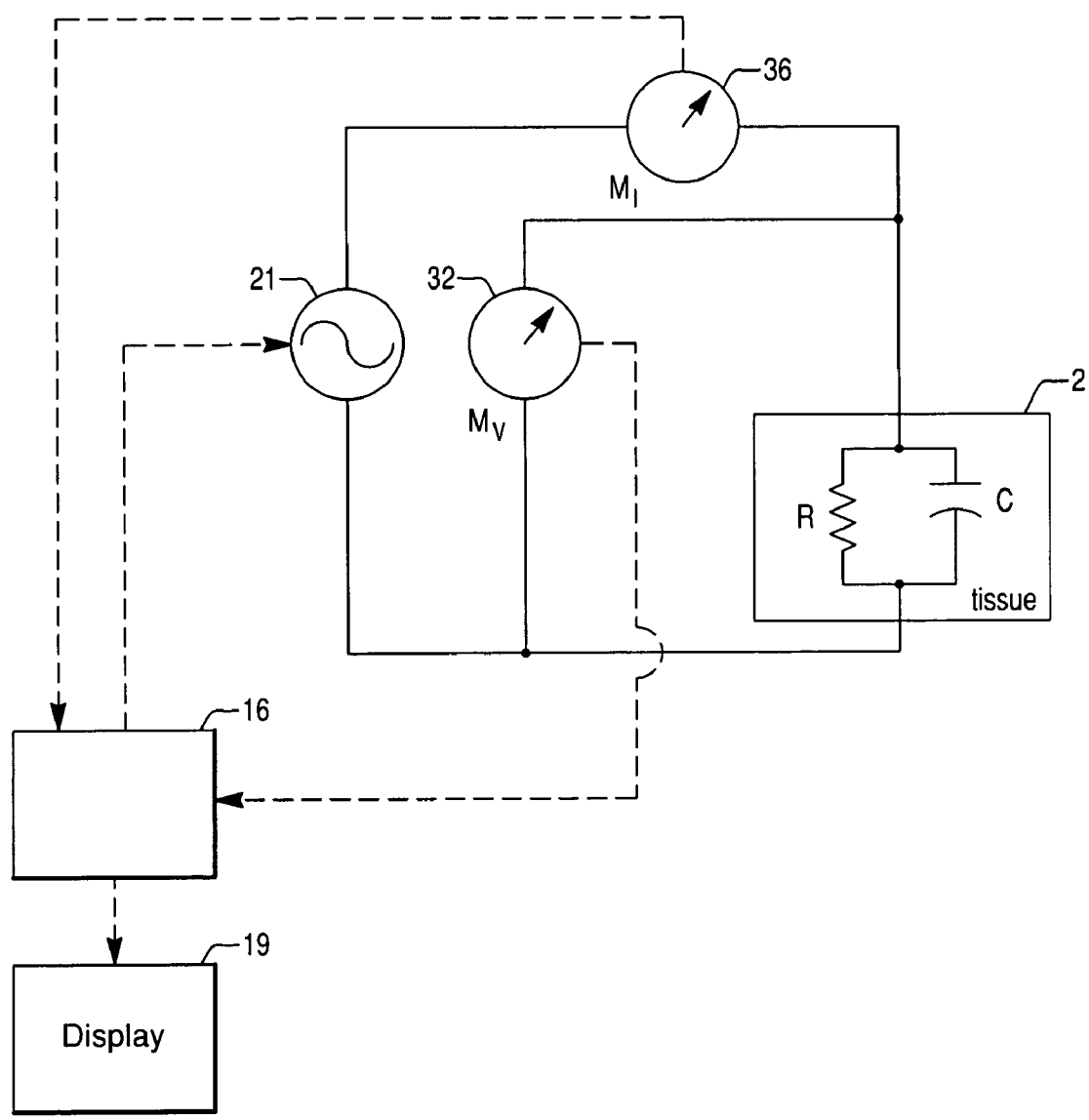
FIG. 9 illustrates a system block diagram of an embodiment of the present invention in which tissue is modeled as an RC circuit element.

Such a mathematical function may be a composite (sum or product) of several simpler component or basis functions with the same independent variable t. These component functions may comprise, for example, a constant amplitude value; one or more periodic (cyclic) functions such as a conventional sine function, cosine function, square wave; and/or an exponential decay function asymptotic to zero. These component functions are consistent with the electrical characteristics expected of a parallel RC circuit such as that illustrated in FIG. 9. For example, a constant amplitude value reflects an offset (e.g., direct current) component of an applied waveform, the cyclic function reflects the cyclic nature of the applied waveform, and the decay function reflects the capacitive nature of tissue, including nerve tissue, in the presence of an electric field. Thus, this embodiment involves estimating specific parameters of the terms of such a composite mathematical function so that the resulting function approximates (i.e., forms a "best fit" approximation for) the sequence of digital values at the times associated with those values.

For example, a suitable mathematical function may be:

$$F(t)=A_{DC}+A_{AC}[\cos(2\pi t/(NT)+P_0)]+A_0[\exp(-A_{RC}t)]$$

where
$A_{DC}$ is the amplitude of the constant direct current component,
$A_{AC}$ is the amplitude of the periodic component,
$A_0$ is the amplitude of the decay component,
$A_{RC}$ is the decay rate constant,
T is the interval between discrete measurements, and
N is the number of samples per cycle.

When the applied waveform is time varying, e.g., a sine or square wave, the time varying nature of the detected current or voltage provides information about the underlying tissue. For example, comparing the time varying received signal to the applied waveform may provide phase relationship information, e.g., the phase shift of the received signal compared to the applied waveform. An example of phase shift that may be detected is illustrated in FIG. 23, which shows an idealized received signal 150 in the presence of the zero-biased sine wave applied waveform 152. Referring to FIG. 23, the phase shift refers to the delay 159 in the peaks of the received signal 150 compared to the applied waveform 152. Since the phase shift is related to the capacitive characteristics or properties of underlying tissue, the phase relationship of the received signal can be useful in discriminating tissue types.

One method of estimating the parameters of the composite mathematical function is to represent the preprocessed sample sequence W' as the sample by sample sum of several component sequences, which correspond to the component functions. For example, there may be a component sequence of constant values, a periodic component sequence corresponding to discrete values of a cyclic function, and a component sequence corresponding to discrete values of an exponential decay. A sample by sample sum of these functions would equal the samples of the preprocessed numeric sample sequence. Such a composite function may thus be represented as $$W'[i]=W_{DC}[i]+W_{AC}[i]+W_{decay}[i]$$

where
$W_{DC}[i]=C_{DC}$,
$W_{AC}[i]=C_{AC}[\cos(2\pi i/N+C_{phase})]$,
$W_{decay}[i]=C_0[\exp(-C_{RC}iT)]$, and
$C_{DC}$, $C_{AC}$, $C_{phase}$, $C_0$, and $C_{RC}$ are parametric constants.

One method for constructing an approximation to the periodic component sequence $W_{AC}$ is to construct an intermediate aperiodic component sequence $W_{interm}$ as follows. Let the $i^{th}$ element of the intermediate sequence be the average of exactly one cycle of samples where the cycle is approximately centered on the $i^{th}$ element. This will not define the first ½ and the last ½ cycle of samples in the intermediate sequence $W_{interm}$, but portions can be set to W' or simply ignored. It may be assumed that at least several cycles of preprocessed data were acquired so that the intermediate sequence contains at least one cycle of well defined data. Here cycle means the equivalent of one cycle of the cyclic component of the applied waveform. Next, the intermediate sequence is subtracted from the preprocessed sequence (ignoring the first ½ cycle and last ½ cycle) to yield $$W_{AC}[i] \approx W'[i] - W_{interm}[i].$$

The result $W_{AC}$ will be an approximation of the cyclic sequence component of the preprocessed sample sequence. This approximation may then be correlated with the cosine and sine functions having the same period and phase as the applied waveform as given by $$C_{ACI}=2\Sigma_i(W_{AC}[i])[\cos(2\pi i/N)], \text{ and}$$

$$C_{ACj}=2\Sigma_i(SW_{AC}[i])[\sin(2\pi i/NT)],$$

where
N is the number of samples acquired per cycle of the periodic component of the applied waveform,
$C_{ACI}$ is the real part of the periodic amplitude expressed as a complex number, and
$C_{ACj}$ is the imaginary part of the periodic amplitude expressed as a complex number.
Alternatively, the periodic amplitude may be represented by a non-negative amplitude $C_{AC}$ and an angle $P_0$ as given by $$C_{AC}=\sqrt{C_{ACI}^2+C_{ACj}^2} \text{ and}$$

$$P_0=\arctan(C_{ACj}/C_{ACI}).$$

Note that this approximation works for both a periodic (preferably sinusoidal) voltage function and a periodic current function. When this method is implemented to determine $C_{AC}$ and $P_0$, the approximation $W_{AC}[i] \cong W'[i]-W_{interm}[i]$ is used in the formulae for $C_{ACI}$ and $C_{ACj}$.

The constant amplitude component $W_{DC}$ may be estimated by averaging the values of the samples that were collected over exactly an integral number of cycles (assuming that the applied waveform has a cyclic component as for a sinusoidal waveform). Alternatively, $W_{DC}$ may be set to the average of the last portion of $W_{interm}$. If there is substantial capacitance in the tissue, there will be a measurable exponential decay component $W_{decay}$, so that the average should be taken only over the last few cycles, after which presumably most of the decay will have already occurred. Either sufficient numbers of samples should be taken for this to be true, or there should be sufficient preconditioning repetitions of the applied waveform before acquiring the data, as described above.

Using the best fit mathematical function F(t), the constants which parameterize this function may be determined. These may be the parametric constants $C_{DC}$, $C_{AC}$, $C_{phase}$, $C_0$, and $C_{RC}$ in the foregoing example, or they may include other parametric constants such as the minimum and maximum amplitude, phase, duty cycle, and frequency of a rectangular function. These constants $C_{DC}$, $C_{AC}$, $C_{phase}$, $C_0$, and $C_{RC}$ may simply be estimated as above. Preferably, these values may be refined by an iterative optimization procedure by minimizing the mismatch between W' and F using well known optimization techniques. The resulting refined, optimized values $A_{DC}$, $A_{AC}$, $A_{phase}$, $A_0$, and $A_{RC}$ for the constants $C_{DC}$, $C_{AC}$, $C_{phase}$, $C_0$, and $C_{RC}$, respectively, approximately parameterize the composite mathematical function F(t) that approximates W' as given by $$F(t)=A_{DC}+A_{AC}[\cos(2\pi t/(NT)+P_0)]+A_0[\exp(-A_{RC}t)].$$

Note that this is only an example of a single embodiment; and other approximating composite functions may be used in addition to or instead of those above example as would be known to one of skill in the art.

Optionally, the values F(iT) of the best fit mathematical function may be calculated at the times iT, which correspond to the numeric samples in the sample sequence, and the values compared with the digital numbers W'[i] of the preprocessed sequence W'. Then, using the compared values, a single statistic (such as the root-mean-square of the differences) figure of merit may be determined which represents the quality of the fit, e.g., the degree of deviation or lack of confidence of this procedure, as given by $$RMS(F, W')=\sqrt{\Sigma_i(F(iT)-W'[i])^2}.$$

Using the parametric constants which characterize the best fit mathematical function F(t) the electrical properties of the tissue can be derived. The electrical properties of interest may include any of impedance, admittance, resistance, susceptance, capacitance, or phase shift, for example. Regardless whether the voltage or the current is the controlled property of the electrical waveform applied to the tissue, when using a sinusoidal waveform one can apply the complex form of Ohm's Law to find the complex impedance Z of the tissue by $$Z=V/I$$

where
- Z is the impedance (with real resistive and imaginary reactive components),
- V is the periodic component of the voltage waveform (either applied or measured),
- I is the periodic component of the current waveform (either applied or measured), and where complex quantities V and I are measured with respect to the same phase reference (i.e., synchronous cosine and sine references). If it is assumed that the parameters $A_{AC}$ and $P_0$ are known for each of the component functions approximating cyclic voltage waveform and current waveform, then the complex impedance Z is:

$$Z=(V_{AC}/I_{AC})\cos(V_P-I_P)+j(V_{AC}/I_{AC})\sin(V_P-I_P)$$

where
- $V_{AC}$ is the amplitude of the periodic voltage component,
- $V_P$ is the phase angle of the voltage component,
- $I_{AC}$ is the amplitude of the periodic current component,
- $I_P$ is the phase angle of the current component, and
- $j=\sqrt{-1}$ Further, the complex admittance Y is given by this complex division:

$$Y=1/Z$$

The real and imaginary components of Y are the conductance and susceptance, respectively. Further, the tissue resistance R and the tissue capacitance C are given by:

$$R=1/\text{real}(Y);$$

$$C=\text{imag}(Y)/(2\pi F)$$

where
- F is the frequency of the applied periodic component,
- real(Y) is the real part of Y, and
- imag(Y) is the imaginary part of Y.

The following are several alternative methods of computing the resistance and capacitance of the tissue using the values of various of the parametric constants $A_{DC}$, $A_{AC}$, $A_{phase}$, $A_0$, and $A_{RC}$ computed above.

First, if there is a non-zero constant offset (DC) voltage component $V_{DC}$ in the voltage waveform and a non-zero constant offset current component $I_{DC}$ in the current waveform, then the tissue resistance R can be computed as $$R=V_{DC}/I_{DC}$$

using Ohm's Law. This has been found to be more accurate than using the previous formula for R in a prototype of an embodiment of the present invention.

Second, there is an alternative method of computing C if there is a substantial, measurable exponential decay component $W_{decay}$ and therefore a matching decay component of F(t), namely $A_0\exp(-A_{RC}t)$. In this circumstance, the RC time constant is $$C_{RC}=1/A_{RC}.$$

Furthermore, $$C=C_{RC}/R.$$

In the case where nerve tissue is modeled as a bulk parallel RC circuit, one can obtain R and C for a controlled voltage sinusoidal waveform as follows:

$$R = -R_M(V_{M\text{-}max} + V_{M\text{-}min} + V_{A\text{-}peak})/(V_{M\text{-}max} + V_{M\text{-}min});$$

$$C = 2V_{A\text{-}peak}\sqrt{\frac{[|(V_{M\text{-}min}V_{M\text{-}max})/(V_{A\text{-}peak}^2 - V_{M\text{-}pp}^2)|]}{[\pi F R_M(V_{M\text{-}max} + V_{M\text{-}min} + V_{A\text{-}peak})]}}$$

where
- $R_M$ is the resistance across the sense resistor,
- $V_{M\text{-}min}$ is the minimum measured voltage across $R_M$,
- $V_{M\text{-}max}$ is the maximum measured voltage across $R_M$,
- $V_{A\text{-}peak}$ is the maximum applied voltage,
- $V_{M\text{-}pp}=V_{M\text{-}max}-V_{M\text{-}min}$, and
- F is the frequency of the sinusoidal periodic waveform $W_{AC}$.

Modeling the nerve tissue as a bulk parallel RC circuit, another alternative formulation for determining R and C for a controlled current waveform is:

$$R = (V_{T\text{-}max} + V_{T\text{-}min} - 2V_r)/\bar{I}$$

$$C = \frac{\bar{I}\sqrt{|(V_{T\text{-}max} - V_r)(V_{T\text{-}min} - V_r)|}}{\pi F(V_{T\text{-}max} - V_{T\text{-}min})(V_{T\text{-}max} + V_{T\text{-}min} - 2V_r)}$$

where
- $V_{T\text{-}min}$ is the minimum measured voltage across the tissue at steady state,
- $V_{T\text{-}max}$ is the maximum measured voltage across the tissue at steady state, $V_r$ is the rest potential across the tissue,
I is the controlled current amplitude, and
F is the frequency of the sinusoidal periodic waveform $W_{AC}$.

As an optional alternative to the methods described above, the best fit parameters may be inferred through analog methods, such as using analog circuit elements. Using analog derived parameters, the electrical characteristics, such as resistance and capacitance, may also be determined.

In an embodiment for nerve scan data processing, raw and/or calculated data may be treated as points in a space and interpolated according to a smooth geometric surface. Suitable functions for performing geometrical interpolation (interpolation of free-shapes with the only requirement of continuity up to a given order) are the NURBS (non-uniform rational B-splines). To accomplish this data processing, normal vectors of the NURBS surface are evaluated. For each desired point in the surface (not necessarily the data), evaluate two linearly-independent tangent vectors by deriving the NURBS surface with respect to its two parameters and evaluate the normal as the normalized vector product of the two tangents. If the surface is at least of an order 3, then the first derivative will be continuous, and so will be the normal (the surface would have no cusps). The z-component of the normal represents the "vertical-cosine." Using this process the normal will be well defined over the entire surface, including edges and corners. Then, cosine attenuation is applied to the surface. Next, the surface is re-sampled over a much finer grid, and the points attenuated over the grid using the normal vectors given at 2. Finally, these points are interpolated with a smooth surface and plot. The "vertical-cosine" attenuation algorithm simply narrows the vertical peaks (not necessarily the ridges) in the image. This is a purely geometrical algorithm and does not use any information about the underlying process. Note that this algorithm is used in computer-graphics to render 3-D objects illuminated by a vertical light source. Using NURBS, the data can be interpolated directly without pre-interpolation over a rectangular grid. Standard deviation can also be taken into account in the interpolation process, which will then become a best fit type of algorithm.

In another embodiment, data are evaluated considering the topological information that nerves must be connected paths. The data may be fit with a smooth surface (i.e., NURBS) using dedicated visualization software to "investigate" the surface. This embodiment has advantages over the "vertical-cosine" algorithm to modify the z-coordinates of the fitted surface, but the NURBS method can be used for "illumination"—light-rendering of the image. In this way, peaks and ridges may be enhanced without changing the data.

Example embodiments of particular applications are provided below.

The present invention has many uses as will be readily appreciated by those of skill in the art, some of which are described below by way of example but not by way of limitation. The present invention may be used to discriminate tissues and locate nerves so they can be avoided during surgery and other invasive procedures, e.g., during placement of surgical trochars. The present invention may be used to identify and diagnose abnormal tissue structures, e.g., injured or diseased nerves. The present invention may be used to apply a mathematical analysis to the applied voltage data to extract information specific to nerve branching in a horizontal, vertical or oblique direction. The present invention may also be used to apply a mathematical analysis to the applied voltage data to extract information specific to nerve compression, nerve traction, nerve entrapment, nerve transection, or nerve contusion. The present invention may also be used to apply a mathematical analysis to applied voltage data to extract information specific to the presence of neuromas. The present invention may also be used to apply a mathematical analysis to applied voltage data to extract information specific to myofascial trigger points or to acupuncture points. The present invention may also be used to apply a mathematical analysis to applied voltage data to extract information specific to axonal demyelination. The present invention may also be used to apply a mathematical analysis to applied voltage data to extract information specific to normal nerve supplying pathological structures, e.g., joint, tendon, muscle, bone or other soft tissues. The present invention may also be used to allow targeting of specific therapies to nerves, e.g., injection of local anesthetic or botulinum toxin. The present invention may also be used to allow monitoring of nerve tissue over time for evaluation of the development of nerve abnormalities, e.g., carpal tunnel syndrome. The present invention may also be used to allow monitoring of nerve tissue over time for evaluation of the development of nerve abnormalities, e.g., pressure effects on nerves during surgery or other prolonged static positioning situations. The present invention may also be used to allow monitoring of nerve tissue over time for evaluation of nerve repair following neurolysis or neurorrhaphy or surgical repair of nerve transections. The present invention may also be used to allow targeting of other diagnostic studies, e.g., MRI, or electrodiagnostic studies, to specific nerves.

As described above, the electrode array assembly of the present invention may be configured in a wireless configuration so that data and signals from the electrode array assembly are provided to the controller without intervening wires. This embodiment permits more convenient monitoring of peripheral nerves, such as the ulnar nerve, and simplifies equipment storage and deployment, and reduces operating room clutter. Pressure on the ulnar nerve during surgery can lead to nerve damage. It is believed that half of the injuries to ulnar nerves occurring during anesthesia and surgery are due to the position of the patient. Nerve injury rates have not changed substantially over the past thirty years, even as other anesthesia injury rates have declined. (Caplan, Closed claims Study). Thus, a need exists to monitor the ulnar nerve to detect nerve abnormalities during several types of surgery. Yet, the crowded nature of operating rooms may make it difficult to add more cables and equipment for this purpose. The wireless electrode array assembly embodiment described herein provides clinicians with a possible alternative for monitoring peripheral nerves without adding to the clutter and equipment of the operating room. Thus, a wireless electrode array assembly may permit tissue discrimination and nerve monitoring in situations where wired electrode may interfere with procedures and other equipment. Other applications for wireless electrode array assembly embodiments include certain vaginal and prostate surgeries which cause stretching of the sciatic nerve due to the extreme lithotomy position. Using embodiments of the present invention, the sciatic nerve may be monitored for dysfunction that would indicate the operative position may be causing injury, with a wireless electrode array assembly making such monitoring easier to integrated with the rest of the operation. Another potential application for the wireless electrode array assembly is in the treatment and prevention of carpal tunnel syndrome. In this application, a patient may wear a wireless electrode array assembly over the median nerve in the carpal tunnel while performing daily activities. By monitoring nerve function during such activities and providing suitable graphic or other feedback to the patient, the system may be use for training purposes to teach patients to recognize when their median nerve is becoming activated and to train them when/how to avoid the injury. This application may be used for preventing or treating the full range of repetitive use injuries. In each of these example applications, a wired electrode array assembly may be possible, but the wireless electrode array assembly may offer clinical or practical advantages.

Combining the wireless electrode array assembly embodiment with the extended wear electrode embodiment of the electrode array assembly yields another embodiment that would permit treatment of a number of nerve disorders. For example, a method for monitoring patients for nerve inflammation may include having patients wear a wireless electrode array assembly for a prolonged period of time to permit continuous or intermittent monitoring of nerves for inflammation, damage, regeneration, and repair. By monitoring nerves that are in need of regeneration, the system can identify when a repaired nerve is becoming functional, potentially well before a patient notices the return of nerve function. Such early recognition and tracking of nerve regeneration would be useful in modifying or extending regeneration treatments and for providing a prognosis to the patient. Future regeneration treatments will likely use nerve growth factors. Using various embodiments of the present invention, clinicians can use nerve scan results to target regeneration drugs to the site of injury and to monitor the effects of the treatment. As nerves regenerate slowly and treatments sometimes are ineffective, monitoring the nerves may determine whether a treatment is succeeding or not. Similarly, this embodiment may be used to monitor inflammation of nerve tissue, e.g., occurs in shingles, Guillain-Barre disease, multiple sclerosis, and other demyelinating conditions. For example, shingles leads to inflammation and local demyelinization, which may be detected by various embodiments of the present invention. Various embodiments of the present invention may be use both for detection and treatment of nerve inflammation diseases. Continuous or intermittent monitoring may be used in these treatments, and a wireless electrode array assembly permits such monitoring to take place while the patient is ambulatory, i.e., while exercising or involved in normal activities.

Various embodiments of the present invention may be integrated with image guided procedural equipment that assists clinicians and surgeons by guiding diagnostic, therapeutic and/or surgical instruments to precise locations on a subject or providing clinicians and surgeons with information to enable high precision diagnostic, therapeutic and/or surgical procedures. As used herein, "image-guided equipment" refers to any equipment which positions an instrument or guides an operator to position an instrument based upon patient position information such as contained in an image, such as a CT scan, X-ray, MRI image, ultrasound scan or tissue discrimination scan. Such equipment may be robotic, semi-robotic, tele-robotic in nature, but may also include simple positioning aids such as images projected onto a subject to represent tissues beneath the skin. Similarly, "image-guided procedures" refer to any diagnostic, therapeutic or surgical procedure in which position information, such as obtained from a diagnostic image, is used as an integral part of the procedure, such as to precisely perform an examination, therapy or surgery. Since the present invention is capable of locating, discriminating and imaging tissues, in particular nerves, this tissue location data may be inputted into image guided procedural equipment to enable the system to locate, track or avoid sensitive tissues, such as avoiding damaging nerves during invasive procedures or to perform therapeutic or surgical procedures on nerves themselves. For example, clinicians may use image guided equipment employing tissue discrimination data provided by various embodiments of the present invention to position other imaging technology (e.g., X-ray or ultrasound) on or near certain tissues (e.g., nerves). As another example, anesthesiologists may use image guided equipment employing tissue discrimination data to precisely apply anesthesia to particular nerves without damaging the nerves. As another example, acupuncture needles may be precisely implanted with the aid of patient-relative position information or by means of image-guided equipment. As a further example, surgeons may use image guided equipment employing tissue discrimination data to avoid injuring nerves during surgical procedures. To enable this integration, reference position information must be obtained along with the tissue discrimination data to enable that data to be registered within a three-dimensional (3-D) frame of reference and/or with other position-correlated data (e.g., X-ray or ultrasound images).

As described above, position information may be obtained with the use of position indicating fiducial markers added to various embodiments of the present invention to permit a position sensing system to accurately locate the waveform electrodes within a frame of reference, such as the frame of reference used by the image guided procedure equipment. The position sensing system gathers and stores information sufficient to enable a computer system to correlate or register data gathered by the tissue discrimination system, such as the location of nerves below an electrode array assembly, as well as the position of the electrode or electrode array assembly on the subject. Thus, the position sensing system and supporting elements within the tissue discrimination system (e.g., fiducials, position reporting electronics, etc.) perform both 3-D localization of data and registration and correlation of data with other 3-D localized data (e.g., data from other scans or other imaging technologies). The position sensing system may gather this data in a patient-centric frame of reference (i.e., locations on or within a subject), which may enable registering tissue discrimination data with other imaging data, such as a CT, MRI, PET, and/or ultrasound scan. Alternatively or additionally, the position sensing system may gather the tissue position information in an external frame of reference, such as an examination, treatment or operating room frame of reference, which may enable registering tissue discrimination data with image-guided equipment. Examples of position sensing systems include camera based systems, such as illustrated in FIGS. 35A-C, which sense infrared, visual or ultraviolet emitters (e.g., dots, mirrors, markers or lights), acoustic systems which feature acoustical detectors that detect acoustic emitters (e.g., infra- or ultra-sound emitters), magnetic sensors that detect the fields associated with magnetic fiducial markers, and radiofrequency sensors that detect radiofrequency (RF) radiation from RF emitters. A position sensor will include one or more sensors for obtaining sensor information and a computational circuit or processor for performing the calculations on the sensor information to calculate information related to physical location using geometric algorithms well known in the art. Non-limiting examples of fiducial markers include: (1) registration marks (e.g., LED, infrared emitters, ultraviolet emitters, light bulbs, reflectors, colored tabs, magnets, RF emitters and acoustic emitters) coupled on the electrode array assembly, or distinctive features on the electrode array assembly itself which can be seen by a camera, antenna, magnetic or acoustic sensor (i.e., microphone array) system; (2) registration marks on anatomic landmarks; and (3) registration marks on another device in use (e.g., ultrasound probe, nerve conduction velocity stimulating electrodes, scalpel, needle, etc.). Fiducial markers may emit signals, e.g., light or sound, or may reflect signals to provide a sensible indication of the marker that can be detected by the position sensor system.

Other embodiments for providing fiducial registration markers involve methods that mark other images with registration features of tissue discrimination, particularly nerve imaging. For example, an electrode array assembly placed on the skin surface interacts with other detection systems and some feature of the electrode array assembly may be picked up by other systems. For example, the electrolytes in electrode wells can include paramagnetic molecules so they are seen in a magnetic resonance imaging (MRI); radio-opaque markers (e.g., tungsten beads) on the electrode array assembly or the electrodes themselves can be detected by an X-ray image or computed tomography (CT) scan.

In an example of this embodiment, data generated by the tissue discrimination and imaging system according to the present invention may be combined with X-ray, CT scans and/or MRI images to locate and image nerves in relation to other anatomical structures, especially bones. Similarly, a combination of nerve imaging with a biplane X-ray may be used to position needles with respect to bones and nerves—i.e., the clinician uses the X-ray to see the bone and needle, and uses the nerve map to see the nerve. This method may be useful for interrogating nerves for diagnostic purposes, and positioning therapies or anesthesia (e.g., positioning injections).

An image guided procedural system according to an embodiment of the present invention thus couples (e.g., electronically via the exchange of data) the tissue discriminating and imaging system with a position sensing system and image guided equipment to enable tissue (e.g., nerve) location or image information to be used in guiding a diagnostic, therapeutic or surgical procedure. Data from the tissue discriminating and imaging system is provided to the image guided procedural equipment where it may be stored in a database, e.g., in combination with other visualization or positioning data from other sensors (e.g., X-ray, CT scan, MRI image, PET, ultrasound image). Likewise, data from the position sensing system regarding the locations of the tissue discriminating and imaging electrodes may be used to correlate and register the tissue discriminating and imaging system data with the frame of reference employed by the image guided procedural equipment so that equipment can precisely guide an examination or therapy probe (e.g., the nerve stimulator needle disclosed in U.S. Patent Application Pub. No. 2002/0065481 A1) or surgical instrument with respect to the discriminated and imaged nerve locations. Combining the functionality and capabilities of the tissue discriminating and imaging system with image guided procedural equipment enables conduct of high precision tissue examination, therapeutic treatments and/or surgery so as to more precisely treat certain tissues, avoid damaging imaged nerves or enable treatment or surgery on nerves themselves.

In embodiments combining tissue discriminating and imaging with ultrasound scans, registration may be accomplished by registering ultrasound (MEMS) probes with a nerve imaging electrode array assembly by their proximity, e.g., in a combination MEMS/EA apparatus, such as in alternative embodiments of the present invention described herein.

The present invention may be used to monitor the application, effectiveness, and duration of peripheral nerve block regional anesthesia (PNB-RA), e.g., during surgery or for the treatment of pain. The inventors have found that the sensor system of the present invention can detect local anesthetic effects because the impedance of nerves increases, presumably by the action of local anesthetics in blocking the sodium channels in nerve cell membranes. Thus, the effectiveness of anesthesia can be determined by comparing the magnitude of the admittance or impedance difference to a threshold value or to the difference prior to application of anesthesia. Similarly, during a procedure involving PNB-RA, the admittance or impedance difference may be monitored for a decreasing trend which may indicate that the anesthetic is losing effectiveness, or for the difference exceeding a threshold indicating that nerve function (e.g., feeling) has returned. In this application, the electrode array assembly may be placed and used to determine where to put the catheter or needle to apply anesthesia in the vicinity of the nerve. While anesthesia is administered, the admittance of the nerve may be monitored to determine when the admittance or impedance difference exceeds a threshold value, indicating the anesthesia has taken effect. Then, the electrode array assembly may be left on the skin over the anesthesia site to detect when the anesthesia begins to wear off. The inventors have found that an embodiment of the present invention can detect when anesthesia begins to wear off before the patient can. Upon detecting that the anesthesia is wearing off, additional anesthetic may be applied or alternative treatments initiated. An apparatus according to this embodiment may include automatic processing of the measurement data by a processor implementing an algorithm. Algorithms implemented in an automatic processor may include statistical processing of measurement data to recognize trends, comparison of measurement data to thresholds, and comparison of measurement data to stored data obtained prior to administering anesthesia.

Many neurotoxins interfere with nerve function by blocking the sodium or potassium channels in nerve cell membranes. For example, if saxitoxin were applied to a nerve, the nerve would become less active, due to fewer sodium channels existing in the open state at any given time. The relative activity of nerves can be detected with the sensor system of the current invention and its associated imaging equipment by measuring the electrical admittance or impedance over a portion of the nerve. Consequently, neurotoxins that block sodium or potassium channels can be detected using methods and apparatus similar to those used to monitor PNB-RA. Embodiments of the present invention may be used to diagnose or detect neurotoxin exposure, e.g., exposures to snake, spider, or scorpion venom; to specific microbial or plant toxins; or to certain toxic chemicals or chemical warfare agents. The foregoing description of the embodiments of the invention has been presented for purposes of illustration. It is not intended to be exhaustive or to limit the invention to the precise form disclosed, and obviously many modifications and variations are possible in light of the above disclosure.

Nerve imaging according to various embodiments of the present invention may be used to aid in vertebroplasty for vertebral collapse treatments. In a vertebral collapse treatment, a needle is placed into the vertebra to permit the injection of methyl methacrylate, which polymerizes to form a reinforcing structure. This procedure requires placing the needle under the transverse process in order to enter the vertebra. Because this is where the spinal root nerve lies, the procedure carries a risk of pushing the needle into the spinal root nerve, which can cause significant nerve damage. Imaging the nerve with various embodiments of the present invention will allow the clinician to position the needle so as to avoid the nerve. In an embodiment, the imaging system of the present invention may be combined with a radiographic scanner, e.g., computed tomography (CT), to provide precise nerve location information that can be used to guide the needle. Nerve imagining according to various embodiments of the present invention will provide a planar location of the nerve that can be combined, e.g., by means of co-registration, with the CT scan database that is used to position and guide the insertion of the needle. This embodiment may include the use of fiducial marks placed on the body, e.g., dye or X-ray opaque dots, before or during nerve scanning that can be correlated to the CT scan data. An example of such fiducial registration markers is small, dense metal (e.g., lead) disks that might be applied at the corners of the electrode array assembly and which will be recorded on the CT scan. Similarly, paramagnetic material may be used for fiducial registration marks that can be resolved by MRI imaging. Marking the corners (or other characteristic dimension of the nerve imaging electrode array assembly) with marks that will be recorded in the MRI scan data will permit a computer to co-register the two image datasets to generate a combined image that can be displayed for the clinician, or used in a robotic, tele-robotic, or computer guided surgery apparatus to reduce the risk of damaging nerve tissue.

In a related embodiment, a nerve stimulator electrode may be added to the end of the vertebroplasty needle to permit inputting a source signal (controlled voltage or controlled current) as the needle proceeds into the body. When the needle approaches the nerve, a resulting signal can be detected by the tissue discriminating system. This information then can be used to alert the clinician in time to redirect the needle away from the nerve.

In a similar embodiment, the methods and apparatus described above may be applied to procedures associated with disc decompression. In such procedures, a device is inserted into a protruded disk to permit fluid aspiration. This procedure must also avoid the nerves in the spine. Thus, the same methods and procedures described for vertebral collapse treatments may be applied equally for disc decompression treatments.

A method for treating certain nerve disorders involves heating the nerve using radio frequency radiation from a radio frequency (RF) probe. For this treatment to be effective, the RF probe must be positioned close to the target nerve. The current nerve location method for such treatment involves the use of bony landmarks, but such landmarks are useful only in the vicinity of certain bony structures (e.g., a spinal process) and in certain other situations. With nerve imaging according to various embodiments of the present invention, a clinician can insert a RF probe down to a nerve, stimulate it to ensure that the probe is near the nerve, and then apply RF treatment to the nerve without the need for bony landmarks. RF lesioning of nerves at trigger points may be used to permanently treat myofascial pain syndromes. Nerve discrimination and imaging according to various embodiments of the present invention would make this procedure more efficient and could be combined with an image guided system to make the process even more so.

Further information regarding the size and health of nerves, or to distinguish nerves from other tissues, may be obtained by measuring the decay of the signal (current or voltage) following cessation of the input signal. As illustrated in FIG. 24, due to the capacitive characteristics that have been observed in nerve tissue, the signal received at the receiving electrode does not drop immediately to zero when the input signal is removed, but instead declines over a brief time 163 as would a stored charge in a resistor-capacitor circuit. Consequently, a decay rate for the signal 162 can be calculated to measure the capacitance of the nerve which may be used as a measure of nerve health and function.

In an embodiment, data, particularly processed data and display images, are transmitted from the controller to a server or maintained in a database upon a data storage device accessible via a server where data can be made available for access via a network, e.g., the Internet. Data and scan images may be stored, e.g., in the form of HTML web pages, for access by clinicians via a computer operating an Internet browser. In variations of this embodiment, data and scan images from a variety of subjects, perhaps including standard or amalgamated images, may be accessed to compare and contrast with images from a particular scan. Library and/or reference images may be maintained for each major nerve, providing a generic atlas of neurons as identified and measured using embodiments of the present invention. The library may also maintain images of various nerve injuries, neuromas, nerve diseases, nerve conditions, and nerves exposed to various anesthetics or neurotoxins, which would help clinicians interpret nerve scans, recognize nerve conditions, and develop appropriate treatments or procedures.

In another embodiment, a generic atlas of nerves and/or a library of neuromas and other nerve conditions may be stored in suitable media and in a form suitable for displaying the images on a personal computer, laptop computer, personal digital assistant (PDA) or similar display systems that may be developed. In this manner, a clinician may have ready access to images useful for interpreting nerve scan results.

In an embodiment, the tissue discriminating and imaging system components may be miniaturized, ruggedized, configured for battery power, and assembled in a unitary package or housing as a unitary module or unitary device, rendering the system suitable for use in paramedic applications. An example of such a configuration is illustrated in FIG. 29. In such an embodiment of the system, nerve scan images and data may be communicated to a personal computer, laptop computer, personal digital assistant (PDA), e.g., by means of an infrared datalink or electronic cables. This embodiment may also be combined with a digital library containing a generic nerve atlas and a library of nerve images showing normal and injured/diseased conditions as imaged by embodiments of the present invention, along with medical procedures (e.g., locating and administering anesthetic to particular nerves) and device operating instructions. Further, this embodiment may be combined with telephone, satellite, WIFI or other wire-based or wireless data communication capability to transmit nerve scan results to a hospital or telemedicine facility. For example, the system could be configured for use in military combat situations, packaged and provisioned for use in field hospitals or on the battlefield. As another example, the system could be configured for use in ambulances, medical evacuation helicopters, and other civilian medical rescue vehicles. Such embodiments could aid in the prompt and effective treatment of major injuries by permitting a paramedic, corpsman, or medic to rapidly locate nerves and apply PNB-RA instead of having to administer general anesthetic or systemic medication e.g., morphine. Without such an embodiment, paramedics cannot accurately locate nerves in order to effectively apply local anesthetic. Permitting the field medical attendant to effectively block pain with local anesthetic would speed recovery and allow the patient to remain responsive and potentially mobile. In a combat situation, injured soldiers could be treated for pain and remain capable of continued mission participation, communications, or evacuating themselves.

Figure 38:
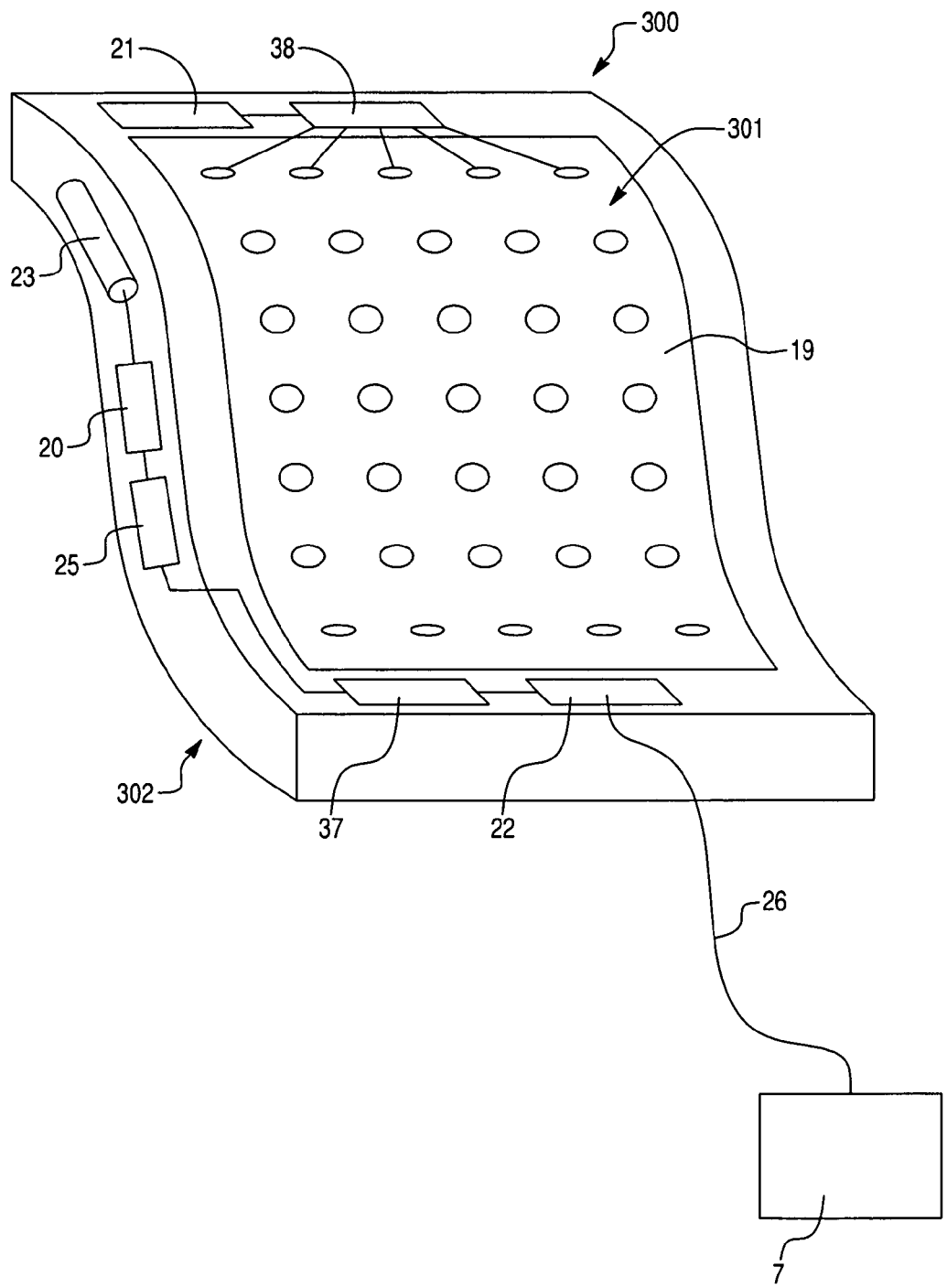
FIG. 38 illustrates a unitary tissue discrimination system according to an embodiment of the present invention.

In a related embodiment, the electronics, power supply, and display may be integrated with the sensor system to provide a nerve locating patch assembly. As illustrated in FIG. 38, the basic system components are miniaturized and contained within a unitary package about the size of the electrode array assembly. This embodiment could be configured as a flexible pad 300 featuring a first surface containing the electrodes 302 which is applied to the skin, and a second surface 301 containing a display 19 for displaying the nerve scan results. The display 19 may be any type of display known in the art sufficient to present the scan results in an easy-to-understand manner. For example, the display may be an array of LED corresponding to the locations of the electrodes. As another example embodiment, the display could be one or more liquid crystal displays (LCD), which may include a backlight capability for night use. An example LCD display that provides a simple display of electrodes comprises an array of pixels formed by groups of liquid crystal pixel elements that correspond to locations of each of the electrodes in the array underlying the display, and are configured to activate to absorb or reflect light depending upon the signal received from the corresponding electrode. Such pixel groups may be configured (e.g., including crystals of varying sensitivity) to display intensity (i.e., degree of absorbed or reflected light) related to the relative signal strength of the signal sensed by the corresponding electrode. An example of such a display is illustrated in FIG. 27. The return electrode 7 may be connected by a cable 26 to the pad 300 to permit placing the electrode at an appropriate separation distance. Cable 26 linking the pad 300 to the return electrode 7 may be of a length suitable for obtaining good nerve scan data, and/or may be marked with distance indications (e.g., inch marks) to permit the operator to position the electrode at a particular distance. Circuitry associated with the system may be packaged within the pad, e.g., around the periphery, or may be packaged separately and connected to the pad by a data and power link (e.g., cable). Such circuitry may include signal driver circuitry (e.g., a waveform generator 21 and control circuitry/switches 38), signal analysis circuitry (e.g., amplifiers 22, signal conditioners 37, and switches), and controller circuitry (e.g., a microprocessor 20 and memory 25 for storing software and data). The power supply may be a battery 23, which may be permanent, rechargeable or removable (i.e., replaceable), or other suitable, portable power sources, e.g., a fuel cell or photocell. These embodiments provide a portable system that may be suitable for paramedic and military type applications where there is a need for the unit to be self-contained.

In a further configuration of the foregoing embodiment, an integrated controller, signal generator, data processor (which may be integrated into the controller), display and associated circuitry (the "controller and display module") may be assembled into a unit that includes an electrical connection for connecting a disposable electrode array assembly that is configured as described herein. In various embodiments, the power supply may be integrated with the controller and display module or may be separate and configured to be connected to a power supply within the controller and display module. In a further embodiment, the power supply may be disposable batteries integrated within (e.g., about the periphery) the disposable electrode array assembly, so that when the electrode array assembly is connected to the controller and display module, the module is powered by the batteries in the electrode array assembly. Such disposable electrode array assemblies may be stored in sealed packages to assure sterility and maintain electrolyte gel filled electrodes in condition suitable for use. These embodiments provide a portable system that can be reused by attaching new electrode array assemblies.

In a related embodiment, the pad 300 may be made of soft rubber or plastic materials with electronics positioned around the periphery to permit an attending clinician or medic to push a small punch through the pad sufficiently large to permit a hypodermic needle to be passed directly through the pad and into the subject, thereby permitting prompt and accurate administration of anesthesia on an imaged nerve without the need to remove the pad. A punch or drill would be used to create a hole in the pad at the appropriate point to prevent the hypodermic needle from cutting a core of the pad material that might be injected into the patient. This embodiment may have particular utility in a paramedic and military application where prompt, accurate administration of local anesthetic must be provided by laypersons, perhaps under stress or adverse conditions. This embodiment could continue functioning after being pierced by a needle in order to permit the monitoring of the anesthesia, such as to indicate when anesthesia should be re-administered.

In the above embodiments, the system may be distributed in a sterile package that can be opened when the system is to be used. A sealing layer on the first surface may be used to keep the electrode surface 302 clean and the coupling interface material in place. In an embodiment, removing the sealing layer may trigger a switch, thereby turning the system on, e.g., by applying battery power to the microprocessor. A sealing layer may also be applied to the return electrode 7 to keep the electrode clean and maintain a layer of coupling interface material. So packaged, the system can remain ready for use for extended periods of time and then be rapidly opened and applied to a patient when needed.

In a related embodiment, the pad 300 may include datalink electronics, e.g., a wireless or infrared datalink, to uplink nerve scan data to a computer, e.g., a rugged laptop computer, for further analysis. Such a portable computer may contain generic anatomy and diagnostic reference libraries as discussed herein. The portable computer may also include diagnostic logic and knowledge libraries to enable it to recognize and diagnose nerve conditions based upon the uplinked nerve scan data. In an embodiment, such a portable computer may be connected to a network, e.g., the Internet, radio or satellite communication capabilities to communicate the nerve scan data and analysis to another location, e.g., a hospital, field hospital, or telemedicine center.

Among the embodiments and applications contemplated in the present invention is the use of the invention on animals e.g., in veterinary and research use. Thus, references to patients or subjects herein encompass animals, e.g., horses, dogs, cats, cattle, swine, goats, rodents, and the like. Similarly, references to skin herein encompass the hide or skin of an animal, which hide or skin may have to be pre-treated to allow adequate measurements.

The foregoing description of various embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments and with various modifications as are suited to the particular use contemplated.

We claim:

1. A method of discriminating a location of nerve tissue within a subject, comprising:
placing a waveform electrode array on skin of the subject, wherein each electrode in the waveform electrode array has an area of no more than approximately 10 mm$^2$;
placing a return electrode on skin of the subject at a position on the skin removed from the waveform electrode array at a linear inter-electrode separation distance that falls within a tail region of an impedance v. distance curve for the subject;

applying a signal serially to each of the electrodes in the waveform electrode array and the return electrode;

measuring a change in a characteristic of the signal resulting from transmission through tissue between each electrode in the waveform array and the return electrode; and discriminating a location of nerve tissue located beneath the waveform electrode array by processing the measured change in the characteristics of the signal to identify anisotropic features in underlying tissue.

2. The method of discriminating a location of nerve tissue within a subject of claim 1, wherein the applied signal employs a single frequency between approximately 500 Hz and approximately 2500 Hz.

3. The method of discriminating a location of nerve tissue within a subject of claim 1, wherein the measured change in the characteristics of the signal comprises voltage.

4. The method of discriminating a location of nerve tissue within a subject of claim 1, wherein the measured change in the characteristics of the signal comprises current.

5. The method of discriminating a location of nerve tissue within a subject of claim 1, wherein the measured change in the characteristics of the signal comprises a phase shift.

6. The method of discriminating a location of nerve tissue within a subject of claim 1, wherein:

measuring a change in a characteristic of the signal comprises measuring an electrical characteristic at discrete times to generate a data series; and processing the measured change in the characteristics of the signal to identify anisotropic features in underlying tissue comprises:

using the data series to derive coefficients of a mathematical function approximating the signal resulting from transmission through nerve tissue between each individual electrode in the waveform electrode array and the return electrode; and using the derived coefficients of the mathematical function to calculate an electrical characteristic of the nerve tissue between each individual electrode in the waveform electrode array and the return electrode.

7. The method of discriminating a location of nerve tissue within a subject of claim 6, wherein the characteristic of the signal resulting from transmission through tissue between each electrode in the waveform array and the return electrode is impedance.

8. The method of discriminating a location of nerve tissue within a subject of claim 6, wherein the characteristic of the signal resulting from transmission through tissue between each electrode in the waveform array and the return electrode is conductance.

9. The method of discriminating a location of nerve tissue within a subject of claim 6, wherein the characteristic of the signal resulting from transmission through tissue between each electrode in the waveform array and the return electrode is susceptance.

10. The method of discriminating a location of nerve tissue within a subject of claim 6, wherein the characteristic of the signal resulting from transmission through tissue between each electrode in the waveform array and the return electrode is reactance.

11. The method of discriminating a location of nerve tissue within a subject of claim 6, wherein the characteristic of the signal resulting from transmission through tissue between each electrode in the waveform array and the return electrode is capacitance.

12. The method of discriminating a location of nerve tissue within a subject of claim 6, wherein the method is accomplished for each electrode within the waveform electrode array, and the measured change in the characteristic of the signal associated with each electrode in the waveform electrode array is used to image a discriminated location of nerve tissue beneath the array of waveform electrodes by processing the measured change in the characteristics of the signal to identify anisotropic features in tissue underlying each electrode in the waveform electrode array.

13. The method of discriminating a location of nerve tissue within a subject of claim 12, wherein the image of the discriminated location of nerve tissue is presented on a display device.

14. The method of discriminating a location of nerve tissue within a subject of claim 12, wherein the image is used to generate a data set representing a location of the discriminated nerve tissue within the subject, further comprising storing the data set in a database.

15. The method of discriminating a location of nerve tissue within a subject of claim 1, wherein the method is repeated a number of times with a number of waveform electrode arrays positioned on a number of different locations on the skin of the subject, the location of each waveform electrode array is recorded each time, and the discriminated location of nerve tissue located beneath the waveform electrode array associated with each waveform electrode array location is used to generate a plurality of discriminated locations of nerve tissue beneath the skin of the subject.

16. The method of discriminating a location of nerve tissue within a subject of claim 15, wherein the recorded locations of the waveform electrode array and the plurality of discriminated locations of nerve tissue are used to generate an image of nerve tissue beneath the skin of the subject.

17. The method of discriminating a location of nerve tissue within a subject of claim 16, wherein the generated image of nerve tissue is used to generate a data set representing locations of nerve tissue within the subject, further comprising storing the data set in a database.

18. The method of discriminating a location of nerve tissue within a subject of claim 1, wherein the applied signal employs a single frequency between approximately 1700 Hz and approximately 2000 Hz.

19. The method of discriminating a location of nerve tissue within a subject of claim 1, wherein the linear inter-electrode separation distance is approximately 20 cm.

* * * * *